(12) United States Patent
Altelaar et al.

(10) Patent No.: US 11,624,082 B2
(45) Date of Patent: Apr. 11, 2023

(54) METHOD FOR MONITORING KINASE ACTIVITY IN A SAMPLE

(71) Applicant: UNIVERSITEIT UTRECHT HOLDING B.V., Utrecht (NL)

(72) Inventors: Adrianus Fredrik Maarten Altelaar, Utrecht (NL); Thierry Thomas Schmidlin, Utrecht (NL)

(73) Assignee: UNIVERSITEIT UTRECHT HOLDING B.V., Utrecht (NL)

( * ) Notice: Subject to any disclaimer, the term of this patent is extended or adjusted under 35 U.S.C. 154(b) by 0 days.

(21) Appl. No.: 17/254,116

(22) PCT Filed: Jun. 21, 2019

(86) PCT No.: PCT/EP2019/066501
§ 371 (c)(1),
(2) Date: Dec. 18, 2020

(87) PCT Pub. No.: WO2019/243590
PCT Pub. Date: Dec. 26, 2019

(65) Prior Publication Data
US 2021/0262007 A1    Aug. 26, 2021

(30) Foreign Application Priority Data
Jun. 21, 2018 (EP) .................... 18179104

(51) Int. Cl.
C12N 1/20 (2006.01)
C12Q 1/37 (2006.01)
C12Q 1/48 (2006.01)

(52) U.S. Cl.
CPC .............. C12Q 1/37 (2013.01); C12Q 1/485 (2013.01)

(58) Field of Classification Search
None
See application file for complete search history.

(56) References Cited

U.S. PATENT DOCUMENTS 8,618,248 B2 * 12/2013 Gygi .................... C07K 14/715
530/326
2005/0003450 A1    1/2005 Rush et al.

FOREIGN PATENT DOCUMENTS

| EP | 2124051 | 11/2009 |
|---|---|---|
| WO | 2010/040024 | 4/2010 |
| WO | 2012/052711 | 4/2012 |
| WO | 2013/055780 | 4/2013 |

OTHER PUBLICATIONS

Schmidlin et al., Assessment of SRM, MRM3, and DIA for the targeted analysis of phosphorylation dynamics in non-small cell lung cancer. Proteomics 2016, 16, 2193-2205.*
Li et al., Autophosphorylation of Akt at Threonine 72 and Serine 246. J Biol Chem vol. 281, No. 19, pp. 13837-13843, May 12, 2006.*
Cheung et al, Immobilized metal ion affinity chromatography: a review on its applications. Appl Microbiol Biotechnol (2012) 96:1411-1420.*
Song et al., Discovery of structural characteristics of RIP1K for activity control using the combination method. Journal of Molecular Structure 1100 (2015) 272-278.*
Prely et al., Quantification of matrix metalloprotease-9 in bronchoalveolar lavage fluid by selected reaction monitoring with microfluidics nano-liquid-chromatography-mass spectrometry. Journal of Chromatography A, 1246 (2012) 103-110.*
Thierry Schmidlin et al, Assessment of SRM, MRM 3 , and DIA for the targeted analysis of phosphorylation dynamics in non-small cell lung cancer, Proteomics, vol. 16, No. 15-16, Jun. 27, 2016, pp. 2193-2205.
Thierry Schmidlin et al, Assessment of SRM, MRM 3 , and DIA for the targeted analysis of phosphorylation dynamics in non-small cell lung cancer—supporting information, Proteomics, vol. 16, Jun. 27, 2016, pp. 1-50.
Harm Post et al, Robust, Sensitive, and Automated Phosphopeptide Enrichment Optimized for Low Sample Amounts Applied to Primary Hippocampal Neurons, Journal of Proteome Research, vol. 16, No. 2, Dec. 6, 2016, pp. 728-737.
Sara Fernandez Gaitero et al., Abstract 1221: Triple-negative breast cancer (TNBC) phosphoproteomics, Cancer Res. vol. 77, No. 13 supp, Jul. 1, 2017, p. 322.
Erik L. De Graaf et al, Signal Transduction Reaction Monitoring Deciphers Site-Specific PI3K-mTOR/MAPK Pathway Dynamics in Oncogene-Induced Senescence, Journal of Proteome Research, vol. 14, No. 7, Jun. 2, 2015, pp. 2906-2914.
Erik L. De Graaf et al., Phosphoproteome Dynamics in Onset and Maintenance of Oncogene-induced Senescence, Molecular & Cellular Proteomics, vol. 13, No. 8, Aug. 1, 2014, pp. 2089-2100.
Cao, Muqing et al. "Activation loop phosphorylation of a protein kinase is a molecular marker of organelle size that dynamically reports flagellar length" PNAS Jul. 23, 2013, vol. 110, No. 30, pp. 12337-12342.
Fabbro, Doriano et al. "Ten things you should know about protein kinases: IUPHAR Review 14" British Journal of Pharmacology, 2015, 172, pp. 2675-2700.
Modi, Vivek et al. "Defining a new nomenclature for the structures of active and inactive kinases" PNAS, Apr. 2, 2019, vol. 116, No. 14, pp. 6818-6827.
Scheef, Eric D. et al. "Structure of the Pseudokinase VRK3 Reveals graded Catalytic Site, a Highly Conserved Kinase Fold, and a Putative Regulatory Binding Site" Structure 17, 128-138, Jan. 14, 2009.

* cited by examiner

Primary Examiner — Tekchand Saidha
(74) Attorney, Agent, or Firm — Casimir Jones, S.C.; Tanya A. Arenson

(57) ABSTRACT

The present invention relates to a method for monitoring kinase activity or activation in a sample, the method comprises the steps of a) providing a sample comprising a kinase, b) incubating the sample with a protease to cleave the kinase provided in step a) into protease specific proteolytic peptides, c) applying phosphopeptide enrichment to the sample, d) analysing the sample obtained in step c) via liquid chromatography-mass spectrometry, and e) detecting phosphorylations of the kinase provided in step a), wherein the detection of step e) is performed only in case a proteolytic peptide associated with the activation region of the kinase is identified.

17 Claims, 34 Drawing Sheets

Specification includes a Sequence Listing.

| Modified Peptide Sequence | Common Kinase Name and Phosphosite Localization | Uniprot ID and Name | Precursor Ion Charge | Precursor Ion m/z | SEQ ID |
|---|---|---|---|---|---|
| NT[+80.0]FVGTPFWMAPEVIK | MST3 (T190), YSK1 (T174) | sp|Q9Y6E0|STK24_HUMAN, sp|O00506|STK25_HUMAN | +2 | 958,954456 | SEQ ID NO: 1 |
| NT[+80.0]FVGTPFWM[+16.0]APEVIK | MST3 (T190), YSK1 (T174) | sp|Q9Y6E0|STK24_HUMAN, sp|O00506|STK25_HUMAN | +2 | 966,951913 | SEQ ID NO: 2 |
| IADFGLS[+80.0]K | CaMK4 (S189), RIPK2 (S168) | sp|Q16566|KCC4_HUMAN, sp|O43353|RIPK2_HUMAN | +2 | 465,720251 | SEQ ID NO: 3 |
| S[+80.0]VVGTPAYLAPEVLR | PKD1/PKCμ (S742), PKD3 (S735) | sp|Q15139|KPCD1_HUMAN, sp|O94806|KPCD3_HUMAN | +2 | 826,426388 | SEQ ID NO: 4 |
| T[+80.0]FC[+57.0]GTPDYIAPEIIAYQPYGK | PKCα (T497), PKCβ (T500), PKCγ (T514) | sp|P17252|KPCA_HUMAN, sp|P05771|KPCB_HUMAN, sp|P05129|KPCG_HUMAN | +3 | 828,711281 | SEQ ID NO: 5 |
| TFC[+57.0]GT[+80.0]PDYIAPEIIAYQPYGK | PKCα (T501), PKCβ (T504), PKCγ (T518) | sp|P17252|KPCA_HUMAN, sp|P05771|KPCB_HUMAN, sp|P05129|KPCG_HUMAN | +3 | 828,711281 | SEQ ID NO: 6 |
| DIY[+80.0]ETDYYR | IGF1R (Y1161), InsR (Y1185) | sp|P08069|IGF1R_HUMAN, sp|P06213|INSR_HUMAN | +2 | 659,255383 | SEQ ID NO: 7 |
| DIYETDY[+80.0]YR | IGF1R (Y1165), InsR (Y1189) | sp|P08069|IGF1R_HUMAN, sp|P06213|INSR_HUMAN | +2 | 659,255383 | SEQ ID NO: 8 |
| DIYETDYY[+80.0]R | IGF1R (Y1166), InsR (Y1190) | sp|P08069|IGF1R_HUMAN, sp|P06213|INSR_HUMAN | +2 | 659,255383 | SEQ ID NO: 9 |
| LIEDNEY[+80.0]TAR | Fyn (Y420), Lck (Y394), Yes (Y426), Src (Y419) | sp|P06241|FYN_HUMAN, sp|P06239|LCK_HUMAN, sp|P07947|YES_HUMAN, sp|P12931|SRC_HUMAN | +2 | 652,281932 | SEQ ID NO: 10 |
| WTAPEAALY[+80.0]GR | Fyn (Y440), Yes (446), Src (Y439) | sp|P06241|FYN_HUMAN, sp|P07947|YES_HUMAN, sp|P12931|SRC_HUMAN | +2 | 657,797552 | SEQ ID NO: 11 |
| VIEDNEY[+80.0]TAR | HCK (Y411), Lyn (Y397) | sp|P08631|HCK_HUMAN, sp|P07948|LYN_HUMAN | +2 | 645,274107 | SEQ ID NO: 12 |
| IGDFGLAT[+80.0]VK | Araf (T454), Braf (T599), C-Raf/Raf1 (T491) | sp|P10398|ARAF_HUMAN, sp|P15056|BRAF_HUMAN, sp|P04049|RAF1_HUMAN | +2 | 550,773015 | SEQ ID NO: 13 |
| PPYT[+80.0]DYVSTR | ICK (T157), MAK (T157) | sp|Q9UPZ9|ICK_HUMAN, sp|Q20794|MAK_HUMAN | +2 | 639,773743 | SEQ ID NO: 14 |
| PPYT[+80.0]DY[+80.0]VSTR | ICK (T157/Y159), MAK (T157/Y159) | sp|Q9UPZ9|ICK_HUMAN, sp|Q20794|MAK_HUMAN | +2 | 679,756909 | SEQ ID NO: 15 |
| PPYTDY[+80.0]VSTR | ICK (Y159), MAK (Y159) | sp|Q9UPZ9|ICK_HUMAN, sp|Q20794|MAK_HUMAN | +2 | 639,773743 | SEQ ID NO: 16 |
| EYGS[+80.0]PLK | CDK11A (S577), CDK11B (S589) | sp|Q9UQ88|CD11A_HUMAN, sp|P21127|CD11B_HUMAN | +2 | 437,191326 | SEQ ID NO: 17 |
| TWT[+80.0]LC[+57.0]GTPEYLAPEIILSK | PKAα (T198), PKAβ (T198), PKAγ (T198) | sp|P17612|KAPCA_HUMAN, sp|P22694|KAPCB_HUMAN, sp|P22612|KAPCG_HUMAN | +2 | 1136,552188 | SEQ ID NO: 18 |

FIG. 6A

| Modified Peptide Sequence | Common Kinase Name and Phosphosite Localization | Uniprot ID and Name | Precursor Ion Charge | Precursor Ion m/z | SEQ ID |
|---|---|---|---|---|---|
| TWTLC[+57.0]GT[+80.0]PEYLAPEIILSK | PKAα (T202), PKAβ (T202), PKAγ (T202) | sp\|P17612\|KAPCA_HUMAN, sp\|P22694\|KAPCB_HUMAN, sp\|P22612\|KAPCG_HUMAN | +2 | 1136,552188 | SEQ ID NO: 19 |
| GEEVY[+80.0]VK | Tie1 (Y1007), GCN2 (Y70) | sp\|Q9P2K8\|E2AK4_HUMAN, sp\|P35590\|TIE1_HUMAN | +2 | 452,196609 | SEQ ID NO: 20 |
| DPDY[+80.0]VR | VGFR2 (Y1059), VGFR3 (Y1068) | sp\|P35968\|VGFR2_HUMAN, sp\|P35916\|VGFR3_HUMAN | +2 | 422,665476 | SEQ ID NO: 21 |
| LC[+57.0]DFGVSGQLIDS[+80.0]M[+16.0]ANSFVGTR | MEK1 (S218), MEK2 (S222) | sp\|Q02750\|MP2K1_HUMAN, sp\|P36507\|MP2K2_HUMAN | +3 | 824,030797 | SEQ ID NO: 22 |
| LMTGDT[+80.0]YTAHAGAK | Abl (T392), Abl2/Arg (T438) | sp\|P00519\|ABL1_HUMAN, sp\|P42684\|ABL2_HUMAN | +2 | 758,828724 | SEQ ID NO: 23 |
| LM[+16.0]TGDT[+80.0]YTAHAGAK | Abl (T392), Abl2/Arg (T438) | sp\|P00519\|ABL1_HUMAN, sp\|P42684\|ABL2_HUMAN | +3 | 511,553213 | SEQ ID NO: 24 |
| LMTGDTY[+80.0]TAHAGAK | Abl (Y393), Abl2/Arg (Y439) | sp\|P00519\|ABL1_HUMAN, sp\|P42684\|ABL2_HUMAN | +2 | 758,828724 | SEQ ID NO: 25 |
| LM[+16.0]TGDTY[+80.0]TAHAGAK | Abl (Y393), Abl2/Arg (Y439) | sp\|P00519\|ABL1_HUMAN, sp\|P42684\|ABL2_HUMAN | +3 | 511,553213 | SEQ ID NO: 26 |
| LMTGDTYT[+80.0]AHAGAK | Abl (T394), Abl2/Arg (T440) | sp\|P00519\|ABL1_HUMAN, sp\|P42684\|ABL2_HUMAN | +3 | 506,221574 | SEQ ID NO: 27 |
| LM[+16.0]TGDTYT[+80.0]AHAGAK | Abl (T394), Abl2/Arg (T440) | sp\|P00519\|ABL1_HUMAN, sp\|P42684\|ABL2_HUMAN | +3 | 511,553213 | SEQ ID NO: 28 |
| GEPNVSY[+80.0]IC[+57.0]SR | GSK3A (Y279), GSK3B (Y216) | sp\|P49840\|GSK3A_HUMAN, sp\|P49841\|GSK3B_HUMAN | +2 | 681,281409 | SEQ ID NO: 29 |
| AENGLLMT[+80.0]PC[+57.0]YTANFVAPEVLK | RSK1/p90RSK (T573), RSK2 (T577) | sp\|Q15418\|KS6A1_HUMAN, sp\|P51812\|KS6A3_HUMAN | +3 | 840,063438 | SEQ ID NO: 30 |
| AENGLLM[+16.0]T[+80.0]PC[+57.0]YTANFVAPEVLK | RSK1/p90RSK (T573), RSK2 (T577) | sp\|Q15418\|KS6A1_HUMAN, sp\|P51812\|KS6A3_HUMAN | +3 | 845,395076 | SEQ ID NO: 31 |
| TAGTSFMMT[+80.0]PYVVTR | JNK1 (T183), JNK3 (T221) | sp\|P45983\|MK08_HUMAN, sp\|P53779\|MK10_HUMAN | +2 | 871,388091 | SEQ ID NO: 32 |
| TAGTSFMMT[+80.0]PY[+80.0]VVTR | JNK1 (T183/Y185), JNK3 (T221/Y223) | sp\|P45983\|MK08_HUMAN, sp\|P53779\|MK10_HUMAN | +2 | 911,371257 | SEQ ID NO: 33 |
| TAGTSFM[+16.0]M[+16.0]T[+80.0]PY[+80.0]VVTR | JNK1 (T183/Y185), JNK3 (T221/Y223) | sp\|P45983\|MK08_HUMAN, sp\|P53779\|MK10_HUMAN | +2 | 927,366172 | SEQ ID NO: 34 |
| TAGTSFM[+16.0]M[+16.0]T[+80.0]PYVVTR | JNK1 (T183), JNK3 (T221) | sp\|P45983\|MK08_HUMAN, sp\|P53779\|MK10_HUMAN | +2 | 887,383006 | SEQ ID NO: 35 |
| TAGTSFMMTPY[+80.0]VVTR | JNK1 (Y185), JNK3 (Y223) | sp\|P45983\|MK08_HUMAN, sp\|P53779\|MK10_HUMAN | +2 | 871,388091 | SEQ ID NO: 36 |
| TAGTSFM[+16.0]M[+16.0]TPY[+80.0]VVTR | JNK1 (Y185), JNK3 (Y223) | sp\|P45983\|MK08_HUMAN, sp\|P53779\|MK10_HUMAN | +2 | 887,383006 | SEQ ID NO: 37 |
| VLEDDPEAAY[+80.0]TTR | EphA3 (Y779), EphA4 (Y779), EphA5 (Y833) | sp\|P29320\|EPHA3_HUMAN, sp\|P54764\|EPHA4_HUMAN, sp\|P54756\|EPHA5_HUMAN | +2 | 780,334893 | SEQ ID NO: 38 |

FIG. 6B

| Modified Peptide Sequence | Common Kinase Name and Phosphosite Localization | Uniprot ID and Name | Precursor Ion Charge | Precursor Ion m/z | SEQ ID |
|---|---|---|---|---|---|
| MS[+80.0]AAGTYAWMAPEVIR | M3K10 (S262), M3K9 (S308) | sp\|Q02779\|M3K10_HUMAN, sp\|P80192\|M3K9_HUMAN | +2 | 917.406815 | SEQ ID NO: 39 |
| MSAAGT[+80.0]YAWMAPEVIR | M3K10 (T266), M3K9 (T312) | sp\|Q02779\|M3K10_HUMAN, sp\|P80192\|M3K9_HUMAN | +2 | 917.406815 | SEQ ID NO: 40 |
| TYT[+80.0]HEVVTLWYR | CDK2 (T160), CDK3 (T160) | sp\|P24941\|CDK2_HUMAN, sp\|Q00526\|CDK3_HUMAN | +3 | 549.923746 | SEQ ID NO: 41 |
| STMVGT[+80.0]PYWMAPEVVTR | PAK1 (T427), PAK2 (T406), PAK3 (T440) | sp\|Q13153\|PAK1_HUMAN, sp\|Q13177\|PAK2_HUMAN, sp\|O75914\|PAK3_HUMAN | +2 | 1002.951587 | SEQ ID NO: 42 |
| GAILT[+80.0]TMLATR | KCC2A (T305), KCC2B (T306), KCC2D (T306) | sp\|Q9UQM7\|KCC2A_HUMAN, sp\|Q13554\|KCC2B_HUMAN, sp\|Q13557\|KCC2D_HUMAN | +2 | 614.311981 | SEQ ID NO: 43 |
| GAILT[+80.0]T[+80.0]MLATR | KCC2A (T305/T306), KCC2B (T306/T307), KCC2D (T306/T307) | sp\|Q9UQM7\|KCC2A_HUMAN, sp\|Q13554\|KCC2B_HUMAN, sp\|Q13557\|KCC2D_HUMAN | +2 | 654.295147 | SEQ ID NO: 44 |
| GAILT[+80.0]T[+80.0]M[+16.0]LATR | KCC2A (T305/T306), KCC2B (T306/T307), KCC2D (T306/T307) | sp\|Q9UQM7\|KCC2A_HUMAN, sp\|Q13554\|KCC2B_HUMAN, sp\|Q13557\|KCC2D_HUMAN | +2 | 662.292604 | SEQ ID NO: 45 |
| GAILT[+80.0]TM[+16.0]LATR | KCC2A (T305), KCC2B (T306), KCC2D (T306) | sp\|Q9UQM7\|KCC2A_HUMAN, sp\|Q13554\|KCC2B_HUMAN, sp\|Q13557\|KCC2D_HUMAN | +2 | 622.309439 | SEQ ID NO: 46 |
| GAILTT[+80.0]MLATR | KCC2A (T306), KCC2B (T307), KCC2D T307) | sp\|Q9UQM7\|KCC2A_HUMAN, sp\|Q13554\|KCC2B_HUMAN, sp\|Q13557\|KCC2D_HUMAN | +2 | 614.311981 | SEQ ID NO: 47 |
| GAILTT[+80.0]M[+16.0]LATR | KCC2A (T306), KCC2B (T307), KCC2D T307) | sp\|Q9UQM7\|KCC2A_HUMAN, sp\|Q13554\|KCC2B_HUMAN, sp\|Q13557\|KCC2D_HUMAN | +2 | 622.309439 | SEQ ID NO: 48 |
| DVY[+80.0]STDYYR | TrkB (Y702), TrkC (Y705) | sp\|Q16620\|NTRK2_HUMAN, sp\|Q16288\|NTRK3_HUMAN | +2 | 631.242276 | SEQ ID NO: 49 |
| DVYSTDY[+80.0]YR | TrkB (Y706), TrkC (Y709) | sp\|Q16620\|NTRK2_HUMAN, sp\|Q16288\|NTRK3_HUMAN | +2 | 631.242276 | SEQ ID NO: 50 |
| DVYSTDYY[+80.0]R | TrkB (Y707), TrkC (Y710) | sp\|Q16620\|NTRK2_HUMAN, sp\|Q16288\|NTRK3_HUMAN | +2 | 631.242276 | SEQ ID NO: 51 |
| Y[+80.0]TC[+57.0]QIK | TTN (Y8490), [TBRG1 (Y234)] | sp\|Q3YBR2\|TBRG1_HUMAN, sp\|Q3YBR2\|TBRG1_HUMAN | +2 | 446.685354 | SEQ ID NO: 52 |
| LADFGS[+80.0]C[+57.0]LK | DMPK (S216), MRCKA (S222), MRCKB (S221) | sp\|Q09013\|DMPK_HUMAN, sp\|Q5VT25\|MRCKA_HUMAN, sp\|Q9Y5S2\|MRCKB_HUMAN | +2 | 545.735575 | SEQ ID NO: 53 |
| ANS[+80.0]FVGTAQYVSPELLTEK | PDK1 (S241), PDK2 (S241) | sp\|O15530\|PDPK1_HUMAN, sp\|Q6A1A2\|PDPK2_HUMAN | +3 | 712.008315 | SEQ ID NO: 54 |
| LDT[+80.0]FC[+57.0]GSPPYAAPELFQGK | MARK1 (T215), MARK2 (T208), MARK3 (T211), MARK4 (T214) | sp\|Q9P0L2\|MARK1_HUMAN, sp\|Q7KZI7\|MARK2_HUMAN, | +3 | 726.658629 | SEQ ID NO: 55 |

FIG. 6C

| Modified Peptide Sequence | Common Kinase Name and Phosphosite Localization | Uniprot ID and Name | Precursor Ion Charge | Precursor Ion m/z | SEQ ID |
|---|---|---|---|---|---|
| | | sp\|P27448\|MARK3_HUMAN, sp\|Q96L34\|MARK4_HUMAN | | | |
| LDT[+80.0]FC[+57.0]GS[+80.0]PPYAAPELFQGK | MARK1 (T215/S219), MARK2 (T208/S212), MARK3 (T211/S215), MARK4 (T214/S218) | sp\|Q9P0L2\|MARK1_HUMAN, sp\|Q7KZI7\|MARK2_HUMAN, sp\|P27448\|MARK3_HUMAN, sp\|Q96L34\|MARK4_HUMAN | +3 | 753.314073 | SEQ ID NO: 56 |
| LDTFC[+57.0]GS[+80.0]PPYAAPELFQGK | MARK1 (S219), MARK2 (S212), MARK3 (S215), MARK4 (S218) | sp\|Q9P0L2\|MARK1_HUMAN, sp\|Q7KZI7\|MARK2_HUMAN, sp\|P27448\|MARK3_HUMAN, sp\|Q96L34\|MARK4_HUMAN | +3 | 726.658629 | SEQ ID NO: 57 |
| DY[+80.0]YVVR | JAK3 (Y980), PKR2 (Y113), PKR1 (Y122) | sp\|P52333\|JAK3_HUMAN, sp\|Q8TCW9\|PKR1_HUMAN, sp\|Q8NFJ6\|PKR2_HUMAN | +2 | 447.691493 | SEQ ID NO: 58 |
| DY[+80.0]Y[+80.0]VVR | JAK3 (Y980/Y981), PKR2 (Y113/Y114), PKR1 (Y122/Y123) | sp\|P52333\|JAK3_HUMAN, sp\|Q8TCW9\|PKR1_HUMAN, sp\|Q8NFJ6\|PKR2_HUMAN | +2 | 487.674659 | SEQ ID NO: 59 |
| DYY[+80.0]VVR | JAK3 (Y981), PKR2 (Y114), PKR1 (Y123) | sp\|P52333\|JAK3_HUMAN, sp\|Q8TCW9\|PKR1_HUMAN, sp\|Q8NFJ6\|PKR2_HUMAN | +2 | 447.691493 | SEQ ID NO: 60 |
| VYT[+80.0]YIQSR | DYRK2 (Y382), DYRK4 (Y264) | sp\|Q92630\|DYRK2_HUMAN, sp\|Q9NR20\|DYRK4_HUMAN | +2 | 555.254989 | SEQ ID NO: 61 |
| VYT[+80.0]Y[+80.0]IQSR | DYRK2 (T381/Y382), DYRK4 (T263/Y264) | sp\|Q92630\|DYRK2_HUMAN, sp\|Q9NR20\|DYRK4_HUMAN | +2 | 595.238155 | SEQ ID NO: 62 |
| VYTY[+80.0]IQSR | DYRK2 (Y382), DYRK4 (Y264) | sp\|Q92630\|DYRK2_HUMAN, sp\|Q9NR20\|DYRK4_HUMAN | +2 | 555.254989 | SEQ ID NO: 63 |
| S[+80.0]LVGTPYWMAPEVISR | PAK6 (S560), PAK7 (S602) | sp\|Q9NQU5\|PAK6_HUMAN, sp\|Q9P286\|PAK7_HUMAN | +2 | 943.449537 | SEQ ID NO: 64 |
| S[+80.0]LVGTPYWM[+16.0]APEVISR | PAK6 (S560), PAK7 (S602) | sp\|Q9NQU5\|PAK6_HUMAN, sp\|Q9P286\|PAK7_HUMAN | +2 | 951.446995 | SEQ ID NO: 65 |
| IVDFGS[+80.0]SC[+57.0]QLGQR | Dyr1A (S310), Dyr1B (S262) | sp\|Q13627\|DYR1A_HUMAN, sp\|Q9Y463\|DYR1B_HUMAN | +2 | 773.839623 | SEQ ID NO: 66 |
| IY[+80.0]QY[+80.0]IQSR | Dyr1A (Y319/Y321), Dyr1B (Y271/Y273) | sp\|Q13627\|DYR1A_HUMAN, sp\|Q9Y463\|DYR1B_HUMAN | +2 | 615.751429 | SEQ ID NO: 67 |
| IYQY[+80.0]IQSR | Dyr1A (Y321), Dyr1B Y273) | sp\|Q13627\|DYR1A_HUMAN, sp\|Q9Y463\|DYR1B_HUMAN | +2 | 575.768264 | SEQ ID NO: 68 |
| AFS[+80.0]LAK | CDK9 (S175) | sp\|P50750\|CDK9_HUMAN | +2 | 358.672572 | SEQ ID NO: 69 |
| ALGADDSY[+80.0]YTAR | ZAP70 (Y492) | sp\|P43403\|ZAP70_HUMAN | +2 | 691.784839 | SEQ ID NO: 70 |
| APEMVNLY[+80.0]SGK | AAK1 (Y234) | sp\|Q2M2I8\|AAK1_HUMAN | +2 | 644.785796 | SEQ ID NO: 71 |
| APEMVNLY[+80.0]S[+80.0]GK | AAK1 (Y234/S235) | sp\|Q2M2I8\|AAK1_HUMAN | +2 | 684.768962 | SEQ ID NO: 72 |

FIG. 6D

| Modified Peptide Sequence | Common Kinase Name and Phosphosite Localization | Uniprot ID and Name | Precursor Ion Charge | Precursor Ion m/z | SEQ ID |
|---|---|---|---|---|---|
| APEM[+16.0]VNLY[+80.0]S[+80.0]GK | AAK1 (Y234/S235) | sp\|Q2M2I8\|AAK1_HUMAN | +2 | 692.766419 | SEQ ID NO: 73 |
| APEM[+16.0]VNLY[+80.0]SGK | AAK1 (Y234) | sp\|Q2M2I8\|AAK1_HUMAN | +2 | 652.783254 | SEQ ID NO: 74 |
| APEMVNLYS[+80.0]GK | AAK1 (S235) | sp\|Q2M2I8\|AAK1_HUMAN | +2 | 644.785796 | SEQ ID NO: 75 |
| APEM[+16.0]VNLYS[+80.0]GK | AAK1 (S235) | sp\|Q2M2I8\|AAK1_HUMAN | +2 | 652.783254 | SEQ ID NO: 76 |
| ATDS[+80.0]FSGR | MNK2 (S74) | sp\|Q9HBH9\|MKNK2_HUMAN | +2 | 460.679114 | SEQ ID NO: 77 |
| AVPEGHEY[+80.0]YR | TYK2 (1054) | sp\|P29597\|TYK2_HUMAN | +2 | 650.771535 | SEQ ID NO: 78 |
| AY[+80.0]TPVVVTLWYR | CDK11B (Y594) | sp\|P21127\|CD11B_HUMAN | +2 | 774.386535 | SEQ ID NO: 79 |
| AY[+80.0]T[+80.0]PVVVTLWYR | CDK11B (Y594/T595) | sp\|P21127\|CD11B_HUMAN | +2 | 814.3697 | SEQ ID NO: 80 |
| AYT[+80.0]PVVVTLWYR | CDK11B (T595) | sp\|P21127\|CD11B_HUMAN | +2 | 774.386535 | SEQ ID NO: 81 |
| AYS[+80.0]FC[+57.0]GTIEYMAPDIVR | MSK1 (S212) | sp\|O75582\|KS6A5_HUMAN | +2 | 1036.946502 | SEQ ID NO: 82 |
| AYS[+80.0]FC[+57.0]GTIEYM[+16.0]APDIVR | MSK1 (S212) | sp\|O75582\|KS6A5_HUMAN | +2 | 1044.943959 | SEQ ID NO: 83 |
| DDEY[+80.0]NPC[+57.0]QGSK | FGR (412) | sp\|P09769\|FGR_HUMAN | +2 | 696.742314 | SEQ ID NO: 84 |
| DDIY[+80.0]SPSSSSK | SRMS (Y849) | sp\|Q9H3Y6\|SRMS_HUMAN | +2 | 633.250298 | SEQ ID NO: 85 |
| DIM[+16.0]HDSNY[+80.0]VSK | PGFRA (Y849) | sp\|P16234\|PGFRA_HUMAN | +2 | 694.781242 | SEQ ID NO: 86 |
| DIM[+16.0]HDSNY[+80.0]VSK | PGFRA (Y849) | sp\|P16234\|PGFRA_HUMAN | +2 | 702.7787 | SEQ ID NO: 87 |
| DIHHIDY[+80.0]YK | FGFR1 (Y653) | sp\|P11362\|FGFR1_HUMAN | +3 | 428.520061 | SEQ ID NO: 88 |
| DIHHIDYY[+80.0]K | FGFR1 (Y654) | sp\|P11362\|FGFR1_HUMAN | +3 | 428.520061 | SEQ ID NO: 89 |
| DIMNDSNY[+80.0]IVK | CSF1R (Y809) | sp\|P07333\|CSF1R_HUMAN | +2 | 696.299268 | SEQ ID NO: 90 |
| DIM[+16.0]NDSNY[+80.0]IVK | CSF1R (Y809) | sp\|P07333\|CSF1R_HUMAN | +2 | 704.296725 | SEQ ID NO: 91 |
| DIMSDSNY[+80.0]VVR | FLT3 (Y842) | sp\|P36888\|FLT3_HUMAN | +2 | 689.789067 | SEQ ID NO: 92 |
| DIM[+16.0]SDSNY[+80.0]VVR | FLT3 (Y842) | sp\|P36888\|FLT3_HUMAN | +2 | 697.786525 | SEQ ID NO: 93 |

FIG. 6E

| Modified Peptide Sequence | Common Kinase Name and Phosphosite Localization | Uniprot ID and Name | Precursor Ion Charge | Precursor Ion m/z | SEQ ID |
|---|---|---|---|---|---|
| DINNIDY[+80.0]YK | FGFR2 (Y656) | sp\|P21802\|FGFR2_HUMAN | +2 | 619.260468 | SEQ ID NO: 94 |
| DINNIDY[+80.0]Y[+80.0]K | FGFR2 (Y656/Y657) | sp\|P21802\|FGFR2_HUMAN | +2 | 659.243634 | SEQ ID NO: 95 |
| DINNIDYY[+80.0]K | FGFR2 (Y657) | sp\|P21802\|FGFR2_HUMAN | +2 | 619.260468 | SEQ ID NO: 96 |
| DIY[+80.0]STDYYR | TrkA (Y676) | sp\|P04629\|NTRK1_HUMAN | +2 | 638.250101 | SEQ ID NO: 97 |
| DIYSTDY[+80.0]YR | TrkA (Y680) | sp\|P04629\|NTRK1_HUMAN | +2 | 638.250101 | SEQ ID NO: 98 |
| DIYSTDYY[+80.0]R | TrkA (Y681) | sp\|P04629\|NTRK1_HUMAN | +2 | 638.250101 | SEQ ID NO: 99 |
| DSNY[+80.0]ISK | PDGFRβ (Y857) | sp\|P09619\|PGFRB_HUMAN | +2 | 453.683865 | SEQ ID NO: 100 |
| DVHNLDY[+80.0]YK | FGFR3 (Y647) | sp\|P22607\|FGFR3_HUMAN | +2 | 623.760636 | SEQ ID NO: 101 |
| DVHNLDY[+80.0]Y[+80.0]K | FGFR3 (Y647/Y648) | sp\|P22607\|FGFR3_HUMAN | +2 | 663.743801 | SEQ ID NO: 102 |
| DVY[+80.0]EEDSYVK | RET (Y900) | sp\|P07949\|RET_HUMAN | +2 | 663.760498 | SEQ ID NO: 103 |
| DVY[+80.0]EEDSY[+80.0]VK | RET (Y900/Y905) | sp\|P07949\|RET_HUMAN | +2 | 703.743664 | SEQ ID NO: 104 |
| DVYEEDSY[+80.0]VK | RET (Y905) | sp\|P07949\|RET_HUMAN | +2 | 663.760498 | SEQ ID NO: 105 |
| DVYETDY[+80.0]R | IRR (Y1145) | sp\|P14616\|INSRR_HUMAN | +2 | 652.247558 | SEQ ID NO: 106 |
| DVYETDY[+80.0]Y[+80.0]R | IRR (Y1145/Y1146) | sp\|P14616\|INSRR_HUMAN | +2 | 692.230724 | SEQ ID NO: 107 |
| DVYETDYY[+80.0]R | IRR (Y1146) | sp\|P14616\|INSRR_HUMAN | +2 | 652.247558 | SEQ ID NO: 108 |
| EDVY[+80.0]LSHDHNIPYK | PTK6 (Y342) | sp\|Q13882\|PTK6_HUMAN | +3 | 603.93297 | SEQ ID NO: 109 |
| EDVY[+80.0]LSHDHNIPY[+80.0]K | PTK6 (Y342/Y351) | sp\|Q13882\|PTK6_HUMAN | +3 | 630.588413 | SEQ ID NO: 110 |
| EDVYLSHDHNIPY[+80.0]K | PTK6 (Y351) | sp\|Q13882\|PTK6_HUMAN | +3 | 603.93297 | SEQ ID NO: 111 |
| EEADGVY[+80.0]AASGGLR | FES (Y713) | sp\|P07332\|FES_HUMAN | +2 | 737.814128 | SEQ ID NO: 112 |
| EIYSADY[+80.0]YR | ROR1 (Y645) | sp\|Q01973\|ROR1_HUMAN | +2 | 630.252643 | SEQ ID NO: 113 |
| ENIFGES[+80.0]R | KPCD (S503) | sp\|Q05655\|KPCD_HUMAN | +2 | 516.213321 | SEQ ID NO: 114 |

FIG. 6F

| Modified Peptide Sequence | Common Kinase Name and Phosphosite Localization | Uniprot ID and Name | Precursor Ion Charge | Precursor Ion m/z | SEQ ID |
|---|---|---|---|---|---|
| EPLAVVGS[+80.0]PYWMAPEVLR | TESK1 (S220) | sp\|Q15569\|TESK1_HUMAN | +2 | 1047,510126 | SEQ ID NO: 115 |
| EPLAVVGS[+80.0]PYWM[+16.0]APEVLR | TESK1 (S220) | sp\|Q15569\|TESK1_HUMAN | +2 | 1055,507584 | SEQ ID NO: 116 |
| EVYAADYY[+80.0]JK | ROR2 (Y646) | sp\|Q01974\|ROR2_HUMAN | +2 | 601,244287 | SEQ ID NO: 117 |
| AY[+80.0]TPVVVTQWYR | CDK11A (Y582) | sp\|Q9UQ88\|CD11A_HUMAN | +2 | 781,873791 | SEQ ID NO: 118 |
| AY[+80.0]T[+80.0]PVVVTQWYR | CDK11A (Y582/T583) | sp\|Q9UQ88\|CD11A_HUMAN | +2 | 821,856957 | SEQ ID NO: 119 |
| EY[+80.0]YSVHNK | MET (Y1234) | sp\|P08581\|MET_HUMAN | +2 | 560,228971 | SEQ ID NO: 120 |
| EY[+80.0]Y[+80.0]SVHNK | MET (Y1234/Y1235) | sp\|P08581\|MET_HUMAN | +2 | 600,212137 | SEQ ID NO: 121 |
| EYY[+80.0]SVHNK | MET (Y1235) | sp\|P08581\|MET_HUMAN | +2 | 560,228971 | SEQ ID NO: 122 |
| EY[+80.0]YSVQQHR | RON (Y1238) | sp\|Q04912\|RON_HUMAN | +2 | 645,269159 | SEQ ID NO: 123 |
| EY[+80.0]Y[+80.0]SVQQHR | RON (Y1238/Y1239) | sp\|Q04912\|RON_HUMAN | +2 | 685,252325 | SEQ ID NO: 124 |
| EYY[+80.0]SVQQHR | RON (Y1239) | sp\|Q04912\|RON_HUMAN | +2 | 645,269159 | SEQ ID NO: 125 |
| EY[+80.0]YTVK | JAK1 (Y1034) | sp\|P23458\|JAK1_HUMAN | +2 | 441,685877 | SEQ ID NO: 126 |
| EYY[+80.0]TVK | JAK1 (Y1035) | sp\|P23458\|JAK1_HUMAN | +2 | 441,685877 | SEQ ID NO: 127 |
| EY[+80.0]Y[+80.0]TVK | JAK1 (Y1034/Y1035) | sp\|P23458\|JAK1_HUMAN | +2 | 481,669042 | SEQ ID NO: 128 |
| EYY[+80.0]TVK | JAK1 (Y1035) | sp\|P23458\|JAK1_HUMAN | +2 | 441,685877 | SEQ ID NO: 129 |
| FAQTVMT[+80.0]SR | IRAK4 (T345) | sp\|Q9NWZ3\|IRAK4_HUMAN | +2 | 560,746474 | SEQ ID NO: 130 |
| FAQTVM[+16.0]T[+80.0]SR | IRAK4 (T345) | sp\|Q9NWZ3\|IRAK4_HUMAN | +2 | 568,743932 | SEQ ID NO: 131 |
| FAQTVMTS[+80.0]R | IRAK4 (S346) | sp\|Q9NWZ3\|IRAK4_HUMAN | +2 | 560,746474 | SEQ ID NO: 132 |
| FAQTVM[+16.0]TS[+80.0]R | IRAK4 (S346) | sp\|Q9NWZ3\|IRAK4_HUMAN | +2 | 568,743932 | SEQ ID NO: 133 |
| FFSSETT[+80.0]AAHSLVGTPYYMSPER | NEK6 (T202) | sp\|Q9HC98\|NEK6_HUMAN | +3 | 886,72425 | SEQ ID NO: 134 |
| FFSSETT[+80.0]AAHSLVGTPYYM[+16.0]SPER | NEK6 (T202) | sp\|Q9HC98\|NEK6_HUMAN | +3 | 892,055888 | SEQ ID NO: 135 |

FIG. 6G

| Modified Peptide Sequence | Common Kinase Name and Phosphosite Localization | Uniprot ID and Name | Precursor Ion Charge | Precursor Ion m/z | SEQ ID |
|---|---|---|---|---|---|
| FFSSETTAAHS[+80.0]LVGTPYYMSPER | NEK6 (S206) | sp\|Q9HC98\|NEK6_HUMAN | +3 | 886,72425 | SEQ ID NO: 136 |
| FFSSETTAAHS[+80.0]LVGTPYYM[+16.0]SPER | NEK6 (S206) | sp\|Q9HC98\|NEK6_HUMAN | +3 | 892,055888 | SEQ ID NO: 137 |
| FVLDDQY[+80.0]TSSTGTK | ITK (Y512) | sp\|Q08881\|ITK_HUMAN | +2 | 821,355826 | SEQ ID NO: 138 |
| FVS[+80.0]VYGTEEYLHPDMYER | IKKE (S172) | sp\|Q14164\|IKKE_HUMAN | +3 | 772,32906 | SEQ ID NO: 139 |
| FVS[+80.0]VYGTEEYLHPDM[+16.0]YER | IKKE (S172) | sp\|Q14164\|IKKE_HUMAN | +3 | 777,660698 | SEQ ID NO: 140 |
| GDVMST[+80.0]AC[+57.0]GTPGYVAPEVLAQK | KCC1D (T180) | sp\|Q8IU85\|KCC1D_HUMAN | +3 | 777,684738 | SEQ ID NO: 141 |
| GDVM[+16.0]ST[+80.0]AC[+57.0]GTPGYVAPEVLAQK | KCC1D (T180) | sp\|Q8IU85\|KCC1D_HUMAN | +3 | 783,016376 | SEQ ID NO: 142 |
| GHLS[+80.0]EGLVTK | MK06 (S189) | sp\|Q16659\|MK06_HUMAN | +2 | 560,773546 | SEQ ID NO: 143 |
| GS[+80.0]AAWMAPEVFEGSNYSEK | M3K7 (S192) | sp\|O43318\|M3K7_HUMAN | +2 | 1070,440095 | SEQ ID NO: 144 |
| GQEVY[+80.0]VK | TIE2 (Y992) | sp\|Q02763\|TIE2_HUMAN | +2 | 451,704601 | SEQ ID NO: 145 |
| GS[+80.0]AAWM[+16.0]APEVFEGSNYSEK | M3K7 (S192) | sp\|O43318\|M3K7_HUMAN | +2 | 1078,437552 | SEQ ID NO: 146 |
| GS[+80.0]FDGSSSQPSR | RK (S21) | sp\|Q15835\|RK_HUMAN | +2 | 646,251163 | SEQ ID NO: 147 |
| GS[+80.0]PLYMAPEMVC[+57.0]QR | ULK3 (S176) | sp\|Q6PHR2\|ULK3_HUMAN | +2 | 859,858644 | SEQ ID NO: 148 |
| GS[+80.0]PLYM[+16.0]APEM[+16.0]VC[+57.0]QR | ULK3 (S176) | sp\|Q6PHR2\|ULK3_HUMAN | +2 | 875,853559 | SEQ ID NO: 149 |
| GT[+80.0]E\|YMSPEVILC[+57.0]R | M3K8 (T290) | sp\|P41279\|M3K8_HUMAN | +2 | 874,393374 | SEQ ID NO: 150 |
| GT[+80.0]E\|YM[+16.0]SPEVILC[+57.0]R | M3K8 (T290) | sp\|P41279\|M3K8_HUMAN | +2 | 882,390831 | SEQ ID NO: 151 |
| GT[+80.0]LAYLPEEYIK | IRAK1 (T387) | sp\|P51617\|IRAK1_HUMAN | +2 | 738,854733 | SEQ ID NO: 152 |
| GVHHIDY[+80.0]YK | FGFR4 (Y642) | sp\|P22455\|FGFR4_HUMAN | +3 | 404,513017 | SEQ ID NO: 153 |
| GVHHIDY[+80.0]Y[+80.0]K | FGFR4 (Y642/Y643) | sp\|P22455\|FGFR4_HUMAN | +3 | 431,168461 | SEQ ID NO: 154 |
| GVHHIDYY[+80.0]K | FGFR4 (Y643) | sp\|P22455\|FGFR4_HUMAN | +3 | 404,513017 | SEQ ID NO: 155 |
| GYLS[+80.0]EGLVTK | MK04 (S186) | sp\|P31152\|MK04_HUMAN | +2 | 573,775754 | SEQ ID NO: 156 |

FIG. 6H

| Modified Peptide Sequence | Common Kinase Name and Phosphosite Localization | Uniprot ID and Name | Precursor Ion Charge | Precursor Ion m/z | SEQ ID |
|---|---|---|---|---|---|
| HADAEMT[+80.0]GYVVTR | P38δ (T180) | sp\|O15264\|MK13_HUMAN | +2 | 765,326348 | SEQ ID NO: 157 |
| HADAEMT[+80.0]GY[+80.0]VVTR | P38δ (T180/Y182) | sp\|O15264\|MK13_HUMAN | +2 | 805,309514 | SEQ ID NO: 158 |
| HADAEM[+16.0]T[+80.0]GY[+80.0]VVTR | P38δ (T180/Y182) | sp\|O15264\|MK13_HUMAN | +2 | 813,306971 | SEQ ID NO: 159 |
| HADAEM[+16.0]T[+80.0]GYVVTR | P38δ (T180) | sp\|O15264\|MK13_HUMAN | +2 | 773,323806 | SEQ ID NO: 160 |
| HADAEMTGY[+80.0]VVTR | P38δ (Y182) | sp\|O15264\|MK13_HUMAN | +2 | 765,326348 | SEQ ID NO: 161 |
| HADAEM[+16.0]TGY[+80.0]VVTR | P38δ (Y182) | sp\|O15264\|MK13_HUMAN | +2 | 773,323806 | SEQ ID NO: 162 |
| HMT[+80.0]QEVVTQYYR | NLK (T298) | sp\|Q9UBE8\|NLK_HUMAN | +3 | 545,572607 | SEQ ID NO: 163 |
| HM[+16.0]T[+80.0]QEVVTQYYR | NLK (T298) | sp\|Q9UBE8\|NLK_HUMAN | +3 | 550,904246 | SEQ ID NO: 164 |
| HTDDEMT[+80.0]GYVATR | MK14 (T180) | sp\|Q16539\|MK14_HUMAN | +3 | 525,876355 | SEQ ID NO: 165 |
| HTDDEMT[+80.0]GY[+80.0]VATR | MK14 (T180/Y182) | sp\|Q16539\|MK14_HUMAN | +3 | 552,531799 | SEQ ID NO: 166 |
| HTDDEM[+16.0]T[+80.0]GY[+80.0]VATR | MK14 (T180/Y182) | sp\|Q16539\|MK14_HUMAN | +2 | 836,291518 | SEQ ID NO: 167 |
| HTDDEM[+16.0]T[+80.0]GYVATR | MK14 (T180) | sp\|Q16539\|MK14_HUMAN | +2 | 796,308353 | SEQ ID NO: 168 |
| HTDDEMTGY[+80.0]VATR | MK14 (Y182) | sp\|Q16539\|MK14_HUMAN | +3 | 525,876355 | SEQ ID NO: 169 |
| HTDDEM[+16.0]TGY[+80.0]VATR | MK14 (Y182) | sp\|Q16539\|MK14_HUMAN | +2 | 796,308353 | SEQ ID NO: 170 |
| IADLGLAS[+80.0]FK | RIPK1 (S161) | sp\|Q13546\|RIPK1_HUMAN | +2 | 557,78084 | SEQ ID NO: 171 |
| IADPEHDHT[+80.0]GFLTEYVATR | ERK1 (T198) | sp\|P27361\|MK03_HUMAN | +3 | 751,338835 | SEQ ID NO: 172 |
| IADPEHDHTGFLT[+80.0]EYVATR | ERK1 (T202) | sp\|P27361\|MK03_HUMAN | +3 | 751,338835 | SEQ ID NO: 173 |
| IADPEHDHTGFLTEY[+80.0]VATR | ERK1 (Y204) | sp\|P27361\|MK03_HUMAN | +3 | 751,338835 | SEQ ID NO: 174 |
| IC[+57.0]DFGAS[+80.0]R | MLTK (S155) | sp\|Q9NYL2\|MLTK_HUMAN | +2 | 503,196617 | SEQ ID NO: 175 |
| IDQGDLMT[+80.0]PQFTPYYVAPQVLEAQR | MAPK5 (T182) | sp\|Q8IW41\|MAPK5_HUMAN | +3 | 987,46818 | SEQ ID NO: 176 |
| IDQGDLM[+16.0]T[+80.0]PQFTPYYVAPQVLEAQR | MAPK5 (T182) | sp\|Q8IW41\|MAPK5_HUMAN | +3 | 992,799818 | SEQ ID NO: 177 |

FIG. 6I

| Modified Peptide Sequence | Common Kinase Name and Phosphosite Localization | Uniprot ID and Name | Precursor Ion Charge | Precursor Ion m/z | SEQ ID |
|---|---|---|---|---|---|
| IIDSEY[+80.0]TAQEGAK | BLK (Y389) | sp\|P51451\|BLK_HUMAN | +2 | 752.831986 | SEQ ID NO: 178 |
| IYNGDYY[+80.0]R | UFO (Y703) | sp\|P30530\|UFO_HUMAN | +2 | 572.228871 | SEQ ID NO: 179 |
| IY[+80.0]SGDYYR | MERTK (Y749) TYRO3 (Y681) | sp\|Q12866\|MERTK_HUMAN, sp\|Q06418\|TYRO3_HUMAN | +2 | 558.723522 | SEQ ID NO: 180 |
| IYSGDY[+80.0]YR | MERTK (Y753) TYRO3 (Y685) | sp\|Q12866\|MERTK_HUMAN, sp\|Q06418\|TYRO3_HUMAN | +2 | 558.723522 | SEQ ID NO: 181 |
| IYSGDYY[+80.0]R | MERTK (Y754) TYRO3 (Y686) | sp\|Q12866\|MERTK_HUMAN, sp\|Q06418\|TYRO3_HUMAN | +2 | 558.723522 | SEQ ID NO: 182 |
| LAVVGS[+80.0]PFWMAPEVLR | TESK2 (S219) | sp\|Q96S53\|TESK2_HUMAN | +2 | 926.46499 | SEQ ID NO: 183 |
| LAVVGS[+80.0]PFWM[+16.0]APEVLR | TESK2 (S219) | sp\|Q96S53\|TESK2_HUMAN | +2 | 934.462448 | SEQ ID NO: 184 |
| LC[+57.0]DFGISGQLVDS[+80.0]IAK | MKK4 (S2570) | sp\|P45985\|MP2K4_HUMAN | +2 | 901.923353 | SEQ ID NO: 185 |
| LADFGS[+80.0]C[+57.0]LR | MRCKG (S216) | sp\|Q6DT37\|MRCKG_HUMAN | +2 | 559.738849 | SEQ ID NO: 186 |
| IADFGFSNEFT[+80.0]VGNK | MARK1 (T208) | sp\|Q9P0L2\|MARK1_HUMAN | +2 | 863.379635 | SEQ ID NO: 187 |
| LYTY[+80.0]QSR | Dyrk3 (Y369) | sp\|O43781\|DYRK3_HUMAN | +2 | 562.262814 | SEQ ID NO: 188 |
| MMSLS[+80.0]QSR | RIPK2 (S176) | sp\|O43353\|RIPK2_HUMAN | +2 | 510.206127 | SEQ ID NO: 189 |
| M[+16.0]M[+16.0]SLS[+80.0]QSR | RIPK2 (S176) | sp\|O43353\|RIPK2_HUMAN | +2 | 526.201042 | SEQ ID NO: 190 |
| MS[+80.0]TAGTYAWMAPEVIK | M3KL4 (S303) | sp\|Q5TCX8\|M3KL4_HUMAN | +2 | 918.409024 | SEQ ID NO: 191 |
| M[+16.0]S[+80.0]TAGTYAWM[+16.0]APEVIK | M3KL4 (S303) | sp\|Q5TCX8\|M3KL4_HUMAN | +2 | 934.403939 | SEQ ID NO: 192 |
| NDS[+80.0]NYVVK | KIT (S821) | sp\|P10721\|KIT_HUMAN | +2 | 509.715697 | SEQ ID NO: 193 |
| NDS[+80.0]NY[+80.0]VVK | KIT (S821/Y823) | sp\|P10721\|KIT_HUMAN | +2 | 549.698862 | SEQ ID NO: 194 |
| NDSNY[+80.0]VVK | KIT (Y823) | sp\|P10721\|KIT_HUMAN | +2 | 509.715697 | SEQ ID NO: 195 |
| NIYSADY[+80.0]YK | MUSK (Y755) | sp\|O15146\|MUSK_HUMAN | +2 | 608.749737 | SEQ ID NO: 196 |
| NLY[+80.0]AGDYYR | DDR1 (Y792) | sp\|Q08345\|DDR1_HUMAN | +2 | 607.747528 | SEQ ID NO: 197 |
| NLYAGDY[+80.0]YR | DDR1 (Y796) | sp\|Q08345\|DDR1_HUMAN | +2 | 607.747528 | SEQ ID NO: 198 |

FIG. 6J

| Modified Peptide Sequence | Common Kinase Name and Phosphosite Localization | Uniprot ID and Name | Precursor Ion Charge | Precursor Ion m/z | SEQ ID |
|---|---|---|---|---|---|
| NLYAGDY[+80.0]R | DDR1 (Y797) | sp\|Q08345\|DDR1_HUMAN | +2 | 607.747528 | SEQ ID NO: 199 |
| NLY[+80.0]SGDYYR | DDR2 (Y736) | sp\|Q16832\|DDR2_HUMAN | +2 | 615.744986 | SEQ ID NO: 200 |
| NLYSGDY[+80.0]YR | DDR2 (Y740) | sp\|Q16832\|DDR2_HUMAN | +2 | 615.744986 | SEQ ID NO: 201 |
| NLYSGDYY[+80.0]R | DDR2 (Y741) | sp\|Q16832\|DDR2_HUMAN | +2 | 615.744986 | SEQ ID NO: 202 |
| PGEEDNAAISEVGT[+80.0]R | BMPR2 (T379) | sp\|Q13873\|BMPR2_HUMAN | +2 | 869.388188 | SEQ ID NO: 203 |
| QADEEMT[+80.0]GYVATR | P38B (T180) | sp\|Q15759\|MK11_HUMAN | +2 | 775.813271 | SEQ ID NO: 204 |
| QADEEMT[+80.0]GY[+80.0]VATR | P38B (T180/Y182) | sp\|Q15759\|MK11_HUMAN | +2 | 815.796436 | SEQ ID NO: 205 |
| QADEEM[+16.0]T[+80.0]GY[+80.0]VATR | P38B (T180/Y182) | sp\|Q15759\|MK11_HUMAN | +2 | 823.793894 | SEQ ID NO: 206 |
| QADEEM[+16.0]T[+80.0]GYVATR | P38B (T180) | sp\|Q15759\|MK11_HUMAN | +2 | 783.810728 | SEQ ID NO: 207 |
| QADEEMTGY[+80.0]VATR | P38B (Y182) | sp\|Q15759\|MK11_HUMAN | +2 | 775.813271 | SEQ ID NO: 208 |
| QADEEM[+16.0]TGY[+80.0]VATR | P38B (Y182) | sp\|Q15759\|MK11_HUMAN | +2 | 783.810728 | SEQ ID NO: 209 |
| QADSEMT[+80.0]GYVVTR | P38G (T183) | sp\|P53778\|MK12_HUMAN | +2 | 768.823638 | SEQ ID NO: 210 |
| QADSEMT[+80.0]GY[+80.0]VVTR | P38G (T183/Y185) | sp\|P53778\|MK12_HUMAN | +2 | 808.806804 | SEQ ID NO: 211 |
| QADSEM[+16.0]T[+80.0]GY[+80.0]VVTR | P38G (T183/Y185) | sp\|P53778\|MK12_HUMAN | +3 | 544.871933 | SEQ ID NO: 212 |
| QADSEM[+16.0]T[+80.0]GYVVTR | P38G (T183) | sp\|P53778\|MK12_HUMAN | +3 | 518.216489 | SEQ ID NO: 213 |
| QADSEMTGY[+80.0]VVTR | P38G (Y185) | sp\|P53778\|MK12_HUMAN | +2 | 768.823638 | SEQ ID NO: 214 |
| QADSEM[+16.0]TGY[+80.0]VVTR | P38G (Y185) | sp\|P53778\|MK12_HUMAN | +3 | 518.216489 | SEQ ID NO: 215 |
| QALT[+80.0]LQDWAAQR | MPSK1 (T185) | sp\|O75716\|STK16_HUMAN | +2 | 740.850848 | SEQ ID NO: 216 |
| C[+57.0]T[TIS][+80.0]YR | MPSK1 (S197) | sp\|O75716\|STK16_HUMAN | +2 | 440.175153 | SEQ ID NO: 217 |
| C[+57.0]T[TIS][+80.0]Y[+80.0]R | MPSK1 (S197/Y198) | sp\|O75716\|STK16_HUMAN | +2 | 480.158319 | SEQ ID NO: 218 |
| C[+57.0]T[TISY][+80.0]R | MPSK1 (Y198) | sp\|O75716\|STK16_HUMAN | +2 | 440.175153 | SEQ ID NO: 219 |

FIG. 6K

| Modified Peptide Sequence | Common Kinase Name and Phosphosite Localization | Uniprot ID and Name | Precursor Ion Charge | Precursor Ion m/z | SEQ ID |
|---|---|---|---|---|---|
| QEDGGVY[+80.0]SSSGLK | Fer (Y714) | sp\|P16591\|FER_HUMAN | +2 | 703,795404 | SEQ ID NO: 220 |
| QET[+80.0]VEC[+57.0]LK | CaMKIIβ (T287) | sp\|Q13554\|KCC2B_HUMAN | +2 | 543,73049 | SEQ ID NO: 221 |
| QS[+80.0]GVVVEEPPPSK | CDK12 (S1053) | sp\|Q9NYV4\|CDK12_HUMAN | +2 | 716,839614 | SEQ ID NO: 222 |
| NSS[+80.0]PAPPQPAPGK | CDK12 (S1083) | sp\|Q9NYV4\|CDK12_HUMAN | +2 | 664,305742 | SEQ ID NO: 223 |
| S[+80.0]LVGTPYWMAPELISR | PAK4 (S475) | sp\|O96013\|PAK4_HUMAN | +2 | 950,457362 | SEQ ID NO: 224 |
| S[+80.0]LVGTPYWM[+16.0]APELISR | PAK4 (S475) | sp\|O96013\|PAK4_HUMAN | +2 | 958,45482 | SEQ ID NO: 225 |
| SDPSGHLT[+80.0]GMVGTALYVSPEVQGSTK | GCN2 (T899) | sp\|Q9P2K8\|E2AK4_HUMAN | +3 | 900,085847 | SEQ ID NO: 226 |
| SDPSGHLT[+80.0]GM[+16.0]VGTALYVSPEVQGSTK | GCN2 (T899) | sp\|Q9P2K8\|E2AK4_HUMAN | +3 | 905,417485 | SEQ ID NO: 227 |
| SDPSGHLTGMVGT[+80.0]ALYVSPEVQGSTK | GCN2 (T904) | sp\|Q9P2K8\|E2AK4_HUMAN | +3 | 900,085847 | SEQ ID NO: 228 |
| SDPSGHLTGM[+16.0]VGT[+80.0]ALYVSPEVQGSTK | GCN2 (T904) | sp\|Q9P2K8\|E2AK4_HUMAN | +3 | 905,417485 | SEQ ID NO: 229 |
| SEIGHSPPPAY[+80.0]TPMSGNQFVYR | Her4 (Y1056) | sp\|Q15303\|ERBB4_HUMAN | +3 | 839,041913 | SEQ ID NO: 230 |
| SFGS[+80.0]PNR | CDK7 (S164) | sp\|P50613\|CDK7_HUMAN | +2 | 422,671092 | SEQ ID NO: 231 |
| AYT[+80.0]HQVVTR | CDK7 (T170) | sp\|P50613\|CDK7_HUMAN | +2 | 577,771338 | SEQ ID NO: 232 |
| C[+57.0]LTSNLLQS[+80.0]R | MASTL (S293) | sp\|Q96GX5\|GWL_HUMAN | +2 | 636,29432 | SEQ ID NO: 233 |
| DYLSSS[+80.0]FLC[+57.0]SDDDR | MASTL (S552) | sp\|Q96GX5\|GWL_HUMAN | +2 | 880,329482 | SEQ ID NO: 234 |
| DYLSSS[+80.0]FLC[+57.0]S[+80.0]DDDR | MASTL (S552/S556) | sp\|Q96GX5\|GWL_HUMAN | +2 | 920,312647 | SEQ ID NO: 235 |
| GVENPAVQES[+80.0]NQK | MASTL (S631) | sp\|Q96GX5\|GWL_HUMAN | +2 | 740,327402 | SEQ ID NO: 236 |
| S[+80.0]FNSHINASNNSEPSR | MASTL (S657) | sp\|Q96GX5\|GWL_HUMAN | +3 | 614,258516 | SEQ ID NO: 237 |
| S[+80.0]FNSHINASNNS[+80.0]EPSR | MASTL (S657/S668) | sp\|Q96GX5\|GWL_HUMAN | +3 | 640,913959 | SEQ ID NO: 238 |
| SFNSHINASNNS[+80.0]EPSR | MASTL (S668) | sp\|Q96GX5\|GWL_HUMAN | +3 | 614,258516 | SEQ ID NO: 239 |
| ILGT[+80.0]PDYLAPELLLGR | MASTL (T741) | sp\|Q96GX5\|GWL_HUMAN | +2 | 910,981528 | SEQ ID NO: 240 |

FIG. 6L

| Modified Peptide Sequence | Common Kinase Name and Phosphosite Localization | Uniprot ID and Name | Precursor Ion Charge | Precursor Ion m/z | SEQ ID |
|---|---|---|---|---|---|
| SGEPLST[+80.0]WC[+57.0]GSPPYAAPEVFEGK | SIK (T182) | sp\|P57059\|SIK1_HUMAN | +3 | 849,369695 | SEQ ID NO: 241 |
| S[+80.0]VVGTPAYLAPEVLLNQGYNR | PRKD2 (S710) | sp\|Q9BZL6\|KPCD2_HUMAN | +3 | 781,05778 | SEQ ID NO: 242 |
| SVVGTPAY[+80.0]LAPEVLLNQGYNR | PRKD2 (Y717) | sp\|Q9BZL6\|KPCD2_HUMAN | +3 | 781,05778 | SEQ ID NO: 243 |
| T[+80.0]IC[+57.0]GTPNYLSPEVLNK | PLK2 (T239) | sp\|Q9NYY3\|PLK2_HUMAN | +2 | 943,441909 | SEQ ID NO: 244 |
| ILGETS[+80.0]LMR | Chk2/Rad53 (S379) | sp\|O96017\|CHK2_HUMAN | +2 | 550,2645 | SEQ ID NO: 245 |
| ILGETS[+80.0]LM[+16.0]R | Chk2/Rad53 (S379) | sp\|O96017\|CHK2_HUMAN | +2 | 558,261957 | SEQ ID NO: 246 |
| T[+80.0]VC[+57.0]GTPGYC[+57.0]APEILR | CaMK4 (T200) | sp\|Q16566\|KCC4_HUMAN | +2 | 887,388623 | SEQ ID NO: 247 |
| T[+80.0]YVGTNAYMAPER | MEK5 (T315) | sp\|Q13163\|MP2K5_HUMAN | +2 | 776,828724 | SEQ ID NO: 248 |
| T[+80.0]YVGTNAYM[+16.0]APER | MEK5 (T315) | sp\|Q13163\|MP2K5_HUMAN | +2 | 784,826181 | SEQ ID NO: 249 |
| TAC[+57.0]TNFMMT[+80.0]PYVVTR | JNK2 (T183) | sp\|P45984\|MK09_HUMAN | +2 | 936,398133 | SEQ ID NO: 250 |
| TAC[+57.0]TNFMMT[+80.0]PY[+80.0]VVTR | JNK2 (T183/Y185) | sp\|P45984\|MK09_HUMAN | +3 | 651,256624 | SEQ ID NO: 251 |
| TAC[+57.0]TNFM[+16.0]M[+16.0]T[+80.0]PY[+80.0]VVTR | JNK2 (T183/Y185) | sp\|P45984\|MK09_HUMAN | +3 | 992,376214 | SEQ ID NO: 252 |
| TAC[+57.0]TNFMMTPY[+80.0]VVTR | JNK2 (Y185) | sp\|P45984\|MK09_HUMAN | +2 | 936,398133 | SEQ ID NO: 253 |
| TAC[+57.0]TNFM[+16.0]M[+16.0]TPY[+80.0]VVTR | JNK2 (Y185) | sp\|P45984\|MK09_HUMAN | +2 | 952,393048 | SEQ ID NO: 254 |
| ILNHDT[+80.0]SFAK | NEK2 (T170) | sp\|P51955\|NEK2_HUMAN | +2 | 613,284278 | SEQ ID NO: 255 |
| ILNHDT[+80.0]S[+80.0]FAK | NEK2 (T170/S171) | sp\|P51955\|NEK2_HUMAN | +2 | 653,267443 | SEQ ID NO: 256 |
| ILNHDTS[+80.0]FAK | NEK2 (S171) | sp\|P51955\|NEK2_HUMAN | +2 | 613,284278 | SEQ ID NO: 257 |
| T[+80.0]FVGTPYYMSPEQMNR | NEK2 (T175) | sp\|P51955\|NEK2_HUMAN | +2 | 1000,917744 | SEQ ID NO: 258 |
| TFVGT[+80.0]PYYMSPEQMNR | NEK2 (T179) | sp\|P51955\|NEK2_HUMAN | +2 | 1000,917744 | SEQ ID NO: 259 |
| T[+80.0]LC[+57.0]GTPNYIAPEVLSK | PLK1 (T210) | sp\|P53350\|PLK1_HUMAN | +2 | 921,939003 | SEQ ID NO: 260 |
| T[+80.0]LC[+57.0]GT[+80.0]PNYIAPEVLSK | PLK1 (T210/T214) | sp\|P53350\|PLK1_HUMAN | +2 | 961,922168 | SEQ ID NO: 261 |

FIG. 6M

| Modified Peptide Sequence | Common Kinase Name and Phosphosite Localization | Uniprot ID and Name | Precursor Ion Charge | Precursor Ion m/z | SEQ ID |
|---|---|---|---|---|---|
| TLC[+57.0]GT[+80.0]PNYIAPEVLSK | PLK1 (T214) | sp\|P53350\|PLK1_HUMAN | +2 | 921,939003 | SEQ ID NO: 262 |
| TNT[+80.0]FC[+57.0]GTPDYIAPEILLGQK | PKCθ (T538) | sp\|Q04759\|KPCT_HUMAN | +2 | 1159,542352 | SEQ ID NO: 263 |
| TQTS[+80.0]MSLGTTR | MLKL (S358) | sp\|Q8NB16\|MLKL_HUMAN | +2 | 631,77596 | SEQ ID NO: 264 |
| TQTS[+80.0]M[+16.0]SLGTTR | MLKL (S358) | sp\|Q8NB16\|MLKL_HUMAN | +2 | 639,773417 | SEQ ID NO: 265 |
| TQTSMS[+80.0]LGTTR | MLKL (S360) | sp\|Q8NB16\|MLKL_HUMAN | +2 | 631,77596 | SEQ ID NO: 266 |
| TQTSM[+16.0]S[+80.0]LGTTR | MLKL (S360) | sp\|Q8NB16\|MLKL_HUMAN | +2 | 639,773417 | SEQ ID NO: 267 |
| TST[+80.0]FC[+57.0]GTPEFLAPEVLTETSYTR | PKN2 (T816) | sp\|Q16513\|PKN2_HUMAN | +3 | 896,403065 | SEQ ID NO: 268 |
| TSTFC[+57.0]GT[+80.0]PEFLAPEVLTETSYTR | PKN2 (T820) | sp\|Q16513\|PKN2_HUMAN | +3 | 896,403065 | SEQ ID NO: 269 |
| TST[+80.0]FC[+57.0]GTPEFLAPEVLTQEAYTR | PKN3 (T718) | sp\|Q6P5Z2\|PKN3_HUMAN | +3 | 900,07506 | SEQ ID NO: 270 |
| TSTFC[+57.0]GT[+80.0]PEFLAPEVLTQEAYTR | PKN3 (T722) | sp\|Q6P5Z2\|PKN3_HUMAN | +3 | 900,07506 | SEQ ID NO: 271 |
| T[+80.0]TQMSAAGTYAWMAPEVIK | MLK3 (T277) | sp\|Q16584\|M3K11_HUMAN | +2 | 1068,480709 | SEQ ID NO: 272 |
| TVC[+57.0]STY[+80.0]ILQSR | HIPK3 (Y359) | sp\|Q9H422\|HIPK3_HUMAN | +2 | 647,778503 | SEQ ID NO: 273 |
| VADPDHDHTGFLT[+80.0]EYVATR | Erk2 (T185) | sp\|P28482\|MK01_HUMAN | +3 | 741,995069 | SEQ ID NO: 274 |
| VADPDHDHTGFLTEY[+80.0]VATR | Erk2 (Y187) | sp\|P28482\|MK01_HUMAN | +3 | 741,995069 | SEQ ID NO: 275 |
| VADPDHDHTGFLTEVAT[+80.0]R | Erk2 (T190) | sp\|P28482\|MK01_HUMAN | +3 | 741,995069 | SEQ ID NO: 276 |
| VDNEDIY[+80.0]ESR | FRK (Y387) | sp\|P42685\|FRK_HUMAN | +2 | 660,261197 | SEQ ID NO: 277 |
| VIEDDPEAVY[+80.0]TTTGGK | EphA7 (Y791) | sp\|Q15375\|EPHA7_HUMAN | +2 | 887,892772 | SEQ ID NO: 278 |
| VLEDDPEAAY[+80.0]TTTGGK | EphA6 (Y830) | sp\|Q9UF33\|EPHA6_HUMAN | +2 | 873,877122 | SEQ ID NO: 279 |
| HPGHYAVYNLS[+80.0]PR | GAK (S456) | sp\|O14976\|GAK_HUMAN | +3 | 530,911952 | SEQ ID NO: 280 |
| DESEVS[+80.0]DEGGSPISSEGQEPR | GAK (S829) | sp\|O14976\|GAK_HUMAN | +3 | 757,635934 | SEQ ID NO: 281 |
| DESEVSDEGGS[+80.0]PISSEGQEPR | GAK (S834) | sp\|O14976\|GAK_HUMAN | +3 | 757,635934 | SEQ ID NO: 282 |

FIG. 6N

| Modified Peptide Sequence | Common Kinase Name and Phosphosite Localization | Uniprot ID and Name | Precursor Ion Charge | Precursor Ion m/z | SEQ ID |
|---|---|---|---|---|---|
| VS[+80.0]ENDFEDLLSNQGFSSR | GAK (S1176) | sp\|O14976\|GAK_HUMAN | +2 | 1062,449505 | SEQ ID NO: 283 |
| VS[+80.0]ENDFEDLLS[+80.0]NQGFSSR | GAK (S1176&S1185) | sp\|O14976\|GAK_HUMAN | +2 | 1102,432671 | SEQ ID NO: 284 |
| VVDFGSATFDHEHHSTIVST[+80.0]R | CLK2 (T344) | sp\|P49760\|CLK2_HUMAN | +3 | 808,032294 | SEQ ID NO: 285 |
| VYT[+80.0]HEVVTLWYR | CDK1 (T161) | sp\|P06493\|CDK1_HUMAN | +3 | 549,263991 | SEQ ID NO: 286 |
| SPEVLLGS[+80.0]AR | CDK1 (S178) | sp\|P06493\|CDK1_HUMAN | +2 | 554,773546 | SEQ ID NO: 287 |
| VLEDDPEAT[+80.0]Y[+80.0]TTSGGK | EphA2 (T771/Y772) | sp\|P29317\|EPHA2_HUMAN | +2 | 921,857745 | SEQ ID NO: 288 |
| WTAPEAIS[+80.0]YR | EphA2 (S790) | sp\|P29317\|EPHA2_HUMAN | +2 | 637,284278 | SEQ ID NO: 289 |
| WTAPEAIS[+80.0]Y[+80.0]R | EphA2 (S790/Y791) | sp\|P29317\|EPHA2_HUMAN | +2 | 677,267443 | SEQ ID NO: 290 |
| WTAPEAISY[+80.0]R | EphA2 (Y791) | sp\|P29317\|EPHA2_HUMAN | +2 | 637,284278 | SEQ ID NO: 291 |
| ADENY[+80.0]YK | Syk (Y525) | sp\|P43405\|KSYK_HUMAN | +2 | 491,681323 | SEQ ID NO: 292 |
| ADENYY[+80.0]K | Syk (Y526) | sp\|P43405\|KSYK_HUMAN | +2 | 491,681323 | SEQ ID NO: 293 |
| WYAPEC[+57.0]IINY[+80.0]YK | Syk (Y546) | sp\|P43405\|KSYK_HUMAN | +2 | 793,82291 | SEQ ID NO: 294 |
| VAGS[+80.0]QQPITVAWYK | TTN (S9203) | sp\|Q8WZ42\|TITIN_HUMAN | +2 | 750,368342 | SEQ ID NO: 295 |
| VAGS[+80.0]QQPIT[+80.0]VAWYK | TTN (S9203/T9207) | sp\|Q8WZ42\|TITIN_HUMAN | +2 | 790,351507 | SEQ ID NO: 296 |
| VAGSQQPIT[+80.0]VAWYK | TTN (T9207) | sp\|Q8WZ42\|TITIN_HUMAN | +2 | 750,368342 | SEQ ID NO: 297 |
| Y[+80.0]MEDSTYYK | FAK (Y570) | sp\|Q05397\|FAK1_HUMAN | +2 | 640,233062 | SEQ ID NO: 298 |
| Y[+80.0]M[+16.0]EDSTYYK | FAK (Y570) | sp\|Q05397\|FAK1_HUMAN | +2 | 648,23052 | SEQ ID NO: 299 |
| YMEDSTY[+80.0]YK | FAK (Y576) | sp\|Q05397\|FAK1_HUMAN | +2 | 640,233062 | SEQ ID NO: 300 |
| YM[+16.0]EDSTY[+80.0]YK | FAK (Y576) | sp\|Q05397\|FAK1_HUMAN | +2 | 648,23052 | SEQ ID NO: 301 |
| YMEDSTYY[+80.0]K | FAK (Y577) | sp\|Q05397\|FAK1_HUMAN | +2 | 640,233062 | SEQ ID NO: 302 |
| YM[+16.0]EDSTYY[+80.0]K | FAK (Y577) | sp\|Q05397\|FAK1_HUMAN | +2 | 648,23052 | SEQ ID NO: 303 |

FIG. 60

| Modified Peptide Sequence | Common Kinase Name and Phosphosite Localization | Uniprot ID and Name | Precursor Ion Charge | Precursor Ion m/z | SEQ ID |
|---|---|---|---|---|---|
| YIEDEDY[+80.0]YK | PYK2/FAK2 (Y579) | sp\|Q14289\|FAK2_HUMAN | +2 | 659.249766 | SEQ ID NO: 304 |
| YIEDEDY[+80.0]Y[+80.0]K | PYK2/FAK2 (Y579/Y580) | sp\|Q14289\|FAK2_HUMAN | +2 | 699.232932 | SEQ ID NO: 305 |
| YIEDEDYY[+80.0]K | PYK2/FAK2 (Y580) | sp\|Q14289\|FAK2_HUMAN | +2 | 659.249766 | SEQ ID NO: 306 |
| YVLDDEY[+80.0]TSSVGSK | BTK (Y551) | sp\|Q06187\|BTK_HUMAN | +2 | 821.847833 | SEQ ID NO: 307 |
| YVLDDEY[+80.0]VSSFGAK | TXK (Y420) | sp\|P42681\|TXK_HUMAN | +2 | 836.860744 | SEQ ID NO: 308 |
| YVLDDQY[+80.0]TSSSGAK | TEC (Y519) | sp\|P42680\|TEC_HUMAN | +2 | 807.340175 | SEQ ID NO: 309 |
| YVLDDQY[+80.0]VSSVGTK | BMX (Y566) | sp\|P51813\|BMX_HUMAN | +2 | 827.374018 | SEQ ID NO: 310 |

S[+80.0] is phospho Serine

T[+80.0] is phospho Threonine

Y[+80.0] is phospho Tyrosine

M[+16.0] is Methionine oxidation

C[+57.0] is Carbamoylmethylated cysteine

FIG. 6P

METHOD FOR MONITORING KINASE ACTIVITY IN A SAMPLE

CROSS-REFERENCE TO RELATED APPLICATIONS

The present invention is a U.S. 371 National Entry of International Application No. PCT/EP2019/066501, filed Jun. 21, 2019, which claims priority to EP Application No. 18179104.7, filed Jun. 21, 2018. The entire content of which are incorporated by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 28,380 Byte ASCII (Text) file named "39126-251_ST25" created on Apr. 25, 2022.

DESCRIPTION

The present invention relates to a method for monitoring kinase activity in a sample.

Protein kinases play a pivotal role in cellular communication and aberrant kinase activity has been linked to a variety of disorders ranging from cancer to diabetes or cardiovascular disease. Kinases are key regulators of cellular communication and their inhibitors play central roles in targeted therapy and precision medicine. Therefore, the investigation of global kinase dynamics is fundamental to the understanding of cellular function and to advance rational drug development. This clear relevance of kinases has sparked numerous endeavours to assess kinome activity states. Most of them however suffer from substantial drawbacks.

In its most naïve application, activity of kinases is extracted from their abundance obtained in shotgun proteomics experiments. To account for the low abundance of most protein kinases, kinase specific enrichment protocols have been used, mainly consisting of immobilized broad-specificity kinase inhibitors and/or ATP-mimetics. This kind of approach yields substantial kinase enrichment, however at the cost of sensitivity, requiring substantial input material and thereby limiting the approach to cell line-based model systems. Importantly, assessment of kinase abundance does not per se reflect kinase activity, which thus far has mainly been extracted from phosphoproteomics data. Here, the alignment of over- or underrepresented sequence motifs in the phosphoproteomics dataset are linked to known kinase consensus sequences. This method, however, suffers from a large gap of knowledge, as most of the detected phosphosites have not been characterized in terms of functionality and substrate specificity for many kinases are redundant or simply unknown.

Given the above, there is a dire need for direct monitoring of kinase activity, which until now has mainly been extracted from either kinase protein expression levels or substrate phosphorylation data.

BRIEF DESCRIPTION OF THE DRAWINGS

FIG. 2A shows the result of the detection of 52 t-loop phosphorylation sites for the three cell lines.

In FIG. 3B an example is shown wherein the tyrosine phosphorylation of residues Y980 and Y981 of JAK3 is illustrated.

FIGS. 6A-6P shows a complete list of tryptic peptides.

Figure 1A:
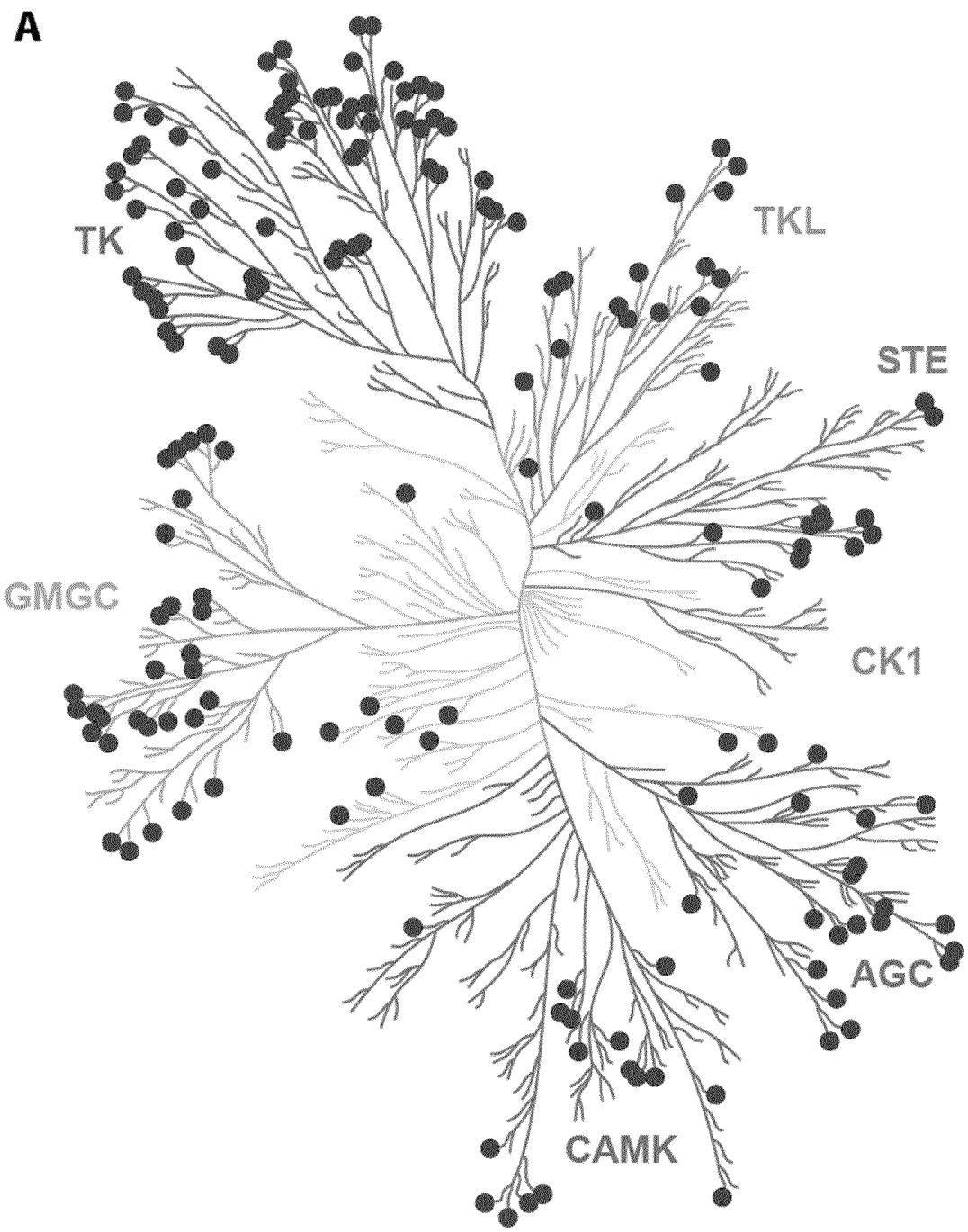
FIG. 1A shows the conserved activation sites based on sequence homologies on a kinome-wide scale.

The present invention provides hereto a method for monitoring of kinase activity or activation in a sample, the method comprises the steps of:
a) providing a sample comprising a kinase;
b) incubating the sample with a protease to cleave the kinase provided in step a) into protease specific proteolytic peptides;
c) applying phosphopeptide enrichment to the sample;
d) analysing the sample obtained in step c) via liquid chromatography-mass spectrometry (LC-MS); and
e) detecting phosphorylations of the kinase provided in step a), wherein the detection of step e) is performed only in case a proteolytic peptide associated with the activation region of the kinase is identified.

In order to identify and to detect the proteolytic peptide associated with the activation region of the kinase, the method of the present invention comprises the steps of:
i) determining the kinase to be monitored;
ii) determining protease specific proteolytic peptides associated with the activation region of the kinase of interest; and
iii) adjusting the settings of the mass spectrometer such that only the protease specific proteolytic peptides determined in step ii) are detected in step e). It is noted that the incubation of the sample with one protease will result in different protease specific proteolytic peptides associated with the activation region of the kinase of interest than in case another protease is used during the incubation step b) of the method of the present invention. As a result, the protease specific proteolytic peptides as determined in step ii) may vary based on the protease used. Consequently, the choice of protease will also result in different settings of the mass spectrometer in step iii) in order to detect the proteolytic peptides associated with the activation region of the kinase only. In other words, the mass spectrometer is used to identify (selectively select) only those proteolytic peptides of interest, i.e. proteolytic peptides associated with the activation region of the kinase of interest. Also, it is noted that the number of determined protease specific proteolytic peptides may differ. On one hand, a plurality of protease specific proteolytic peptides are determined in order to detect any activity or activation of a kinase of interest. On the other hand, a highly selective subset of protease specific proteolytic peptides are determined in order to detect specific relevant activity or activation of the kinase of interest only, e.g. the detection of specific proteolytic peptides associated with signalling pathways of a certain disease. It is further noted, that the determination of the protease specific proteolytic peptides in step ii) may result in a reference list used to adjust the setting of the mass spectrometer. In other words, the identification (selective selection) of protease specific proteolytic peptides of interest is based on the reference list produced in step ii). It is further noted that the determination of the proteolytic peptides of interest is performed based on the kinase of interest (i.e. the kinase to be monitored) in combination with the protease used during the incubation step.

It was found that by providing the method of the present invention, it is now possible to enable a direct link between phosphosite abundance and kinase activity. The activation region in kinases is a flexible loop positioned close to the catalytic loop, which, when phosphorylated, activates most kinases. The activation region in kinases is also known as the t-loop and together with the region just after the activation loop, called the P+1 loop, comprises a conserved region flanked by the Asp-Phe-Gly (DFG) and (Ala)-Pro-Glu ((A)PE) motif. It is noted that the term 'conserved region', 'conserved domain' or 'activation region' of a kinase is a well-known term used in the field of kinases. For example, the National Center for Biotechnology Information (NCBI) provides several tools (e.g. via the Conserved Domain Database) to identify and determine the activation region of numerous kinases. Based on the information provided by such databases, the inventors were able to identify 456 activation regions in kinases.

By providing the method of the present invention, it is now possible to monitor activation region associated phosphorylations, e.g. t-loop phosphorylations, in kinases, which are critical switches initiating activity in many of these kinases. Notably, the functionality of such sites can be directly transferred to numerous understudied kinases based on their high sequence similarities. It was found that activation region associated phosphorylations, t-loop phosphorylations in particular, are notoriously underrepresented in methods of the prior art, e.g. shotgun proteome analyses, due to their low abundance, unfavourable LC-MS characteristics and high prevalence of tyrosine phosphorylations.

The method of the present invention may further comprise the step of:
f) quantifying the phosphorylations detected in step e).

Preferably the quantification is achieved by targeted mass spectrometry, such as targeted MS1 (precursor ion scan), MS2 (tandem mass spectrometry or fragment ion scan) or $MS^n$ (tandem mass spectrometry) based quantification, wherein for $MS^n$ n is an integer greater than 2.

In a preferred embodiment, the proteolytic peptides associated with the activation region of the kinase comprise proteolytic peptides associated with the t-loop of the kinase. By performing the detection of step e) only in case a proteolytic peptide associated with the t-loop of the kinase is identified, the kinase activity or activation can be monitored without the need of further reprocessing the sample before applying the method of the present invention. As already noted, the activation region associated proteolytic peptides varies depending on the protease used. In an embodiment of the present invention, the protease may be selected from the group consisting of trypsin, endoprotease Glu-C, chymotrypsin and endoprotease Asp-N, resulting in trypsin specific proteolytic peptides (e.g. tryptic peptides), Glu-C specific proteolytic peptides, chymotrypsin specific proteolytic peptides (e.g. chymotryptic peptides) and Asp-N specific proteolytic peptides, respectively. However, other proteases known to the person skilled in the art may be selected as well in performing the method of the present invention.

The phosphopeptide enrichment is preferably selected from the group consisting of immobilized metal ion affinity chromatography (IMAC), such as Fe(III)-IMAC, Ga(III)-IMAC, Ti(IV)-IMAC or Zr(IV)-IMAC, and metal oxide affinity chromatography (MOAC), such as $TiO_2$-MOAC or $ZrO_2$-MOAC. In the most preferred embodiment the t-loop phosphopeptide enrichment comprises Fe(III)-IMAC. It was found that the use of Fe(III)-IMAC resulted in a method having a high specificity for, in particular, t-loop phosphorylations.

In a further preferred embodiment, the liquid chromatography may comprise reversed-phase chromatography and may be selected from the group consisting of nano-liquid chromatography, capillary flow liquid chromatography and capillary micro-flow liquid chromatography. Whereas the mass spectrometry may comprise a mass spectrometry acquisition method selected from the group consisting of selected reaction monitoring (SRM), multiple reaction monitoring (MRM), parallel reaction monitoring (PRM) and multiple reaction monitoring high-resolution (MRM-HR). Even further the mass spectrometry acquisition method may be selected from the group consisting of data-independent acquisition-based mass spectrometry (DIA or SWATH™) and targeted peptide quantitation (e.g. QuanDirect™). It is noted that the choice of the mass spectrometry acquisition method depends on the mass spectrometer available. It was found that any of the mass spectrometry acquisition methods mentioned above, i.e. targeted mass spectrometry methods, may be opted for in order to perform the method of the present invention. Even further the mass spectrometry may comprise tandem mass spectrometry. Preferably the mass spectrometry comprises the use of a quadrupole mass spectrometer, e.g. a triple quadrupole mass spectrometer, or a time-of-flight mass spectrometer. Also, the mass spectrometry may comprise the use of an ion-trap mass spectrometer, such as an Orbitrap mass spectrometer, or a linear ion trap mass spectrometer. It was found that by combining nano-LC with MS/MS in SRM mode on a triple quadrupole mass spectrometer, to monitor system wide t-loop phosphorylations as a probe for kinase activity, a highly specific method is provided.

Figure 1B:
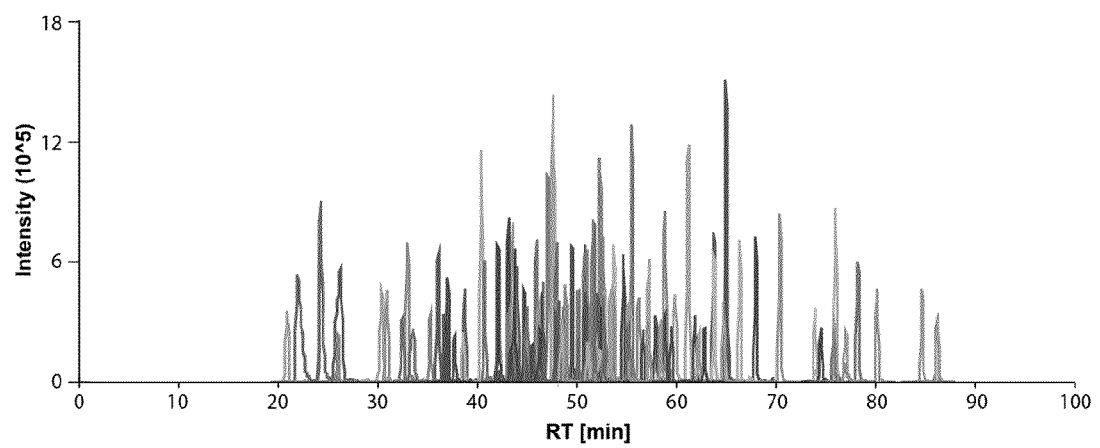
FIG. 1B shows heavy-isotope-labeled peptides synthesized for all entries of the targeted kinases and used for nanoLC-SRM assay development.

Based on the method of the present invention, assays for t-loop phosphorylation on 178 protein kinases are provided, accounting for roughly 33% of the global human kinome. The strength of the technology lies in the combination of sensitivity (t-loop phosphopeptide enrichment and LC-MS) enabling substantial kinome coverage even from limited starting material, and throughput. Such high sensitive coverage may be further facilitated by using an (automated) platform with parallel phosphopeptide enrichment up to 96 samples. In total 74 t-loop phosphorylations were detected for 58 kinases across numerous cell types (primary and patient-derived). The targeted kinases included numerous clinically relevant kinases with FDA approved inhibitors such as MET, ABL, SRC, BTK, JAK3 and KIT (see also: FIG. 1A and FIG. 1B). A complete overview of the detected t-loop phosphorylations across various cell lines is provided in Table 1. A complete list of tryptic peptides is provided in FIG. 6.

TABLE 1

List of detected t-loop phosphorylations (indicated with *) and cysteine carbamidomethylations (indicated with **) in various cell lines.

| Peptide sequence measured | t-loop phosphorylation site | Cell line | SEQ ID |
| --- | --- | --- | --- |
| IGDFGLAT*VK | ARAF - T454/ BRAF - T599/ RAF1 - T491 | Platelets | SEQ ID NO: 13 |
| YVLDDEY*TSSVGSK | BTK - Y551 | Platelets | SEQ ID NO: 307 |
| GDVMST*AC**GTPGYVAPEVLAQK | CaMK1D - T180 | Jurkat, PC9 | SEQ ID NO: 141 |
| GAILT*TMLATR | CaMK2α - T305/ CaMK2β - T306/ CaMK2δ - T306 | Platelets | SEQ ID NO: 43 |
| GAILTT*MLATR | CaMK2α - T306/ CaMK2β - T307/ CaMK2δ - T307 | Platelets | SEQ ID NO: 47IAD |
| IADFGLS*K | CAMKIV - S189/ RIPK2 - S168 | PC9, M026, Platelets | SEQ ID NO: 171 |
| T*VC**GTPGYCAPEILR | CAMKIV - T200 | Jurkat, M026 | SEQ ID NO: 247 |
| SPEVLLGS*AR | CDK1 - S178 | Jurkat, PC9, M026 | SEQ ID NO: 287 |
| VYT*HEVVTLWYR | CDK1 - T161 | Jurkat, HEK, PC9, M026 | SEQ ID NO: 286 |
| EYGS*PLK | CDK11A - S577/ CDK11B - S589 | Jurkat, HEK, PC9, M026 | SEQ ID NO: 17 |
| AYT*PVVVTLWYR | CDK11B - T595 | Jurkat, HEK, PC9, M026 | SEQ ID NO: 81 |
| NSS*PAPPQPAPGK | CDK12 - S1053 | Jurkat, HEK, PC9, M026 | SEQ ID NO: 223 |
| TYT*HEVVTLWYR | CDK2 - T160 | Jurkat, HEK, PC9, M026 | SEQ ID NO: 41 |
| SFGS*PNR | CDK7 - S164 | Jurkat, HEK, PC9, M026 | SEQ ID NO: 231 |
| AYT*HQVVTR | CDK7 - T169 | Jurkat, HEK, PC9, M026 | SEQ ID NO: 232 |
| AFS*LAK | CDK9 - S175 | PC9, M026 | SEQ ID NO: 69 |
| ILGETS*LMR | CHK2 - s379 | Jurkat, HEK, PC9, M026 | SEQ ID NO: 245 |
| IYQY*IQSR | DYRK1A - Y321 | Jurkat, HEK, PC9, M026, Platelets | SEQ ID NO: 68 |
| VYTY*IQSR | DYRK2 - Y382 | Jurkat, HEK, PC9, M026 | SEQ ID NO: 63 |
| LYTY*IQSR | DYRK3 - Y369 | Jurkat | SEQ ID NO: 188 |
| WTAPEAIS*YR | EPHA2 - S790 | M026 | SEQ ID NO: 289 |

TABLE 1-continued

List of detected t-loop phosphorylations (indicated with *) and cysteine carbamidomethylations (indicated with **) in various cell lines.

| Peptide sequence measured | t-loop phosphorylation site | Cell line | SEQ ID |
|---|---|---|---|
| VLEDDPEAAY*TTR | EPHA3 - Y779/ EPHA4 - Y779/ EPHA5- Y833 | PC9 | SEQ ID NO: 38 |
| IADPEHDHTGFLTEY*VATR | ERK1 - Y204 | Jurkat, PC9, M026, Platelets | SEQ ID NO: 174 |
| VADPDHDHTGFLTEY*VATR | ERK2 - Y187 | Jurkat, PC9, M026, Platelets | SEQ ID NO: 275 |
| GHLS*EGLVTK | ERK3 - S189 | Jurkat, HEK, PC9, M026 | SEQ ID NO: 143 |
| GYLS*EGLVTK | ERK4 - S186 | HEK, M026R | SEQ ID NO: 156 |
| Y*MEDSTYYK | FAK - Y570 | HEK, PC9, M026 | SEQ ID NO: 298 |
| YIEDEDY*Y*K | FAK2 - Y579&Y580 | Platelets | SEQ ID NO: 305 |
| QEDGGVY*SSSGLK | FER - Y714 | Platelets | SEQ ID NO: 220 |
| LIEDNEY*TAR | FYN - Y420/LCK - Y394/YES1 - Y426/SRC - Y419 | Jurkat, HEK, PC9, M026, Platelets | SEQ ID NO: 10 |
| WTAPEAALY*GR | FYN - Y440/YES1 - Y446/ SRC - Y439 | Jurkat, Platelets | SEQ ID NO: 11 |
| GEPNVSY*IC**SR | GSK3α - Y279/ GSK3β - Y216 | Jurkat, HEK, PC9, M026, Platelets | SEQ ID NO: 29 |
| VIEDNEY*TAR | HCK - Y411/LYN - Y397 | HEK, PC9, Platelets | SEQ ID NO: 12 |
| TVC**STY*LQSR | HIPK3 - Y359 | Jurkat, HEK, PC9, M026 | SEQ ID NO: 273 |
| FAQTVMTS*R | IRAK4 - S346 | Platelets | SEQ ID NO: 132 |
| FAQTVMT*SR | IRAK4 - T345 | Platelets | SEQ ID NO: 130 |
| TAGTSFMMT*PYVVTR | JNK1 - T183/JNK3 - T221 | PC9 | SEQ ID NO: 32 |
| TAGTSFMMTPY*VVTR | JNK1 - Y185/ JNK3 - Y224 | PC9 | SEQ ID NO: 36 |
| TAC**TNFMMTPY*VVTR | JNK2 - Y185 | Platelets | SEQ ID NO: 253 |
| LDT*FC**GSPPYAAPELFQGK | Mark1 - T215/ Mark2 - T208/ Mark3 - T211/ Mark4 - T214 | Jurkat, HEK, PC9, M026, Platelets | SEQ ID NO: 55 |
| EY*YSVHNK | MET - Y1234 | PC9 | SEQ ID NO: 120 |
| EY*Y*SVHNK | MET - Y1234&Y1235 | PC9 | SEQ ID NO: 121 |
| IDQGDLMT*PQFTPYYVAPQVLEAQR | MK5 - T182 | Jurkat, PC9, M026 | SEQ ID NO: 176 |
| LC*DFGISGQLVDS*IAK | MKK4 - S257 | PC9, M026, Platelets | SEQ ID NO: 185 |
| ATDS*FSGR | MNK2 - S74 | HEK, PC9 | SEQ ID NO: 77 |
| NT*FVGTPFWMAPEVIK | MST3 - T190/ YSK1 - T174 | PC9, M026 | SEQ ID NO: 1 |
| HMT*QEVVTQYYR | NLK - T298 | Jurkat, M026, Platelets | SEQ ID NO: 163 |
| S*VVGTPAYLAPEVLLNQGYNR | nPKC-D2 - S710 | Jurkat, HEK, PC9, M026 | SEQ ID NO: 242 |
| S*VVGTPAYLAPEVLR | nPKCµ - S742/ nPKCv - S735 | Jurkat, HEK, PC9, M026 | SEQ ID NO: 4 |

TABLE 1-continued

List of detected t-loop phosphorylations (indicated with *) and cysteine carbamidomethylations (indicated with **) in various cell lines.

| Peptide sequence measured | t-loop phosphorylation site | Cell line | SEQ ID |
|---|---|---|---|
| HTDDEMTGY*VATR | P38A - Y181 | Jurkat, HEK, PC9, M026, Platelets | SEQ ID NO: 169 |
| HTDDEMT*GY*VATR | P38A - Y181&T179 | Jurkat | SEQ ID NO: 166 |
| S*LVGTPYWMAPELISR | PAK4 - S475 | Jurkat, HEK, PC9, M026, Platelets | SEQ ID NO: 224 |
| S*LVGTPYWMAPEVISR | PAK6 - S560/ PAK7 - S602 | PC9 | SEQ ID NO: 64 |
| ANS*FVGTAQYVSPELLTEK | PDK1 - S241/ (PDK2 - S241) | Jurkat, HEK, PC9, M026, Platelets | SEQ ID NO: 54 |
| TWT*LC**GTPEYLAPEIILSK | PKA-Cα - T198 | Jurkat, PC9, M026 | SEQ ID NO: 18 |
| T*FC**GTPDYIAPEIIAYQPYGK | PKCα - T497/ PKCβ - T500/ PKCγ - T514 | Jurkat, PC9, M026, Platelets | SEQ ID NO: 5 |
| ENIFGES*R | PKCδ - S503 | Jurkat, HEK, PC9, M026, Platelets | SEQ ID NO: 114 |
| TNT*FC**GTPDYIAPEILLGQK | PKCθ - T538 | Jurkat, PC9, Platelets | SEQ ID NO: 263 |
| TSTFC**GT*PEFLAPEVLTETSYTR | PKN2 - T816 | PC9, M026 | SEQ ID NO: 269 |
| TLC**GT*PNYIAPEVLSK | PLK1 - T214 | Jurkat, PC9 | SEQ ID NO: 262 |
| IADLGLAS*FK | RIPK1 - S161 | Jurkat, Platelets | SEQ ID NO: 171 |
| MMSLS*QSR | RIPK2 - S176 | PC9, Platelets | SEQ ID NO: 189 |
| AENGLLMT*PC**YTANFVAPEVLK | RSK1 - T573/ RSK2 - T577 | PC9, M026 | SEQ ID NO: 30 |
| YVLDDQY*TSSSGAK | TEC - Y519 | Platelets | SEQ ID NO: 309 |
| ALGADDSY*YTAR | ZAP70 - Y492 | Jurkat | SEQ ID NO: 70 |

Further kinome coverage increase may be provided by applying alternative proteases, sample fractionation or applying enrichment for specific cell compartments such as nuclei or cell membrane.

Experiments

Figure 2A:
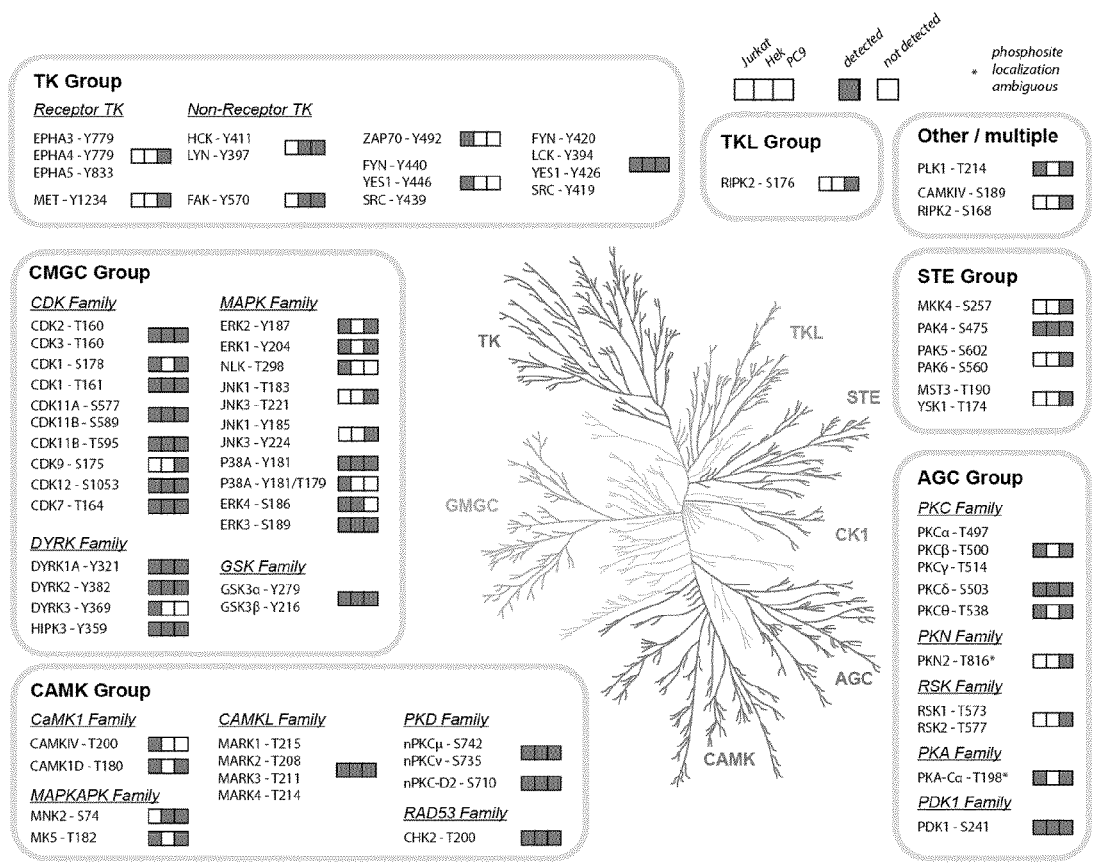
FIG. 2A shows the baseline kinome activity state of three different cell lines, i.e. Jurkat, PC9 and Hek, analysed without any form of stimulation.

The baseline kinome activity state of three different cell lines, i.e. Jurkat, PC9 and Hek, was analysed without any form of stimulation. This resulted in the detection of 52 t-loop phosphorylation sites for the three cell lines (FIG. 2A). Due to the highly conserved nature of the kinases' t-loop sequence the representative tryptic peptides are not always unique. This results in a certain amount of ambiguity, for instance for the kinase family members Mark1, Mark2, Mark3 and Mark4, or closely related kinases that often exhibit redundant functions such as the tyrosine kinases FYN, YES1 and SRC. To deal with this ambiguity the principle of protein grouping was followed and was referred to as these instances as kinase groups throughout this study. For the 52 phosphorylation sites observed, this results in 48 kinase groups. Moreover, while the t-loop is clearly defined through the flanking DFG and (A)PE motifs, phosphorylation can still occur at various or even multiple residues. Whereas for numerous kinases the activation residue(s) are clearly established, for others these sites within the t-loop are not known. Therefore, for the unknown cases multiple possibilities resulting in the development of SRM assays for various phosphosite isomers were taken into account.

A large part of the 48 detected kinase groups represented typical housekeeping kinases crucial for growing cells in typical culture conditions, such as CDKs and MAPKs as well as the two abundant kinases PDK1 and GSK3. Additionally, several kinases involved in anti-apoptotic processes were detected in an active state such as HIPK3. Both Jurkat and PC9 cells showed an increased activity of $Ca^{2+}$/DAG dependent signalling compared to Hek cells, with several kinases from the CaMK group and the PKC family being detected in their active state. These included CaMK1D, PKCθ, and the kinase group PKCα/PKCβ/PKCγ. CaMKIV activity on the other hand was detected exclusively in Jurkat cells.

Interestingly many kinases showed cell line dependent activity profiles. Some of them are known to be expressed in a tissue specific manner, such as the tyrosine kinase ZAP70 which is exclusively expressed in certain cell types associated with the immune system, including T-cells. Accordingly, t-loop phosphorylation of ZAP70 was exclusively detected in Jurkat cells.

Other tyrosine kinases such as FAK, MET and the two kinase groups EPHA3/4/5 and HCK/LYN could not be detected in Jurkat cells whereas they show high activity especially in PC9 cells. This is an indication for elevated tyrosine kinase activity in PC9, likely due to activated EGFR signalling. Notably, these activating phosphorylations occur on tyrosine residues within the t-loop sequence, which control the primary activation for a substantial number of kinases. Especially, tyrosine kinases and MAP kinases require tyrosine phosphorylation in their t-loop for full activation, while the primary activation site for most other kinases is a threonine residue.

Tyrosine phosphorylations are naturally underrepresented in phosphoproteome analyses unless specific phosphotyrosine enrichment is performed upfront. It was found that the Fe(III)-IMAC phosphopeptide enrichment in combination with sensitive SRM analysis in resulted in a substantial recovery of tyrosine t-loop phosphorylations.

In the case of FAK and MET phosphosite localization information within the t-loop for measurements in PC9 were obtained.

Figure 2B:
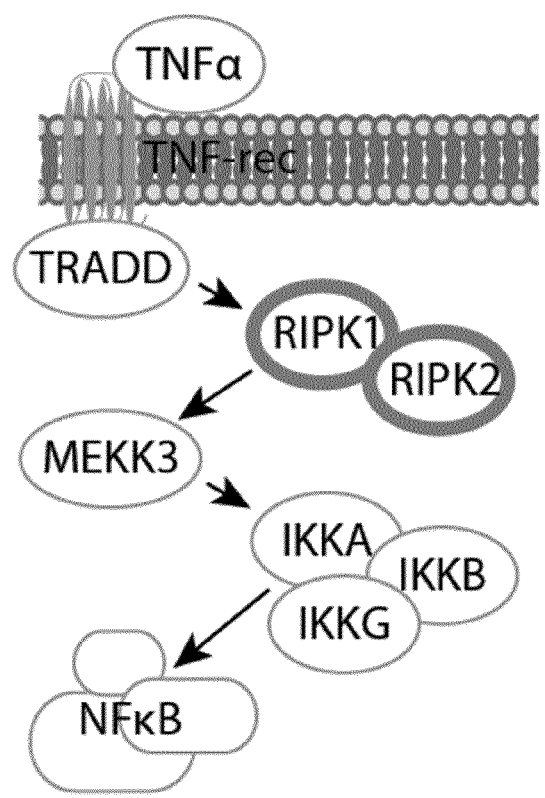
FIG. 2B shows TNF-α inducing the recruitment of receptor-interacting protein serine-threonine kinases (RIPKs) to the TNF-receptor complex, resulting in its activation and initiation of necroptotic signalling.
Figure 2C:
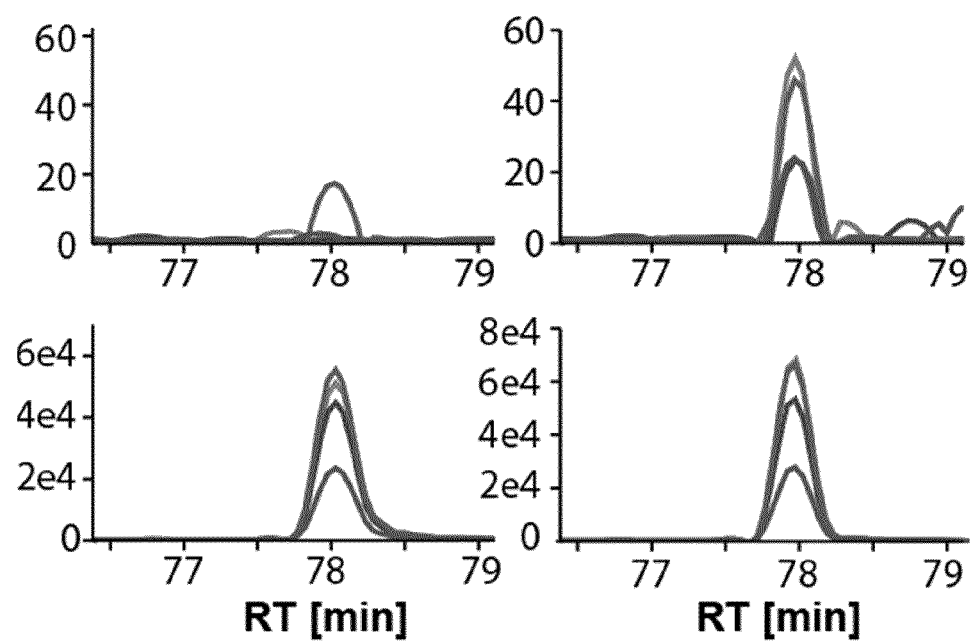
FIG. 2C shows RIPK1 phosphorylation at serine S161 reproducibly detected upon TNFα treatment, a phosphorylation not detectable in untreated Jurkat cells.

After the successful detection of several t-loop phosphorylations in unstimulated cells, the method was further fine-tuned to reveal activation of specific kinases from the steady-state background upon selected stimuli, since a large part of the kinome will be present in an inactive (unphosphorylated) state. Jurkat cells were treated with TNFα for 8 h, which resulted in increased cell death. Upon TNFα stimulation, the receptor-interacting protein serine-threonine kinase (RIPK) is recruited to the TNF receptor complex and mediates apoptosis (FIG. 2B). RIPK1 phosphorylation at serine S161 was reproducibly detected upon TNFα treatment, a phosphorylation not detectable in untreated Jurkat cells (FIG. 2C).

Despite the well characterized role of RIPK1 in cell death, it was found that direct detection by MS of RIPK1 t-loop phosphorylation from cell lysates is possible by the method of the present invention. Thus, the RIPK1 assay provides a new and robust readout to monitor the complex regulation of cell death, while it also demonstrates the unparalleled sensitivity of our technology.

Figure 3A:
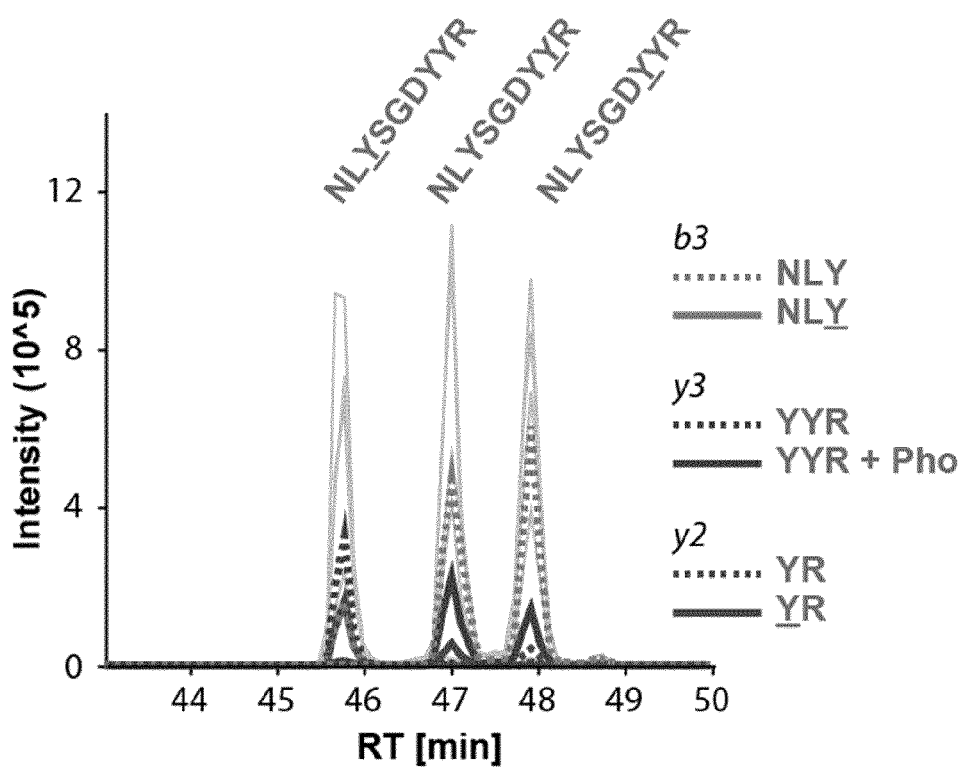
FIG. 3A shows an example of an assay for three phosphosites of the kinase DDR2 Indicating that the majority of phosphosites localization isomers are indistinguishable by chromatographic retention time on reverse phase LC.
Figure 3B:
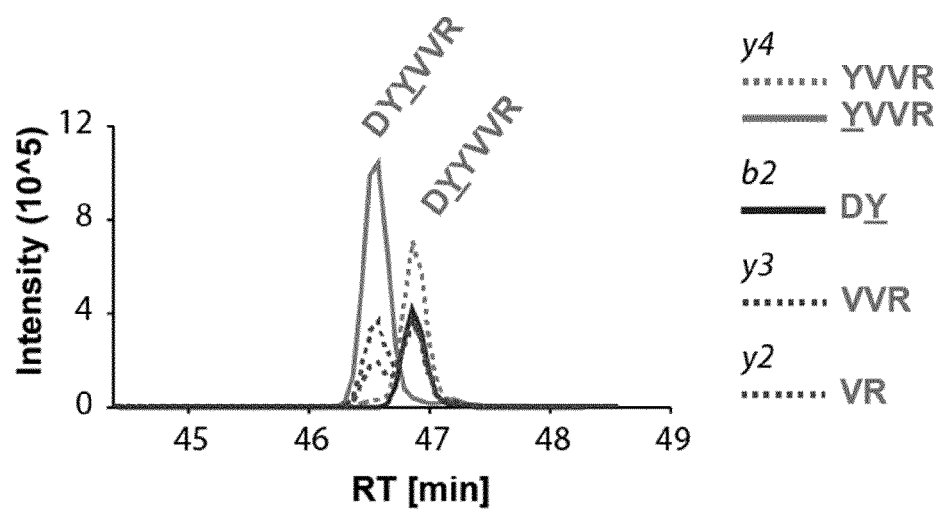
FIG. 3B shows an example of an assay showing partial chromatographic separation enabling the clear distinction of different phosphosite localization in complex samples by the use of phosphosite localization specific transitions.

The assays developed based on the method of the present invention comprised a total of 51 peptide sequences present in various positional isomers. 41 of them were present in 2 different isoforms, 10 were present in 3 different isoforms. While it is commonly believed that the majority of phosphosites localization isomers are indistinguishable by chromatographic retention time on reverse phase LC, with the method of the present invention baseline chromatographic separation was shown for all positional isomers for 47 out of 51 sequences. An example is shown for three phosphosites of the kinase DDR2 in FIG. 3A. Another two peptide sequences showed partial chromatographic separation enabling the clear distinction of different phosphosite localization in complex samples by the use of phosphosite localization specific transitions. An example is the tyrosine phosphorylation of residues Y980 and Y981 of JAK3, illustrated in FIG. 3B.

By performing in-depth analyses of kinome dynamics from primary cells the sensitivity of the kinase activity profiling approach was exploited. The technique of the present invention was applied to study the mechanism of platelet activation. Blood platelets activated by a hexapeptide mimicking thrombin were analysed, which binds to protease-activated receptor 1 (PAR1), for 1 min and 5 min and compared their kinase activity profile to naïve blood platelets. By using a mere 300 µg protein input per phosphopeptide enrichment, 31 t-loop phosphorylations in 25 kinase groups were detected and quantified. The comparative quantitative analysis between activated and naïve platelets revealed drastic changes of kinome activity levels upon PAR1 activation.

Figure 4A:
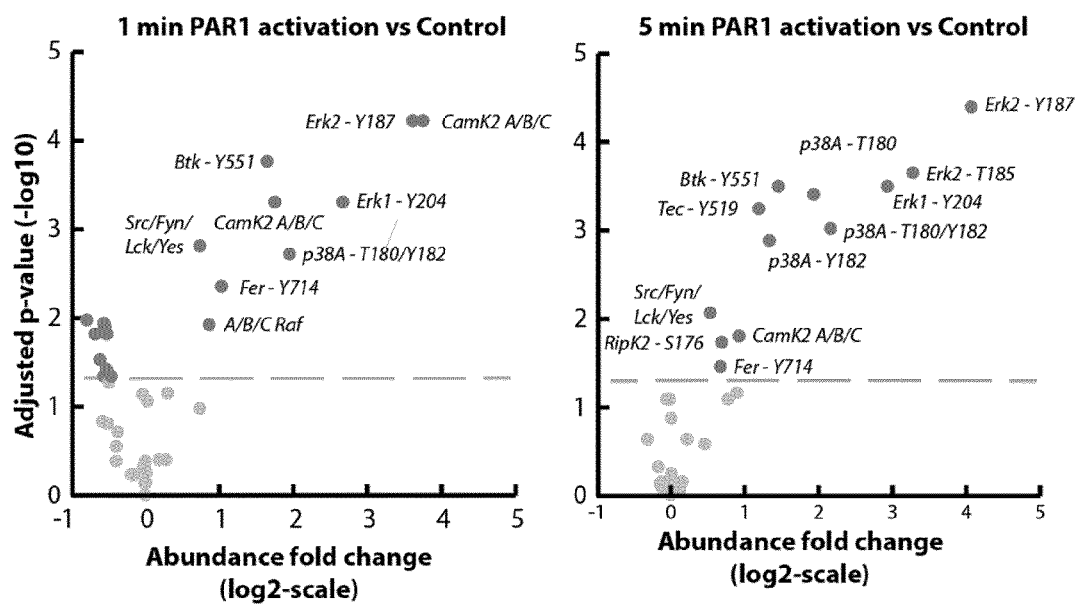
FIG. 4A shows the quantitative differences as volcano plots for 1 min and 5 min activation, respectively.
Figure 4B:
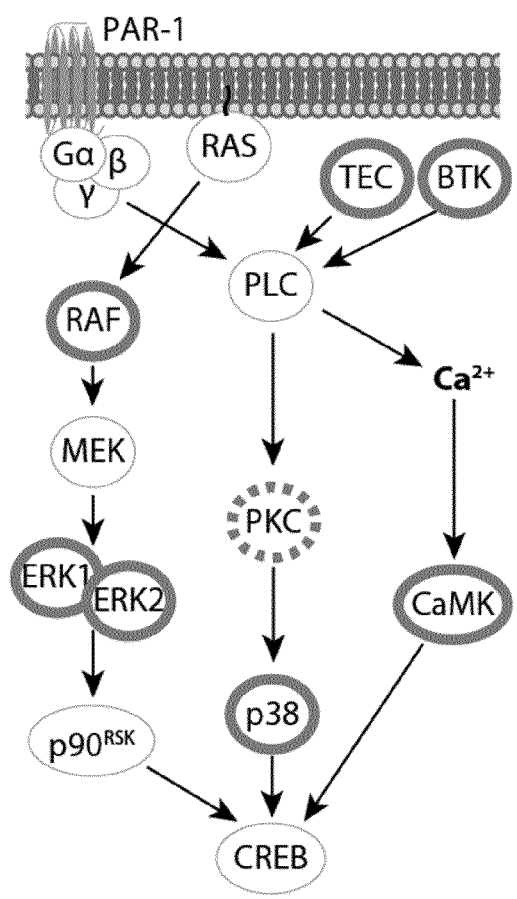
FIG. 4B shows platelet activation involves various intracellular signalling events, the majority of which converge into the common pathway.

FIG. 4A depicts the quantitative differences as volcano plots for 1 min and 5 min activation, respectively. Platelet activation involves various intracellular signalling events, the majority of which converge into the common pathway depicted in FIG. 4B. Noteworthy here is the detection of t-loop phosphorylations in the two Tec family tyrosine kinases Btk and Tec, both of which have been associated with platelet activation. Especially the role of Btk as a major activator of PLCγ2 is well established, while Tec has been connected to a more compensatory role when Btk is absent or malfunctioning, e.g. in case of X-linked agammaglobulinemia. The kinase activity profiles presented here corroborate these essential roles for Btk and Tec in platelet activation.

Figure 4C:
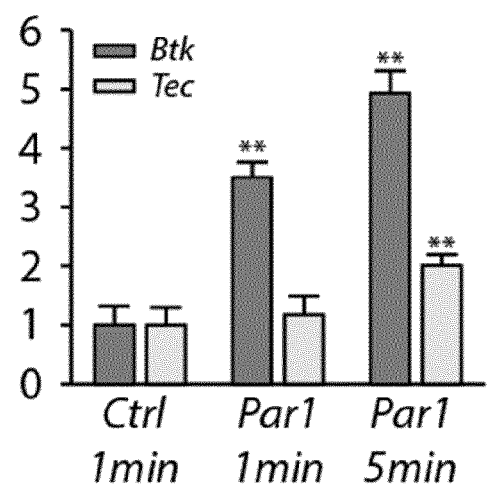
FIG. 4C shows Btk activity increased almost 4-fold upon 1 min Par1 activation and kept increasing at 5 min, whereas Tec showed much lower activation and lacked behind in time, corroborating the leading role of Btk.

Interestingly, it was found that the magnitude and kinetics of kinase activation differed between the two Tec family kinases. Where Btk activity increased almost 4-fold upon 1 min Par1 activation and kept increasing at 5 min, Tec showed much lower activation and lacked behind in time, corroborating the leading role of Btk (FIG. 4C).

Figure 4D:
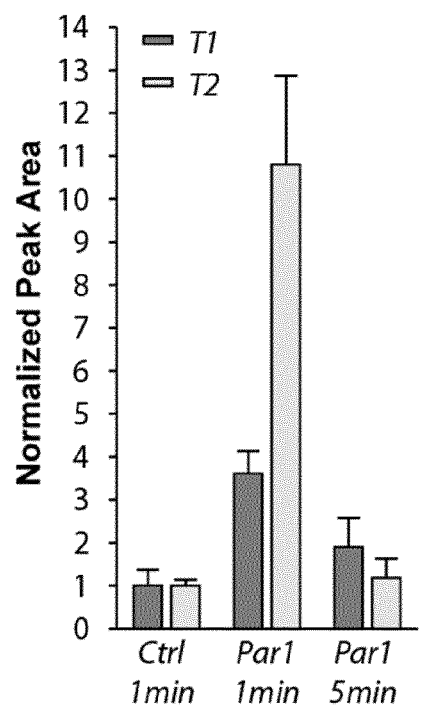
FIG. 4D shows the results of monitoring activation states of CaMK2 through quantification of two adjacent phosphosites in the t-loop (T305 and T306).

Downstream, a central converging point after PAR1 stimulation is the activation of phospholipase C (PLC) leading to an increase in intracellular $Ca^{2+}$ and thereby increased activity of calcium/calmodulin-dependent kinases (CaMK). It was found to be possible to monitor activation states of CaMK2 through quantification of two adjacent phosphosites in the t-loop (T305 and T306, FIG. 4D). Both phosphosites showed a drastic spike upon 1 min PAR1 activation, which dropped substantially after 5 min, demonstrating the short timescales involved in kinase activation. Interestingly, the specific kinetics of both phosphosites differed slightly. Whereas the T306 phosphorylation increased more than 10-fold after 1 min and returned to almost baseline after 5 min, the T305 spike was much less intense but showed a slower attenuation, suggesting dynamic regulation of the two phosphorylation events occurring in the CaMK2 t-loop.

Figure 4E:
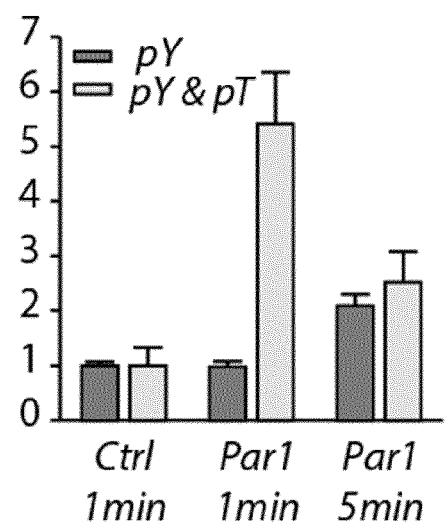
FIG. 4E shows representative dynamic regulation of kinase activation for key players in the pathway, p38.

Another target of PLC activity is PKC, which in turn activates p38. It was found that it is now possible to quantify several t-loop phosphorylations of PKC family members, including, PKCδ, PKCθ and the redundant t-loop sequence of PKCα, PKCβ and PKCγ. Interestingly, none of them showed any significant difference, while their downstream target p38A changed quite drastically. P38A requires double phosphorylation at T179 and Y181 for full kinase activity, a state observed especially pronounced after 1 min Par1 activation and which drastically decreased after 5 min (FIG. 4E). In parallel, singly phosphorylated p38A at Y181 remained at baseline levels after 1 min and only slightly increased after 5 min, suggesting a rapid double phosphorylation of p38A followed by a slower, partial, dephosphorylation resulting in the observed upregulation of single Y181 phosphorylation after 5 min, in line with previous studies. Combining the observed PKC and p38 t-loop phosphorylation implies either an extremely fast spike in PKC activity, already disappearing in less than 1 min, but able to activate p38 further downstream, or a massif signal amplification of p38 activation compared to PKC activity levels.

Figure 4F:
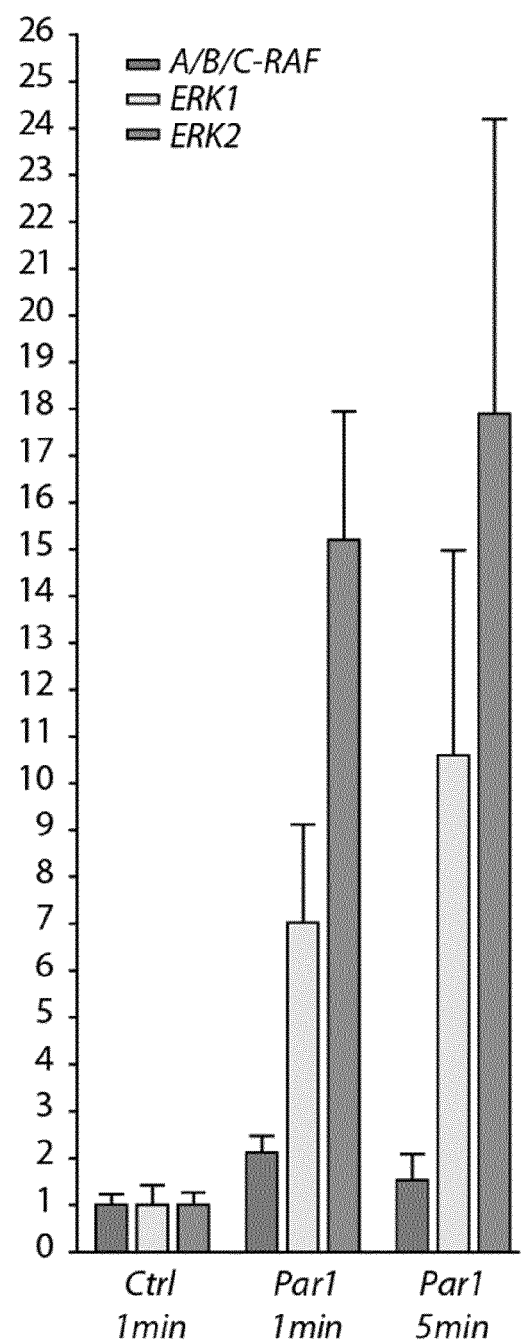
FIG. 4F shows representative dynamic regulation of kinase activation for key players in the pathway, RAF, ERK.

Another well studied effect of increasing intracellular Ca2+ levels is activation of RAS, via its translocation to the plasma membrane, and the subsequent activation of the MAPK cascade. The role of the MAPK cascade in platelets has not yet been fully elucidated, since platelets are anucleate cells with no potential to grow, differentiate or proliferate, however it seems to be a relevant factor in maintaining elevated intracellular $Ca^{2+}$ levels. An increase in kinase activity was shown for individual members of the MAPK signalling cascade. A slight increase in RAF activity was observed upon Par1 activation for 1 min, leading to strong activation Erk1 and Erk2 (FIG. 4F). Finally, several t-loop phosphorylations for kinases functioning in alternative platelet activation routes were observed, e.g. Fyn, Lyn, Yes, MKK4, JNK2 and FAK2, however no substantial differences in phosphorylation were observed suggesting the presence of baseline activity.

Following the effective analysis of kinase activation in primary cells, the usefulness of the method of the present invention to study unbalanced activity of kinases in disease was explored. Kinases have become a major class of drug targets, especially in cancer where 25 kinase-targeting drugs have been approved and numerous candidates are under clinical evaluation. However, in the identification of these candidates, through synthetic lethality screens, the (long-term) effect of inhibition of one kinase on the rest of the kinome is often neglected. This consistently leads to treatment resistance to targeted kinase inhibition due to adaptation of signalling networks.

Figure 5A:
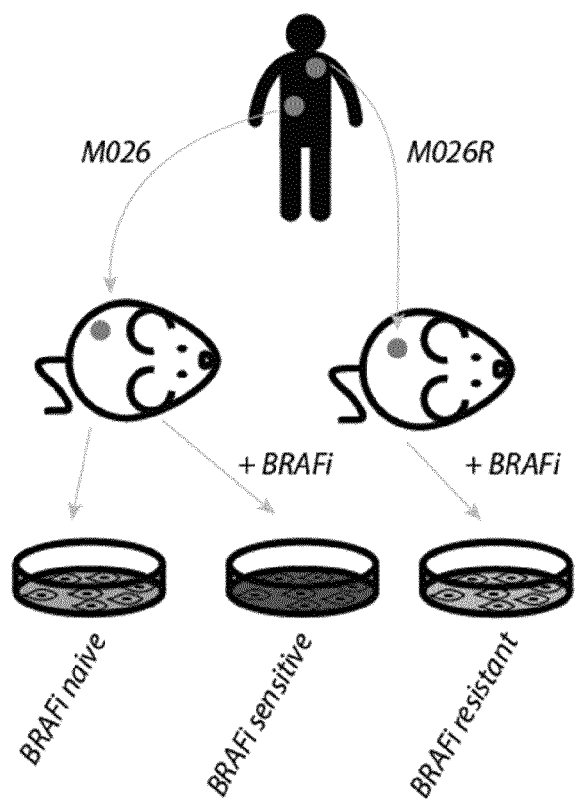
FIG. 5A is a schematical representation of acquired drug resistance studying in melanoma (BRAFV600E mutation).

To demonstrate the potential of the method of the present invention acquired drug resistance in melanoma was studied. A majority of melanoma is driven by a BRAFV600E mutation resulting in constitutive activity of BRAF. Despite initial success, treatment of patients with BRAF inhibitors (BRAFi) usually results in rapid acquisition of acquired drug resistance. Here, t-loop phosphorylations in matched patient-derived melanoma cell lines from treatment naïve, treatment sensitive and resistant tumor states established from patient-derived xenografts were studied (FIG. 5A), where the acquired drug resistance is based on an NRASQ61K mutation.

Figure 5B:
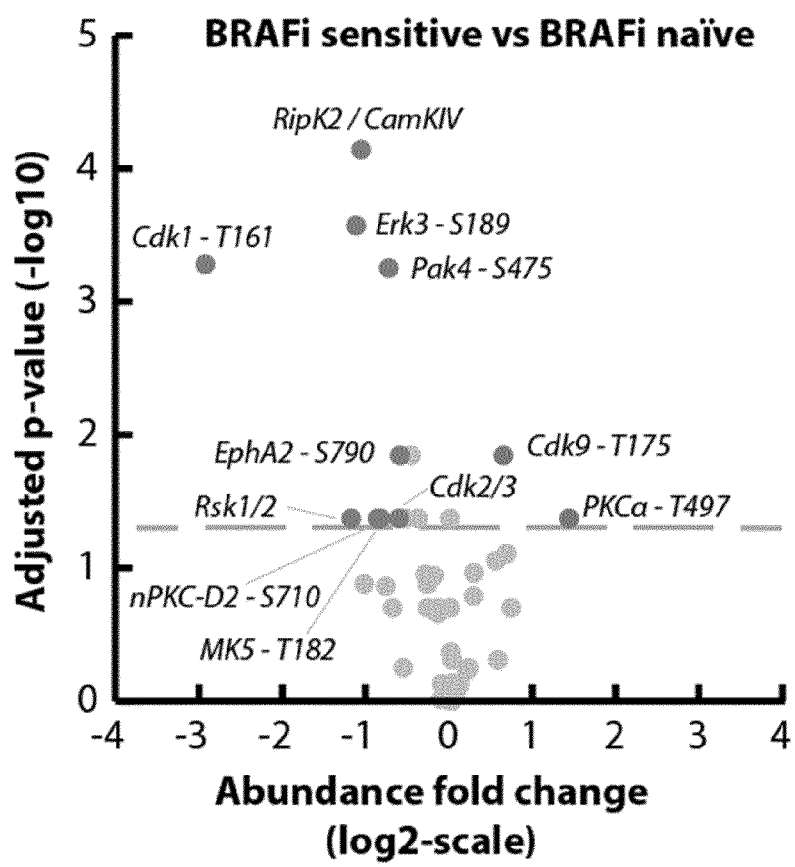
FIGS. 5B, 5C and 5D show the differential comparison of kinome activity in all three states 39 phosphosites detected and quantified representing t-loop phosphorylations of 36 kinase groups.
Figure 5C:
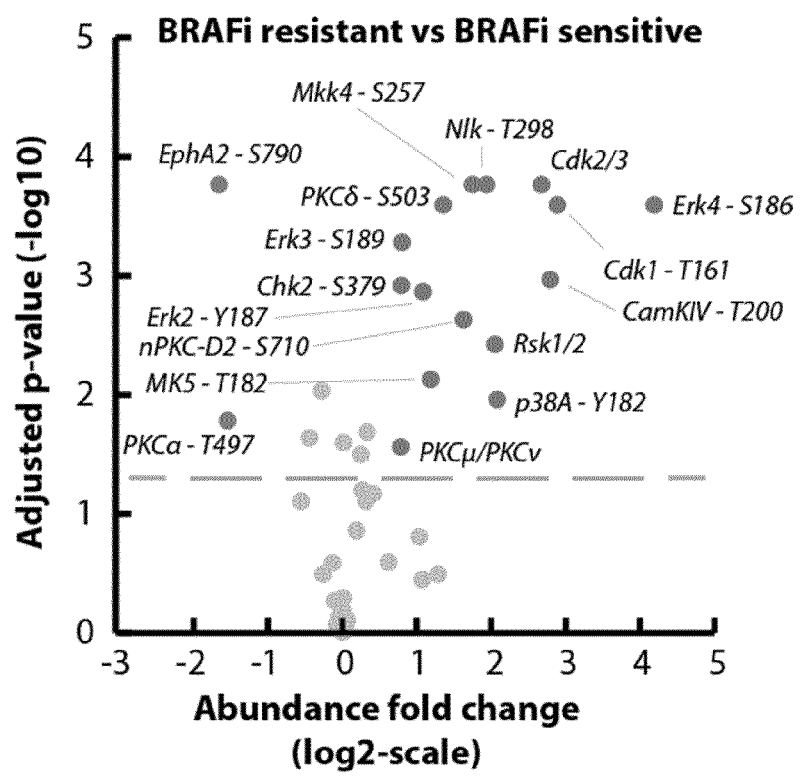
Figure 5D:
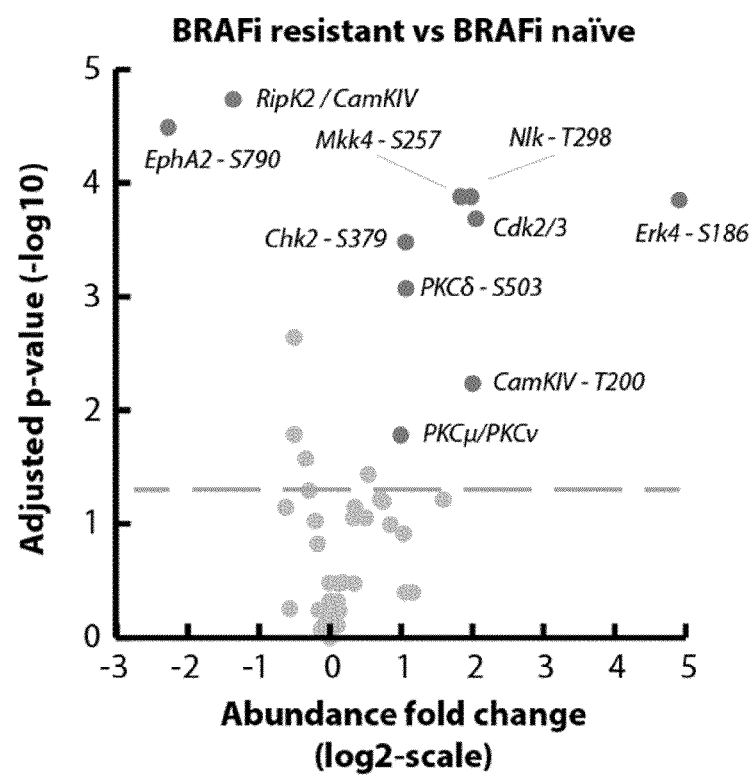

Through differential comparison of kinome activity in all three states 39 phosphosites were detected and quantified representing t-loop phosphorylations of 36 kinase groups (FIG. 5B-5D).

Several of the quantified kinases showed increased activity in the resistant cell line compared to the treatment naïve and sensitive cells. These kinases included CaMKIV, several members of the PKC kinase family such as PKCδ, PKCµ/v, several members associated to the MAPK cascade such as p38A, Erk2, Erk4 and MKK4 as well as the MAPK effector kinase NLK and cell cycle related kinases CDK2/3 and Chk2. Surprisingly, several kinases specifically activated in the drug resistant cell line have mainly been linked to tumour suppressing activities such as Chk2, p38A and Erk4.

The strongest activation was observed for the kinase Erk4, which, together with the also observed Erk3, belongs to the atypical MAPK family due to their lack of a tyrosine domain in the activation loop. Thus far, MK5 is the only known substrate of both Erk3 and Erk4. MK5 is mainly known for tumour suppressing functionality such as activation of p53 and FOXO3. Recent studies however also showed oncogenic potential for the Erk3/Erk4/MK5 module, for instance through inhibition of JNK activity and support of angiogenesis. Additionally, increased mRNA expression of MK5 was linked to increased probability of the development of metastasis.

Figure 5E:
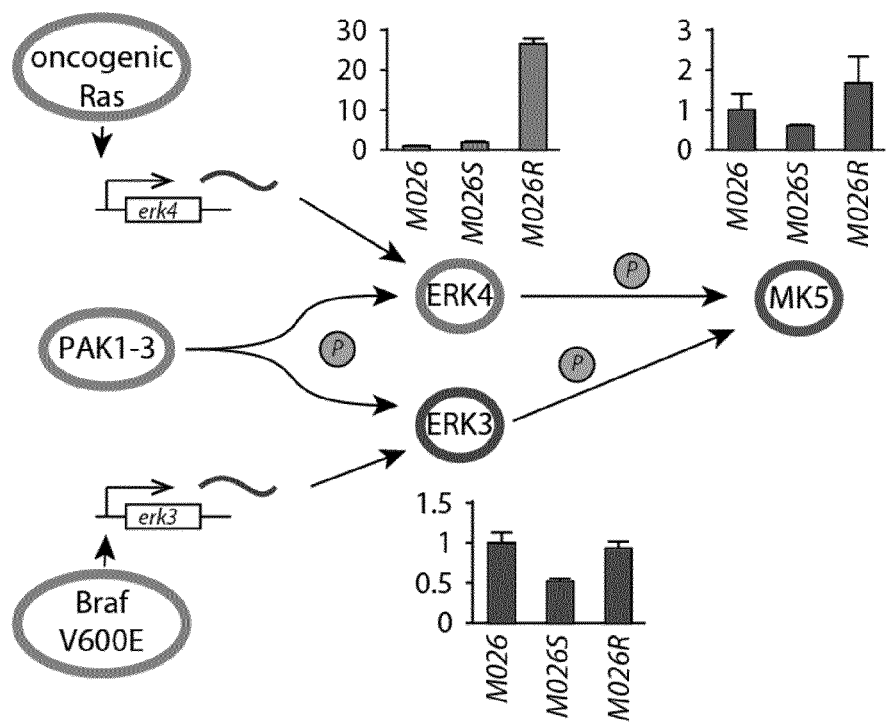
FIG. 5E shows that inhibition of BRAFV600E goes in parallel with a decrease in t-loop phosphorylation of Erk3, which is accompanied with a decrease in MKS.

Interestingly, the dynamics of ERK3/ERK4 expression has been linked to increased expression of both BRAFV600E and oncogenic RAS, leading to increased expression of Erk3 and Erk4, respectively. The data revealed that inhibition of BRAFV600E goes in parallel with a decrease in t-loop phosphorylation of Erk3, which is accompanied with a decrease in MK5 (FIG. 5E). Erk3 levels are restored upon acquired drug resistance and strikingly, oncogenic RAS drastically elevates Erk4 t-loop phosphorylation, over 20-fold compared to the naïve and sensitive cells. Globally this leads to a higher MK5 kinase activity in resistant cells when compared to treatment naïve cells. The results indicate a possible interesting role of the ERK3/ERK4/MK5 system in NRAS driven BRAFi resistance in melanoma and highlight the potential of the method of the present invention to detect altered kinome activity upon targeted oncotherapy.

What is claimed is:

1. A method for monitoring kinase activity or activation in a sample, the method comprises the steps of:
   a) providing a sample comprising a kinase;
   b) incubating the sample with a protease to cleave the kinase provided in step a) into protease specific proteolytic peptides;
   c) applying phosphopeptide enrichment to the sample;
   d) analysing the sample obtained in step c) via liquid chromatography-mass spectrometry; and
   e) detecting phosphorylations of the kinase provided in step a), wherein the detection of step e) is performed only in case a proteolytic peptide obtained from the activation region of the kinase per se is identified.

2. The method of claim 1, wherein the method further comprises the steps of:
   i) determining the kinase to be monitored;
   ii) determining protease specific proteolytic peptides obtained from the activation region of the kinase of interest per se; and iii) adjusting the settings of the mass spectrometer such that each of the protease specific proteolytic peptides peaks determined in step ii) are clearly resolved from other peptide peaks and are specifically detected in step e).

3. The method of claim 1, wherein the method further comprises the step of:

f) quantifying the phosphorylations detected in step e).

4. The method of claim 3, wherein in step f) quantification is achieved by targeted mass spectrometry.

5. The method of claim 3, wherein in step f) quantification is achieved by targeted MS1, MS2 or MSn based quantification, wherein n is an integer greater than 2.

6. The method of claim 1, wherein the proteolytic peptides obtained from the activation region of the kinase per se comprise proteolytic peptides obtained from the t-loop of the kinase per se.

7. The method of claim 1, wherein the protease is selected from the group consisting of trypsin, endoprotease Glu-C, chymotrypsin and endoprotease Asp-N.

8. The method of claim 1, wherein the phosphopeptide enrichment is selected from the group consisting of immobilized metal ion affinity chromatography (IMAC).

9. The method of claim 1, wherein the phosphopeptide enrichment comprises Fe(III)-IMAC.

10. The method of claim 1, wherein the liquid chromatography comprises reversed-phase chromatography.

11. The method of claim 1, wherein the liquid chromatography is selected from the group consisting of nano-liquid chromatography, capillary flow liquid chromatography and capillary micro-flow liquid chromatography.

12. The method of claim 1, wherein the mass spectrometry comprises a mass spectrometry acquisition method selected from the group consisting of selected reaction monitoring, multiple reaction monitoring, parallel reaction monitoring and multiple reaction monitoring high-resolution.

13. The method of claim 1, wherein the mass spectrometry comprises a mass spectrometry acquisition method selected from the group consisting of data-independent acquisition (DIA) based mass spectrometry and targeted peptide quantitation.

14. The method of claim 1, wherein the mass spectrometry comprises tandem mass spectrometry.

15. The method of claim 1, wherein the mass spectrometry comprises the use of a quadrupole mass spectrometer or a time-of-flight mass spectrometer.

16. The method of claim 1, wherein the mass spectrometry comprises the use of an ion-trap mass spectrometer, such as an Orbitrap mass spectrometer, or a linear ion trap mass spectrometer.

17. The method of claim 1, wherein in step d) the liquid chromatography-mass spectrometry comprises the use of combining nano-liquid chromatography with MS/MS in selected reaction monitoring mode on a triple quadrupole mass spectrometer.

* * * * *

SEQUENCE LISTING

```
<160> NUMBER OF SEQ ID NOS: 310

<210> SEQ ID NO 1
<211> LENGTH: 16
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 1

Asn Thr Phe Val Gly Thr Pro Phe Trp Met Ala Pro Glu Val Ile Lys
1               5                   10                  15

<210> SEQ ID NO 2
<211> LENGTH: 16
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
```

```
<220> FEATURE:
<221> NAME/KEY: MOD_RES
<222> LOCATION: (10)..(10)
<223> OTHER INFORMATION: OXIDIATION

<400> SEQUENCE: 2

Asn Thr Phe Val Gly Thr Pro Phe Trp Met Ala Pro Glu Val Ile Lys
1               5                   10                  15

<210> SEQ ID NO 3
<211> LENGTH: 8
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 3

Ile Ala Asp Phe Gly Leu Ser Lys
1               5

<210> SEQ ID NO 4
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION

<400> SEQUENCE: 4

Ser Val Val Gly Thr Pro Ala Tyr Leu Ala Pro Glu Val Leu Arg
1               5                   10                  15

<210> SEQ ID NO 5
<211> LENGTH: 21
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (3)..(3)
<223> OTHER INFORMATION: CARBAMIDOMETHYLATION

<400> SEQUENCE: 5

Thr Phe Cys Gly Thr Pro Asp Tyr Ile Ala Pro Glu Ile Ile Ala Tyr
1               5                   10                  15

Gln Pro Tyr Gly Lys
            20

<210> SEQ ID NO 6
<211> LENGTH: 21
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: CARBAMIDOMETHYLATION
<220> FEATURE:
<221> NAME/KEY: MOD_RES
<222> LOCATION: (5)..(5)
<223> OTHER INFORMATION: PHOSPHORYLATION
```

```
<400> SEQUENCE: 6

Thr Phe Cys Gly Thr Pro Asp Tyr Ile Ala Pro Glu Ile Ile Ala Tyr
1               5                   10                  15

Gln Pro Tyr Gly Lys
            20

<210> SEQ ID NO 7
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 7

Asp Ile Tyr Glu Thr Asp Tyr Tyr Arg
1               5

<210> SEQ ID NO 8
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 8

Asp Ile Tyr Glu Thr Asp Tyr Tyr Arg
1               5

<210> SEQ ID NO 9
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 9

Asp Ile Tyr Glu Thr Asp Tyr Tyr Arg
1               5

<210> SEQ ID NO 10
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 10

Leu Ile Glu Asp Asn Glu Tyr Thr Ala Arg
1               5                   10

<210> SEQ ID NO 11
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION
```

```
<400> SEQUENCE: 11

Trp Thr Ala Pro Glu Ala Ala Leu Tyr Gly Arg
1               5                   10

<210> SEQ ID NO 12
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 12

Val Ile Glu Asp Asn Glu Tyr Thr Ala Arg
1               5                   10

<210> SEQ ID NO 13
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 13

Ile Gly Asp Phe Gly Leu Ala Thr Val Lys
1               5                   10

<210> SEQ ID NO 14
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 14

Pro Pro Tyr Thr Asp Tyr Val Ser Thr Arg
1               5                   10

<210> SEQ ID NO 15
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 15

Pro Pro Tyr Thr Asp Tyr Val Ser Thr Arg
1               5                   10

<210> SEQ ID NO 16
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
```

```
<400> SEQUENCE: 16

Pro Pro Tyr Thr Asp Tyr Val Ser Thr Arg
1               5                   10

<210> SEQ ID NO 17
<211> LENGTH: 7
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 17

Glu Tyr Gly Ser Pro Leu Lys
1               5

<210> SEQ ID NO 18
<211> LENGTH: 19
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: CARBAMIDOMETHYLATION

<400> SEQUENCE: 18

Thr Trp Thr Leu Cys Gly Thr Pro Glu Tyr Leu Ala Pro Glu Ile Ile
1               5                   10                  15

Leu Ser Lys

<210> SEQ ID NO 19
<211> LENGTH: 19
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: CARBAMIDOMETHYLATION
<220> FEATURE:
<221> NAME/KEY: MOD_RES
<222> LOCATION: (7)..(7)
<223> OTHER INFORMATION: PHOSPHORYLATION

<400> SEQUENCE: 19

Thr Trp Thr Leu Cys Gly Thr Pro Glu Tyr Leu Ala Pro Glu Ile Ile
1               5                   10                  15

Leu Ser Lys

<210> SEQ ID NO 20
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION

<400> SEQUENCE: 20

Gly Glu Glu Val Tyr Val Lys
1               5
```

-continued

```
<210> SEQ ID NO 21
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 21

Asp Pro Asp Tyr Val Arg
1               5

<210> SEQ ID NO 22
<211> LENGTH: 22
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: CARBAMIDOMETHYLATION
<220> FEATURE:
<221> NAME/KEY: MOD_RES
<222> LOCATION: (13)..(13)
<223> OTHER INFORMATION: PHOSPHORYLATION
<220> FEATURE:
<221> NAME/KEY: MOD_RES
<222> LOCATION: (14)..(14)
<223> OTHER INFORMATION: OXIDATION

<400> SEQUENCE: 22

Leu Cys Asp Phe Gly Val Ser Gly Gln Leu Ile Asp Ser Met Ala Asn
1               5                   10                  15

Ser Phe Val Gly Thr Arg
            20

<210> SEQ ID NO 23
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 23

Leu Met Thr Gly Asp Thr Tyr Thr Ala His Ala Gly Ala Lys
1               5                   10

<210> SEQ ID NO 24
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: OXIDATION
<220> FEATURE:
<221> NAME/KEY: MOD_RES
<222> LOCATION: (6)..(6)
<223> OTHER INFORMATION: PHOSPHORYLATION

<400> SEQUENCE: 24

Leu Met Thr Gly Asp Thr Tyr Thr Ala His Ala Gly Ala Lys
1               5                   10

<210> SEQ ID NO 25
<211> LENGTH: 14
<212> TYPE: PRT
<213> ORGANISM: Homo sapiens
```

```
<220> FEATURE:
<221> NAME/KEY: MOD_RES
<222> LOCATION: (7)..(7)
<223> OTHER INFORMATION: PHOSPHORYLATION

<400> SEQUENCE: 25

Leu Met Thr Gly Asp Thr Tyr Thr Ala His Ala Gly Ala Lys
1               5                   10

<210> SEQ ID NO 26
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: OXIDATION
<220> FEATURE:
<221> NAME/KEY: MOD_RES
<222> LOCATION: (7)..(7)
<223> OTHER INFORMATION: PHOSPHORYLATION

<400> SEQUENCE: 26

Leu Met Thr Gly Asp Thr Tyr Thr Ala His Ala Gly Ala Lys
1               5                   10

<210> SEQ ID NO 27
<211> LENGTH: 14
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 27

Leu Met Thr Gly Asp Thr Tyr Thr Ala His Ala Gly Ala Lys
1               5                   10

<210> SEQ ID NO 28
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: OXIDATION
<220> FEATURE:
<221> NAME/KEY: MOD_RES
<222> LOCATION: (8)..(8)
<223> OTHER INFORMATION: PHOSPHORYLATION

<400> SEQUENCE: 28

Leu Met Thr Gly Asp Thr Tyr Thr Ala His Ala Gly Ala Lys
1               5                   10

<210> SEQ ID NO 29
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: CARBAMIDOMETHYLATION
```

```
<400> SEQUENCE: 29

Gly Glu Pro Asn Val Ser Tyr Ile Cys Ser Arg
1               5                   10

<210> SEQ ID NO 30
<211> LENGTH: 22
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: CARBAMIDOMETHYLATION

<400> SEQUENCE: 30

Ala Glu Asn Gly Leu Leu Met Thr Pro Cys Tyr Thr Ala Asn Phe Val
1               5                   10                  15

Ala Pro Glu Val Leu Lys
            20

<210> SEQ ID NO 31
<211> LENGTH: 22
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: OXIDATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: CARBAMIDOMETHYLATION

<400> SEQUENCE: 31

Ala Glu Asn Gly Leu Leu Met Thr Pro Cys Tyr Thr Ala Asn Phe Val
1               5                   10                  15

Ala Pro Glu Val Leu Lys
            20

<210> SEQ ID NO 32
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION

<400> SEQUENCE: 32

Thr Ala Gly Thr Ser Phe Met Met Thr Pro Tyr Val Val Thr Arg
1               5                   10                  15

<210> SEQ ID NO 33
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION
```

```
<220> FEATURE:
<221> NAME/KEY: MOD_RES
<222> LOCATION: (11)..(11)
<223> OTHER INFORMATION: PHOSPHORYLATION

<400> SEQUENCE: 33

Thr Ala Gly Thr Ser Phe Met Met Thr Pro Tyr Val Val Thr Arg
1               5                   10                  15

<210> SEQ ID NO 34
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: OXIDATION
<220> FEATURE:
<221> NAME/KEY: MOD_RES
<222> LOCATION: (8)..(8)
<223> OTHER INFORMATION: OXIDATION
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 34

Thr Ala Gly Thr Ser Phe Met Met Thr Pro Tyr Val Val Thr Arg
1               5                   10                  15

<210> SEQ ID NO 35
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: OXIDATION
<220> FEATURE:
<221> NAME/KEY: MOD_RES
<222> LOCATION: (8)..(8)
<223> OTHER INFORMATION: OXIDATION
<220> FEATURE:
<221> NAME/KEY: MOD_RES
<222> LOCATION: (9)..(9)
<223> OTHER INFORMATION: PHOSPHORYLATION

<400> SEQUENCE: 35

Thr Ala Gly Thr Ser Phe Met Met Thr Pro Tyr Val Val Thr Arg
1               5                   10                  15

<210> SEQ ID NO 36
<211> LENGTH: 15
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 36

Thr Ala Gly Thr Ser Phe Met Met Thr Pro Tyr Val Val Thr Arg
1               5                   10                  15
```

-continued

```
<210> SEQ ID NO 37
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: OXIDATION
<220> FEATURE:
<221> NAME/KEY: MOD_RES
<222> LOCATION: (8)..(8)
<223> OTHER INFORMATION: OXIDATION
<220> FEATURE:
<221> NAME/KEY: MOD_RES
<222> LOCATION: (11)..(11)
<223> OTHER INFORMATION: PHOSPHORYLATION

<400> SEQUENCE: 37

Thr Ala Gly Thr Ser Phe Met Met Thr Pro Tyr Val Val Thr Arg
1               5                   10                  15

<210> SEQ ID NO 38
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION

<400> SEQUENCE: 38

Val Leu Glu Asp Asp Pro Glu Ala Ala Tyr Thr Thr Arg
1               5                   10

<210> SEQ ID NO 39
<211> LENGTH: 16
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 39

Met Ser Ala Ala Gly Thr Tyr Ala Trp Met Ala Pro Glu Val Ile Arg
1               5                   10                  15

<210> SEQ ID NO 40
<211> LENGTH: 16
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 40

Met Ser Ala Ala Gly Thr Tyr Ala Trp Met Ala Pro Glu Val Ile Arg
1               5                   10                  15

<210> SEQ ID NO 41
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
```

```
<400> SEQUENCE: 41

Thr Tyr Thr His Glu Val Val Thr Leu Trp Tyr Arg
1               5                   10

<210> SEQ ID NO 42
<211> LENGTH: 17
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 42

Ser Thr Met Val Gly Thr Pro Tyr Trp Met Ala Pro Glu Val Val Thr
1               5                   10                  15

Arg

<210> SEQ ID NO 43
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION

<400> SEQUENCE: 43

Gly Ala Ile Leu Thr Thr Met Leu Ala Thr Arg
1               5                   10

<210> SEQ ID NO 44
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 44

Gly Ala Ile Leu Thr Thr Met Leu Ala Thr Arg
1               5                   10

<210> SEQ ID NO 45
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (7)..(7)
<223> OTHER INFORMATION: OXIDATION

<400> SEQUENCE: 45

Gly Ala Ile Leu Thr Thr Met Leu Ala Thr Arg
1               5                   10
```

```
<210> SEQ ID NO 46
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: OXIDATION

<400> SEQUENCE: 46

Gly Ala Ile Leu Thr Thr Met Leu Ala Thr Arg
1               5                   10

<210> SEQ ID NO 47
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 47

Gly Ala Ile Leu Thr Thr Met Leu Ala Thr Arg
1               5                   10

<210> SEQ ID NO 48
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (7)..(7)
<223> OTHER INFORMATION: OXIDATION

<400> SEQUENCE: 48

Gly Ala Ile Leu Thr Thr Met Leu Ala Thr Arg
1               5                   10

<210> SEQ ID NO 49
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 49

Asp Val Tyr Ser Thr Asp Tyr Tyr Arg
1               5

<210> SEQ ID NO 50
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
```

-continued

```
<400> SEQUENCE: 50

Asp Val Tyr Ser Thr Asp Tyr Tyr Arg
1               5

<210> SEQ ID NO 51
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 51

Asp Val Tyr Ser Thr Asp Tyr Tyr Arg
1               5

<210> SEQ ID NO 52
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (3)..(3)
<223> OTHER INFORMATION: CARBAMIDOMETHYLATION

<400> SEQUENCE: 52

Tyr Thr Cys Gln Ile Lys
1               5

<210> SEQ ID NO 53
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (7)..(7)
<223> OTHER INFORMATION: CARBAMIDOMETHYLATION

<400> SEQUENCE: 53

Leu Ala Asp Phe Gly Ser Cys Leu Lys
1               5

<210> SEQ ID NO 54
<211> LENGTH: 19
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 54

Ala Asn Ser Phe Val Gly Thr Ala Gln Tyr Val Ser Pro Glu Leu Leu
1               5                   10                  15

Thr Glu Lys
```

```
<210> SEQ ID NO 55
<211> LENGTH: 19
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: CARBAMIDOMETHYLATION

<400> SEQUENCE: 55

Leu Asp Thr Phe Cys Gly Ser Pro Pro Tyr Ala Ala Pro Glu Leu Phe
1               5                   10                  15

Gln Gly Lys

<210> SEQ ID NO 56
<211> LENGTH: 19
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: CARBAMIDOMETHYLATION
<220> FEATURE:
<221> NAME/KEY: MOD_RES
<222> LOCATION: (7)..(7)
<223> OTHER INFORMATION: PHOSPHORYLATION

<400> SEQUENCE: 56

Leu Asp Thr Phe Cys Gly Ser Pro Pro Tyr Ala Ala Pro Glu Leu Phe
1               5                   10                  15

Gln Gly Lys

<210> SEQ ID NO 57
<211> LENGTH: 19
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: CARBAMIDOMETHYLATION
<220> FEATURE:
<221> NAME/KEY: MOD_RES
<222> LOCATION: (7)..(7)
<223> OTHER INFORMATION: PHOSPHORYLATION

<400> SEQUENCE: 57

Leu Asp Thr Phe Cys Gly Ser Pro Pro Tyr Ala Ala Pro Glu Leu Phe
1               5                   10                  15

Gln Gly Lys

<210> SEQ ID NO 58
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
```

```
<400> SEQUENCE: 58

Asp Tyr Tyr Val Val Arg
1               5

<210> SEQ ID NO 59
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (3)..(3)
<223> OTHER INFORMATION: PHOSPHORYLATION

<400> SEQUENCE: 59

Asp Tyr Tyr Val Val Arg
1               5

<210> SEQ ID NO 60
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 60

Asp Tyr Tyr Val Val Arg
1               5

<210> SEQ ID NO 61
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 61

Val Tyr Thr Tyr Ile Gln Ser Arg
1               5

<210> SEQ ID NO 62
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION

<400> SEQUENCE: 62

Val Tyr Thr Tyr Ile Gln Ser Arg
1               5

<210> SEQ ID NO 63
<211> LENGTH: 8
<212> TYPE: PRT
<213> ORGANISM: Homo sapiens
```

```
<220> FEATURE:
<221> NAME/KEY: MOD_RES
<222> LOCATION: (4)..(4)
<223> OTHER INFORMATION: PHOSPHORYLATION

<400> SEQUENCE: 63

Val Tyr Thr Tyr Ile Gln Ser Arg
1               5

<210> SEQ ID NO 64
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION

<400> SEQUENCE: 64

Ser Leu Val Gly Thr Pro Tyr Trp Met Ala Pro Glu Val Ile Ser Arg
1               5                   10                  15

<210> SEQ ID NO 65
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (9)..(9)
<223> OTHER INFORMATION: OXIDATION

<400> SEQUENCE: 65

Ser Leu Val Gly Thr Pro Tyr Trp Met Ala Pro Glu Val Ile Ser Arg
1               5                   10                  15

<210> SEQ ID NO 66
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: CARBAMIDOMETHYLATION

<400> SEQUENCE: 66

Ile Val Asp Phe Gly Ser Ser Cys Gln Leu Gly Gln Arg
1               5                   10

<210> SEQ ID NO 67
<211> LENGTH: 8
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
```

```
<400> SEQUENCE: 67

Ile Tyr Gln Tyr Ile Gln Ser Arg
1               5

<210> SEQ ID NO 68
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 68

Ile Tyr Gln Tyr Ile Gln Ser Arg
1               5

<210> SEQ ID NO 69
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 69

Ala Phe Ser Leu Ala Lys
1               5

<210> SEQ ID NO 70
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 70

Ala Leu Gly Ala Asp Asp Ser Tyr Tyr Thr Ala Arg
1               5                   10

<210> SEQ ID NO 71
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 71

Ala Pro Glu Met Val Asn Leu Tyr Ser Gly Lys
1               5                   10

<210> SEQ ID NO 72
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION
```

```
<400> SEQUENCE: 72

Ala Pro Glu Met Val Asn Leu Tyr Ser Gly Lys
1               5                   10

<210> SEQ ID NO 73
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: OXIDATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 73

Ala Pro Glu Met Val Asn Leu Tyr Ser Gly Lys
1               5                   10

<210> SEQ ID NO 74
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: OXIDATION
<220> FEATURE:
<221> NAME/KEY: MOD_RES
<222> LOCATION: (8)..(8)
<223> OTHER INFORMATION: PHOSPHORYLATION

<400> SEQUENCE: 74

Ala Pro Glu Met Val Asn Leu Tyr Ser Gly Lys
1               5                   10

<210> SEQ ID NO 75
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION

<400> SEQUENCE: 75

Ala Pro Glu Met Val Asn Leu Tyr Ser Gly Lys
1               5                   10

<210> SEQ ID NO 76
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: OXIDATION
<220> FEATURE:
<221> NAME/KEY: MOD_RES
<222> LOCATION: (9)..(9)
<223> OTHER INFORMATION: PHOSPHORYLATION
```

```
<400> SEQUENCE: 76

Ala Pro Glu Met Val Asn Leu Tyr Ser Gly Lys
1               5                   10

<210> SEQ ID NO 77
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 77

Ala Thr Asp Ser Phe Ser Gly Arg
1               5

<210> SEQ ID NO 78
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 78

Ala Val Pro Glu Gly His Glu Tyr Tyr Arg
1               5                   10

<210> SEQ ID NO 79
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 79

Ala Tyr Thr Pro Val Val Val Thr Leu Trp Tyr Arg
1               5                   10

<210> SEQ ID NO 80
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (3)..(3)
<223> OTHER INFORMATION: PHOSPHORYLATION

<400> SEQUENCE: 80

Ala Tyr Thr Pro Val Val Val Thr Leu Trp Tyr Arg
1               5                   10

<210> SEQ ID NO 81
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
```

-continued

<400> SEQUENCE: 81

Ala Tyr Thr Pro Val Val Val Thr Leu Trp Tyr Arg
1               5                   10

<210> SEQ ID NO 82
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: CARBAMIDOMETHYLATION

<400> SEQUENCE: 82

Ala Tyr Ser Phe Cys Gly Thr Ile Glu Tyr Met Ala Pro Asp Ile Val
1               5                   10                  15

Arg

<210> SEQ ID NO 83
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: CARBAMIDOMETHYLATION
<220> FEATURE:
<221> NAME/KEY: MOD_RES
<222> LOCATION: (11)..(11)
<223> OTHER INFORMATION: OXIDATION

<400> SEQUENCE: 83

Ala Tyr Ser Phe Cys Gly Thr Ile Glu Tyr Met Ala Pro Asp Ile Val
1               5                   10                  15

Arg

<210> SEQ ID NO 84
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (7)..(7)
<223> OTHER INFORMATION: CARBAMIDOMETHYLATION

<400> SEQUENCE: 84

Asp Asp Glu Tyr Asn Pro Cys Gln Gly Ser Lys
1               5                   10

<210> SEQ ID NO 85
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

```
<400> SEQUENCE: 85

Asp Asp Ile Tyr Ser Pro Ser Ser Ser Lys
1               5                   10

<210> SEQ ID NO 86
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 86

Asp Ile Met His Asp Ser Asn Tyr Val Ser Lys
1               5                   10

<210> SEQ ID NO 87
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: OXIDATION
<220> FEATURE:
<221> NAME/KEY: MOD_RES
<222> LOCATION: (8)..(8)
<223> OTHER INFORMATION: PHOSPHORYLATION

<400> SEQUENCE: 87

Asp Ile Met His Asp Ser Asn Tyr Val Ser Lys
1               5                   10

<210> SEQ ID NO 88
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 88

Asp Ile His His Ile Asp Tyr Tyr Lys
1               5

<210> SEQ ID NO 89
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 89

Asp Ile His His Ile Asp Tyr Tyr Lys
1               5

<210> SEQ ID NO 90
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION
```

```
<400> SEQUENCE: 90

Asp Ile Met Asn Asp Ser Asn Tyr Ile Val Lys
1               5                   10

<210> SEQ ID NO 91
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: OXIDATION
<220> FEATURE:
<221> NAME/KEY: MOD_RES
<222> LOCATION: (8)..(8)
<223> OTHER INFORMATION: PHOSPHORYLATION

<400> SEQUENCE: 91

Asp Ile Met Asn Asp Ser Asn Tyr Ile Val Lys
1               5                   10

<210> SEQ ID NO 92
<211> LENGTH: 11
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 92

Asp Ile Met Ser Asp Ser Asn Tyr Val Val Arg
1               5                   10

<210> SEQ ID NO 93
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: OXIDATION
<220> FEATURE:
<221> NAME/KEY: MOD_RES
<222> LOCATION: (8)..(8)
<223> OTHER INFORMATION: PHOSPHORYLATION

<400> SEQUENCE: 93

Asp Ile Met Ser Asp Ser Asn Tyr Val Val Arg
1               5                   10

<210> SEQ ID NO 94
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 94

Asp Ile Asn Asn Ile Asp Tyr Tyr Lys
1               5

<210> SEQ ID NO 95
<211> LENGTH: 9
<212> TYPE: PRT
<213> ORGANISM: Homo sapiens
```

```
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 95

Asp Ile Asn Asn Ile Asp Tyr Tyr Lys
1               5

<210> SEQ ID NO 96
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 96

Asp Ile Asn Asn Ile Asp Tyr Tyr Lys
1               5

<210> SEQ ID NO 97
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 97

Asp Ile Tyr Ser Thr Asp Tyr Tyr Arg
1               5

<210> SEQ ID NO 98
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 98

Asp Ile Tyr Ser Thr Asp Tyr Tyr Arg
1               5

<210> SEQ ID NO 99
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 99

Asp Ile Tyr Ser Thr Asp Tyr Tyr Arg
1               5

<210> SEQ ID NO 100
<211> LENGTH: 7
<212> TYPE: PRT
<213> ORGANISM: Homo sapiens
```

```
<220> FEATURE:
<221> NAME/KEY: MOD_RES
<222> LOCATION: (4)..(4)
<223> OTHER INFORMATION: PHOSPHORYLATION

<400> SEQUENCE: 100

Asp Ser Asn Tyr Ile Ser Lys
1               5

<210> SEQ ID NO 101
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 101

Asp Val His Asn Leu Asp Tyr Tyr Lys
1               5

<210> SEQ ID NO 102
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 102

Asp Val His Asn Leu Asp Tyr Tyr Lys
1               5

<210> SEQ ID NO 103
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 103

Asp Val Tyr Glu Glu Asp Ser Tyr Val Lys
1               5                   10

<210> SEQ ID NO 104
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 104

Asp Val Tyr Glu Glu Asp Ser Tyr Val Lys
1               5                   10
```

-continued

```
<210> SEQ ID NO 105
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 105

Asp Val Tyr Glu Glu Asp Ser Tyr Val Lys
1               5                   10

<210> SEQ ID NO 106
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 106

Asp Val Tyr Glu Thr Asp Tyr Tyr Arg
1               5

<210> SEQ ID NO 107
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 107

Asp Val Tyr Glu Thr Asp Tyr Tyr Arg
1               5

<210> SEQ ID NO 108
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 108

Asp Val Tyr Glu Thr Asp Tyr Tyr Arg
1               5

<210> SEQ ID NO 109
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 109

Glu Asp Val Tyr Leu Ser His Asp His Asn Ile Pro Tyr Lys
1               5                   10
```

```
<210> SEQ ID NO 110
<211> LENGTH: 14
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION

<400> SEQUENCE: 110

Glu Asp Val Tyr Leu Ser His Asp His Asn Ile Pro Tyr Lys
1               5                   10

<210> SEQ ID NO 111
<211> LENGTH: 14
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION

<400> SEQUENCE: 111

Glu Asp Val Tyr Leu Ser His Asp His Asn Ile Pro Tyr Lys
1               5                   10

<210> SEQ ID NO 112
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 112

Glu Glu Ala Asp Gly Val Tyr Ala Ala Ser Gly Gly Leu Arg
1               5                   10

<210> SEQ ID NO 113
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 113

Glu Ile Tyr Ser Ala Asp Tyr Tyr Arg
1               5

<210> SEQ ID NO 114
<211> LENGTH: 8
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 114

Glu Asn Ile Phe Gly Glu Ser Arg
1               5
```

```
<210> SEQ ID NO 115
<211> LENGTH: 18
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 115

Glu Pro Leu Ala Val Val Gly Ser Pro Tyr Trp Met Ala Pro Glu Val
1               5                   10                  15

Leu Arg

<210> SEQ ID NO 116
<211> LENGTH: 18
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (12)..(12)
<223> OTHER INFORMATION: OXIDATION

<400> SEQUENCE: 116

Glu Pro Leu Ala Val Val Gly Ser Pro Tyr Trp Met Ala Pro Glu Val
1               5                   10                  15

Leu Arg

<210> SEQ ID NO 117
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 117

Glu Val Tyr Ala Ala Asp Tyr Tyr Lys
1               5

<210> SEQ ID NO 118
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 118

Ala Tyr Thr Pro Val Val Val Thr Gln Trp Tyr Arg
1               5                   10

<210> SEQ ID NO 119
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
```

```
<220> FEATURE:
<221> NAME/KEY: MOD_RES
<222> LOCATION: (3)..(3)
<223> OTHER INFORMATION: PHOSPHORYLATION

<400> SEQUENCE: 119

Ala Tyr Thr Pro Val Val Thr Gln Trp Tyr Arg
1               5                   10

<210> SEQ ID NO 120
<211> LENGTH: 8
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 120

Glu Tyr Tyr Ser Val His Asn Lys
1               5

<210> SEQ ID NO 121
<211> LENGTH: 8
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (3)..(3)
<223> OTHER INFORMATION: PHOSPHORYLATION

<400> SEQUENCE: 121

Glu Tyr Tyr Ser Val His Asn Lys
1               5

<210> SEQ ID NO 122
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 122

Glu Tyr Tyr Ser Val His Asn Lys
1               5

<210> SEQ ID NO 123
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 123

Glu Tyr Tyr Ser Val Gln Gln His Arg
1               5

<210> SEQ ID NO 124
<211> LENGTH: 9
<212> TYPE: PRT
<213> ORGANISM: Homo sapiens
```

```
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (3)..(3)
<223> OTHER INFORMATION: PHOSPHORYLATION

<400> SEQUENCE: 124

Glu Tyr Tyr Ser Val Gln Gln His Arg
1               5

<210> SEQ ID NO 125
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 125

Glu Tyr Tyr Ser Val Gln Gln His Arg
1               5

<210> SEQ ID NO 126
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 126

Glu Tyr Tyr Thr Val Lys
1               5

<210> SEQ ID NO 127
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 127

Glu Tyr Tyr Thr Val Lys
1               5

<210> SEQ ID NO 128
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (3)..(3)
<223> OTHER INFORMATION: PHOSPHORYLATION

<400> SEQUENCE: 128

Glu Tyr Tyr Thr Val Lys
1               5
```

```
<210> SEQ ID NO 129
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 129

Glu Tyr Tyr Thr Val Lys
1               5

<210> SEQ ID NO 130
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 130

Phe Ala Gln Thr Val Met Thr Ser Arg
1               5

<210> SEQ ID NO 131
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (7)..(7)
<223> OTHER INFORMATION: PHOSPHORYLATION

<400> SEQUENCE: 131

Phe Ala Gln Thr Val Met Thr Ser Arg
1               5

<210> SEQ ID NO 132
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 132

Phe Ala Gln Thr Val Met Thr Ser Arg
1               5

<210> SEQ ID NO 133
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (8)..(8)
<223> OTHER INFORMATION: PHOSPHORYLATION
```

```
<400> SEQUENCE: 133

Phe Ala Gln Thr Val Met Thr Ser Arg
1               5

<210> SEQ ID NO 134
<211> LENGTH: 23
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 134

Phe Phe Ser Ser Glu Thr Thr Ala Ala His Ser Leu Val Gly Thr Pro
1               5                   10                  15

Tyr Tyr Met Ser Pro Glu Arg
            20

<210> SEQ ID NO 135
<211> LENGTH: 23
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (19)..(19)
<223> OTHER INFORMATION: OXIDATION

<400> SEQUENCE: 135

Phe Phe Ser Ser Glu Thr Thr Ala Ala His Ser Leu Val Gly Thr Pro
1               5                   10                  15

Tyr Tyr Met Ser Pro Glu Arg
            20

<210> SEQ ID NO 136
<211> LENGTH: 23
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 136

Phe Phe Ser Ser Glu Thr Thr Ala Ala His Ser Leu Val Gly Thr Pro
1               5                   10                  15

Tyr Tyr Met Ser Pro Glu Arg
            20

<210> SEQ ID NO 137
<211> LENGTH: 23
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (19)..(19)
<223> OTHER INFORMATION: OXIDATION
```

```
<400> SEQUENCE: 137

Phe Phe Ser Ser Glu Thr Thr Ala Ala His Ser Leu Val Gly Thr Pro
1               5                   10                  15

Tyr Tyr Met Ser Pro Glu Arg
            20

<210> SEQ ID NO 138
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 138

Phe Val Leu Asp Asp Gln Tyr Thr Ser Ser Thr Gly Thr Lys
1               5                   10

<210> SEQ ID NO 139
<211> LENGTH: 18
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 139

Phe Val Ser Val Tyr Gly Thr Glu Glu Tyr Leu His Pro Asp Met Tyr
1               5                   10                  15

Glu Arg

<210> SEQ ID NO 140
<211> LENGTH: 18
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (15)..(15)
<223> OTHER INFORMATION: OXIDATION

<400> SEQUENCE: 140

Phe Val Ser Val Tyr Gly Thr Glu Glu Tyr Leu His Pro Asp Met Tyr
1               5                   10                  15

Glu Arg

<210> SEQ ID NO 141
<211> LENGTH: 22
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: CARBAMIDOMETHYLATION
```

-continued

```
<400> SEQUENCE: 141

Gly Asp Val Met Ser Thr Ala Cys Gly Thr Pro Gly Tyr Val Ala Pro
1               5                   10                  15

Glu Val Leu Ala Gln Lys
            20

<210> SEQ ID NO 142
<211> LENGTH: 22
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: OXIDATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: CARBAMIDOMETHYLATION

<400> SEQUENCE: 142

Gly Asp Val Met Ser Thr Ala Cys Gly Thr Pro Gly Tyr Val Ala Pro
1               5                   10                  15

Glu Val Leu Ala Gln Lys
            20

<210> SEQ ID NO 143
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 143

Gly His Leu Ser Glu Gly Leu Val Thr Lys
1               5                   10

<210> SEQ ID NO 144
<211> LENGTH: 19
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 144

Gly Ser Ala Ala Trp Met Ala Pro Glu Val Phe Glu Gly Ser Asn Tyr
1               5                   10                  15

Ser Glu Lys

<210> SEQ ID NO 145
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION
```

```
<400> SEQUENCE: 145

Gly Gln Glu Val Tyr Val Lys
1               5

<210> SEQ ID NO 146
<211> LENGTH: 19
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (6)..(6)
<223> OTHER INFORMATION: OXIDATION

<400> SEQUENCE: 146

Gly Ser Ala Ala Trp Met Ala Pro Glu Val Phe Glu Gly Ser Asn Tyr
1               5                   10                  15

Ser Glu Lys

<210> SEQ ID NO 147
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 147

Gly Ser Phe Asp Gly Ser Ser Ser Gln Pro Ser Arg
1               5                   10

<210> SEQ ID NO 148
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (12)..(12)
<223> OTHER INFORMATION: CARBAMIDOMETHYLATION

<400> SEQUENCE: 148

Gly Ser Pro Leu Tyr Met Ala Pro Glu Met Val Cys Gln Arg
1               5                   10

<210> SEQ ID NO 149
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (10)..(10)
<223> OTHER INFORMATION: OXIDATION
```

```
<220> FEATURE:
<221> NAME/KEY: MOD_RES
<222> LOCATION: (12)..(12)
<223> OTHER INFORMATION: CARBAMIDOMETHYLATION

<400> SEQUENCE: 149

Gly Ser Pro Leu Tyr Met Ala Pro Glu Met Val Cys Gln Arg
1               5                   10

<210> SEQ ID NO 150
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (13)..(13)
<223> OTHER INFORMATION: CARBAMIDOMETHYLATION

<400> SEQUENCE: 150

Gly Thr Glu Ile Tyr Met Ser Pro Glu Val Ile Leu Cys Arg
1               5                   10

<210> SEQ ID NO 151
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (13)..(13)
<223> OTHER INFORMATION: CARBAMIDOMETHYLATION

<400> SEQUENCE: 151

Gly Thr Glu Ile Tyr Met Ser Pro Glu Val Ile Leu Cys Arg
1               5                   10

<210> SEQ ID NO 152
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 152

Gly Thr Leu Ala Tyr Leu Pro Glu Glu Tyr Ile Lys
1               5                   10

<210> SEQ ID NO 153
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
```

```
<400> SEQUENCE: 153

Gly Val His His Ile Asp Tyr Tyr Lys
1               5

<210> SEQ ID NO 154
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 154

Gly Val His His Ile Asp Tyr Tyr Lys
1               5

<210> SEQ ID NO 155
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 155

Gly Val His His Ile Asp Tyr Tyr Lys
1               5

<210> SEQ ID NO 156
<211> LENGTH: 10
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 156

Gly Tyr Leu Ser Glu Gly Leu Val Thr Lys
1               5                   10

<210> SEQ ID NO 157
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 157

His Ala Asp Ala Glu Met Thr Gly Tyr Val Val Thr Arg
1               5                   10

<210> SEQ ID NO 158
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
```

```
<220> FEATURE:
<221> NAME/KEY: MOD_RES
<222> LOCATION: (9)..(9)
<223> OTHER INFORMATION: PHOSPHORYLATION

<400> SEQUENCE: 158

His Ala Asp Ala Glu Met Thr Gly Tyr Val Val Thr Arg
1               5                   10

<210> SEQ ID NO 159
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 159

His Ala Asp Ala Glu Met Thr Gly Tyr Val Val Thr Arg
1               5                   10

<210> SEQ ID NO 160
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (7)..(7)
<223> OTHER INFORMATION: PHOSPHORYLATION

<400> SEQUENCE: 160

His Ala Asp Ala Glu Met Thr Gly Tyr Val Val Thr Arg
1               5                   10

<210> SEQ ID NO 161
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION

<400> SEQUENCE: 161

His Ala Asp Ala Glu Met Thr Gly Tyr Val Val Thr Arg
1               5                   10

<210> SEQ ID NO 162
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
```

```
<220> FEATURE:
<221> NAME/KEY: MOD_RES
<222> LOCATION: (9)..(9)
<223> OTHER INFORMATION: PHOSPHORYLATION

<400> SEQUENCE: 162

His Ala Asp Ala Glu Met Thr Gly Tyr Val Val Thr Arg
1               5                   10

<210> SEQ ID NO 163
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 163

His Met Thr Gln Glu Val Val Thr Gln Tyr Tyr Arg
1               5                   10

<210> SEQ ID NO 164
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: OXIDATION
<220> FEATURE:
<221> NAME/KEY: MOD_RES
<222> LOCATION: (3)..(3)
<223> OTHER INFORMATION: PHOSPHORYLATION

<400> SEQUENCE: 164

His Met Thr Gln Glu Val Val Thr Gln Tyr Tyr Arg
1               5                   10

<210> SEQ ID NO 165
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 165

His Thr Asp Asp Glu Met Thr Gly Tyr Val Ala Thr Arg
1               5                   10

<210> SEQ ID NO 166
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 166

His Thr Asp Asp Glu Met Thr Gly Tyr Val Ala Thr Arg
1               5                   10
```

-continued

```
<210> SEQ ID NO 167
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 167

His Thr Asp Asp Glu Met Thr Gly Tyr Val Ala Thr Arg
1               5                   10

<210> SEQ ID NO 168
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (7)..(7)
<223> OTHER INFORMATION: PHOSPHORYLATION

<400> SEQUENCE: 168

His Thr Asp Asp Glu Met Thr Gly Tyr Val Ala Thr Arg
1               5                   10

<210> SEQ ID NO 169
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION

<400> SEQUENCE: 169

His Thr Asp Asp Glu Met Thr Gly Tyr Val Ala Thr Arg
1               5                   10

<210> SEQ ID NO 170
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (9)..(9)
<223> OTHER INFORMATION: PHOSPHORYLATION

<400> SEQUENCE: 170

His Thr Asp Asp Glu Met Thr Gly Tyr Val Ala Thr Arg
1               5                   10
```

-continued

```
<210> SEQ ID NO 171
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 171

Ile Ala Asp Leu Gly Leu Ala Ser Phe Lys
1               5                   10

<210> SEQ ID NO 172
<211> LENGTH: 19
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION

<400> SEQUENCE: 172

Ile Ala Asp Pro Glu His Asp His Thr Gly Phe Leu Thr Glu Tyr Val
1               5                   10                  15

Ala Thr Arg

<210> SEQ ID NO 173
<211> LENGTH: 19
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION

<400> SEQUENCE: 173

Ile Ala Asp Pro Glu His Asp His Thr Gly Phe Leu Thr Glu Tyr Val
1               5                   10                  15

Ala Thr Arg

<210> SEQ ID NO 174
<211> LENGTH: 19
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION

<400> SEQUENCE: 174

Ile Ala Asp Pro Glu His Asp His Thr Gly Phe Leu Thr Glu Tyr Val
1               5                   10                  15

Ala Thr Arg

<210> SEQ ID NO 175
<211> LENGTH: 8
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: CARBAMIDOMETHYLATION
<220> FEATURE:
<221> NAME/KEY: MOD_RES
<222> LOCATION: (7)..(7)
<223> OTHER INFORMATION: PHOSPHORYLATION
```

```
<400> SEQUENCE: 175

Ile Cys Asp Phe Gly Ala Ser Arg
1               5

<210> SEQ ID NO 176
<211> LENGTH: 25
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 176

Ile Asp Gln Gly Asp Leu Met Thr Pro Gln Phe Thr Pro Tyr Tyr Val
1               5                   10                  15

Ala Pro Gln Val Leu Glu Ala Gln Arg
            20                  25

<210> SEQ ID NO 177
<211> LENGTH: 25
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: OXIDATION
<220> FEATURE:
<221> NAME/KEY: MOD_RES
<222> LOCATION: (8)..(8)
<223> OTHER INFORMATION: PHOSPHORYLATION

<400> SEQUENCE: 177

Ile Asp Gln Gly Asp Leu Met Thr Pro Gln Phe Thr Pro Tyr Tyr Val
1               5                   10                  15

Ala Pro Gln Val Leu Glu Ala Gln Arg
            20                  25

<210> SEQ ID NO 178
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 178

Ile Ile Asp Ser Glu Tyr Thr Ala Gln Glu Gly Ala Lys
1               5                   10

<210> SEQ ID NO 179
<211> LENGTH: 8
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 179

Ile Tyr Asn Gly Asp Tyr Tyr Arg
1               5
```

```
<210> SEQ ID NO 180
<211> LENGTH: 8
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 180

Ile Tyr Ser Gly Asp Tyr Tyr Arg
1               5

<210> SEQ ID NO 181
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 181

Ile Tyr Ser Gly Asp Tyr Tyr Arg
1               5

<210> SEQ ID NO 182
<211> LENGTH: 8
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 182

Ile Tyr Ser Gly Asp Tyr Tyr Arg
1               5

<210> SEQ ID NO 183
<211> LENGTH: 16
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 183

Leu Ala Val Val Gly Ser Pro Phe Trp Met Ala Pro Glu Val Leu Arg
1               5                   10                  15

<210> SEQ ID NO 184
<211> LENGTH: 16
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (10)..(10)
<223> OTHER INFORMATION: OXIDATION

<400> SEQUENCE: 184

Leu Ala Val Val Gly Ser Pro Phe Trp Met Ala Pro Glu Val Leu Arg
1               5                   10                  15
```

```
<210> SEQ ID NO 185
<211> LENGTH: 16
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: CARBAMIDOMETHYLATION
<220> FEATURE:
<221> NAME/KEY: MOD_RES
<222> LOCATION: (13)..(13)
<223> OTHER INFORMATION: PHOSPHORYLATION

<400> SEQUENCE: 185

Leu Cys Asp Phe Gly Ile Ser Gly Gln Leu Val Asp Ser Ile Ala Lys
1               5                   10                  15

<210> SEQ ID NO 186
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (7)..(7)
<223> OTHER INFORMATION: CARBAMIDOMETHYLATION

<400> SEQUENCE: 186

Leu Ala Asp Phe Gly Ser Cys Leu Arg
1               5

<210> SEQ ID NO 187
<211> LENGTH: 15
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 187

Ile Ala Asp Phe Gly Phe Ser Asn Glu Phe Thr Val Gly Asn Lys
1               5                   10                  15

<210> SEQ ID NO 188
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 188

Leu Tyr Thr Tyr Ile Gln Ser Arg
1               5

<210> SEQ ID NO 189
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION
```

```
<400> SEQUENCE: 189

Met Met Ser Leu Ser Gln Ser Arg
1               5

<210> SEQ ID NO 190
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: OXIDATION
<220> FEATURE:
<221> NAME/KEY: MOD_RES
<222> LOCATION: (2)..(2)
<223> OTHER INFORMATION: OXIDATION
<220> FEATURE:
<221> NAME/KEY: MOD_RES
<222> LOCATION: (5)..(5)
<223> OTHER INFORMATION: PHOSPHORYLATION

<400> SEQUENCE: 190

Met Met Ser Leu Ser Gln Ser Arg
1               5

<210> SEQ ID NO 191
<211> LENGTH: 16
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 191

Met Ser Thr Ala Gly Thr Tyr Ala Trp Met Ala Pro Glu Val Ile Lys
1               5                   10                  15

<210> SEQ ID NO 192
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: OXIDATION
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (10)..(10)
<223> OTHER INFORMATION: OXIDATION

<400> SEQUENCE: 192

Met Ser Thr Ala Gly Thr Tyr Ala Trp Met Ala Pro Glu Val Ile Lys
1               5                   10                  15

<210> SEQ ID NO 193
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
```

```
<400> SEQUENCE: 193

Asn Asp Ser Asn Tyr Val Val Lys
1               5

<210> SEQ ID NO 194
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION

<400> SEQUENCE: 194

Asn Asp Ser Asn Tyr Val Val Lys
1               5

<210> SEQ ID NO 195
<211> LENGTH: 8
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION

<400> SEQUENCE: 195

Asn Asp Ser Asn Tyr Val Val Lys
1               5

<210> SEQ ID NO 196
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 196

Asn Ile Tyr Ser Ala Asp Tyr Tyr Lys
1               5

<210> SEQ ID NO 197
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 197

Asn Leu Tyr Ala Gly Asp Tyr Tyr Arg
1               5

<210> SEQ ID NO 198
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
```

```
<400> SEQUENCE: 198

Asn Leu Tyr Ala Gly Asp Tyr Tyr Arg
1               5

<210> SEQ ID NO 199
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 199

Asn Leu Tyr Ala Gly Asp Tyr Tyr Arg
1               5

<210> SEQ ID NO 200
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 200

Asn Leu Tyr Ser Gly Asp Tyr Tyr Arg
1               5

<210> SEQ ID NO 201
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 201

Asn Leu Tyr Ser Gly Asp Tyr Tyr Arg
1               5

<210> SEQ ID NO 202
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 202

Asn Leu Tyr Ser Gly Asp Tyr Tyr Arg
1               5

<210> SEQ ID NO 203
<211> LENGTH: 16
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION

<400> SEQUENCE: 203

Pro Gly Glu Glu Asp Asn Ala Ala Ile Ser Glu Val Gly Thr Ile Arg
1               5                   10                  15
```

```
<210> SEQ ID NO 204
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 204

Gln Ala Asp Glu Glu Met Thr Gly Tyr Val Ala Thr Arg
1               5                   10

<210> SEQ ID NO 205
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 205

Gln Ala Asp Glu Glu Met Thr Gly Tyr Val Ala Thr Arg
1               5                   10

<210> SEQ ID NO 206
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 206

Gln Ala Asp Glu Glu Met Thr Gly Tyr Val Ala Thr Arg
1               5                   10

<210> SEQ ID NO 207
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (7)..(7)
<223> OTHER INFORMATION: PHOSPHORYLATION

<400> SEQUENCE: 207

Gln Ala Asp Glu Glu Met Thr Gly Tyr Val Ala Thr Arg
1               5                   10
```

```
<210> SEQ ID NO 208
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION

<400> SEQUENCE: 208

Gln Ala Asp Glu Glu Met Thr Gly Tyr Val Ala Thr Arg
1               5                   10

<210> SEQ ID NO 209
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (9)..(9)
<223> OTHER INFORMATION: PHOSPHORYLATION

<400> SEQUENCE: 209

Gln Ala Asp Glu Glu Met Thr Gly Tyr Val Ala Thr Arg
1               5                   10

<210> SEQ ID NO 210
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 210

Gln Ala Asp Ser Glu Met Thr Gly Tyr Val Val Thr Arg
1               5                   10

<210> SEQ ID NO 211
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 211

Gln Ala Asp Ser Glu Met Thr Gly Tyr Val Val Thr Arg
1               5                   10

<210> SEQ ID NO 212
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
```

```
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 212

Gln Ala Asp Ser Glu Met Thr Gly Tyr Val Val Thr Arg
1               5                   10

<210> SEQ ID NO 213
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (7)..(7)
<223> OTHER INFORMATION: PHOSPHORYLATION

<400> SEQUENCE: 213

Gln Ala Asp Ser Glu Met Thr Gly Tyr Val Val Thr Arg
1               5                   10

<210> SEQ ID NO 214
<211> LENGTH: 13
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION

<400> SEQUENCE: 214

Gln Ala Asp Ser Glu Met Thr Gly Tyr Val Val Thr Arg
1               5                   10

<210> SEQ ID NO 215
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: OXIDATION
<220> FEATURE:
<221> NAME/KEY: MOD_RES
<222> LOCATION: (9)..(9)
<223> OTHER INFORMATION: PHOSPHORYLATION

<400> SEQUENCE: 215

Gln Ala Asp Ser Glu Met Thr Gly Tyr Val Val Thr Arg
1               5                   10

<210> SEQ ID NO 216
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION
```

```
<400> SEQUENCE: 216

Gln Ala Leu Thr Leu Gln Asp Trp Ala Ala Gln Arg
1               5                   10

<210> SEQ ID NO 217
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: CARBAMIDOMETHYLATION
<220> FEATURE:
<221> NAME/KEY: MOD_RES
<222> LOCATION: (4)..(4)
<223> OTHER INFORMATION: PHOSPHORYLATION

<400> SEQUENCE: 217

Cys Thr Ile Ser Tyr Arg
1               5

<210> SEQ ID NO 218
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: CARBAMIDOMETHYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION

<400> SEQUENCE: 218

Cys Thr Ile Ser Tyr Arg
1               5

<210> SEQ ID NO 219
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: CARBAMIDOMETHYLATION
<220> FEATURE:
<221> NAME/KEY: MOD_RES
<222> LOCATION: (5)..(5)
<223> OTHER INFORMATION: PHOSPHORYLATION

<400> SEQUENCE: 219

Cys Thr Ile Ser Tyr Arg
1               5

<210> SEQ ID NO 220
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
```

<400> SEQUENCE: 220

Gln Glu Asp Gly Gly Val Tyr Ser Ser Ser Gly Leu Lys
1               5                   10

<210> SEQ ID NO 221
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (6)..(6)
<223> OTHER INFORMATION: CARBAMIDOMETHYLATION

<400> SEQUENCE: 221

Gln Glu Thr Val Glu Cys Leu Lys
1               5

<210> SEQ ID NO 222
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION

<400> SEQUENCE: 222

Gln Ser Gly Val Val Val Glu Glu Pro Pro Pro Ser Lys
1               5                   10

<210> SEQ ID NO 223
<211> LENGTH: 13
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 223

Asn Ser Ser Pro Ala Pro Pro Gln Pro Ala Pro Gly Lys
1               5                   10

<210> SEQ ID NO 224
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION

<400> SEQUENCE: 224

Ser Leu Val Gly Thr Pro Tyr Trp Met Ala Pro Glu Leu Ile Ser Arg
1               5                   10                  15

<210> SEQ ID NO 225
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION

```
<220> FEATURE:
<221> NAME/KEY: MOD_RES
<222> LOCATION: (9)..(9)
<223> OTHER INFORMATION: OXIDATION

<400> SEQUENCE: 225

Ser Leu Val Gly Thr Pro Tyr Trp Met Ala Pro Glu Leu Ile Ser Arg
1               5                   10                  15

<210> SEQ ID NO 226
<211> LENGTH: 26
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 226

Ser Asp Pro Ser Gly His Leu Thr Gly Met Val Gly Thr Ala Leu Tyr
1               5                   10                  15

Val Ser Pro Glu Val Gln Gly Ser Thr Lys
            20                  25

<210> SEQ ID NO 227
<211> LENGTH: 26
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: OXIDATION

<400> SEQUENCE: 227

Ser Asp Pro Ser Gly His Leu Thr Gly Met Val Gly Thr Ala Leu Tyr
1               5                   10                  15

Val Ser Pro Glu Val Gln Gly Ser Thr Lys
            20                  25

<210> SEQ ID NO 228
<211> LENGTH: 26
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION

<400> SEQUENCE: 228

Ser Asp Pro Ser Gly His Leu Thr Gly Met Val Gly Thr Ala Leu Tyr
1               5                   10                  15

Val Ser Pro Glu Val Gln Gly Ser Thr Lys
            20                  25

<210> SEQ ID NO 229
<211> LENGTH: 26
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: OXIDATION
```

```
<220> FEATURE:
<221> NAME/KEY: MOD_RES
<222> LOCATION: (13)..(13)
<223> OTHER INFORMATION: PHOSPHORYLATION

<400> SEQUENCE: 229

Ser Asp Pro Ser Gly His Leu Thr Gly Met Val Gly Thr Ala Leu Tyr
1               5                   10                  15

Val Ser Pro Glu Val Gln Gly Ser Thr Lys
            20                  25

<210> SEQ ID NO 230
<211> LENGTH: 22
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 230

Ser Glu Ile Gly His Ser Pro Pro Ala Tyr Thr Pro Met Ser Gly
1               5                   10                  15

Asn Gln Phe Val Tyr Arg
            20

<210> SEQ ID NO 231
<211> LENGTH: 7
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 231

Ser Phe Gly Ser Pro Asn Arg
1               5

<210> SEQ ID NO 232
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 232

Ala Tyr Thr His Gln Val Val Thr Arg
1               5

<210> SEQ ID NO 233
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: CARBAMIDOMETHYLATION
<220> FEATURE:
<221> NAME/KEY: MOD_RES
<222> LOCATION: (9)..(9)
<223> OTHER INFORMATION: PHOSPHORYLATION

<400> SEQUENCE: 233

Cys Leu Thr Ser Asn Leu Leu Gln Ser Arg
1               5                   10
```

```
<210> SEQ ID NO 234
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (9)..(9)
<223> OTHER INFORMATION: CARBAMIDOMETHYLATION

<400> SEQUENCE: 234

Asp Tyr Leu Ser Ser Ser Phe Leu Cys Ser Asp Asp Asp Arg
1               5                   10

<210> SEQ ID NO 235
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (9)..(9)
<223> OTHER INFORMATION: CARBAMIDOMETHYLATION
<220> FEATURE:
<221> NAME/KEY: MOD_RES
<222> LOCATION: (10)..(10)
<223> OTHER INFORMATION: PHOSPHORYLATION

<400> SEQUENCE: 235

Asp Tyr Leu Ser Ser Ser Phe Leu Cys Ser Asp Asp Asp Arg
1               5                   10

<210> SEQ ID NO 236
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION

<400> SEQUENCE: 236

Gly Val Glu Asn Pro Ala Val Gln Glu Ser Asn Gln Lys
1               5                   10

<210> SEQ ID NO 237
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION

<400> SEQUENCE: 237

Ser Phe Asn Ser His Ile Asn Ala Ser Asn Ser Glu Pro Ser Arg
1               5                   10                  15

<210> SEQ ID NO 238
<211> LENGTH: 16
<212> TYPE: PRT
<213> ORGANISM: Homo sapiens
```

```
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 238

Ser Phe Asn Ser His Ile Asn Ala Ser Asn Asn Ser Glu Pro Ser Arg
1               5                   10                  15

<210> SEQ ID NO 239
<211> LENGTH: 16
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION

<400> SEQUENCE: 239

Ser Phe Asn Ser His Ile Asn Ala Ser Asn Asn Ser Glu Pro Ser Arg
1               5                   10                  15

<210> SEQ ID NO 240
<211> LENGTH: 16
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 240

Ile Leu Gly Thr Pro Asp Tyr Leu Ala Pro Glu Leu Leu Leu Gly Arg
1               5                   10                  15

<210> SEQ ID NO 241
<211> LENGTH: 23
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: CARBAMIDOMETHYLATION

<400> SEQUENCE: 241

Ser Gly Glu Pro Leu Ser Thr Trp Cys Gly Ser Pro Pro Tyr Ala Ala
1               5                   10                  15

Pro Glu Val Phe Glu Gly Lys
            20

<210> SEQ ID NO 242
<211> LENGTH: 21
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION
```

```
<400> SEQUENCE: 242

Ser Val Val Gly Thr Pro Ala Tyr Leu Ala Pro Glu Val Leu Leu Asn
1               5                   10                  15

Gln Gly Tyr Asn Arg
            20

<210> SEQ ID NO 243
<211> LENGTH: 21
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 243

Ser Val Val Gly Thr Pro Ala Tyr Leu Ala Pro Glu Val Leu Leu Asn
1               5                   10                  15

Gln Gly Tyr Asn Arg
            20

<210> SEQ ID NO 244
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (3)..(3)
<223> OTHER INFORMATION: CARBAMIDOMETHYLATION

<400> SEQUENCE: 244

Thr Ile Cys Gly Thr Pro Asn Tyr Leu Ser Pro Glu Val Leu Asn Lys
1               5                   10                  15

<210> SEQ ID NO 245
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 245

Ile Leu Gly Glu Thr Ser Leu Met Arg
1               5

<210> SEQ ID NO 246
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: OXIDATION

<400> SEQUENCE: 246

Ile Leu Gly Glu Thr Ser Leu Met Arg
1               5
```

```
<210> SEQ ID NO 247
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (3)..(3)
<223> OTHER INFORMATION: CARBAMIDOMETHYLATION
<220> FEATURE:
<221> NAME/KEY: MOD_RES
<222> LOCATION: (9)..(9)
<223> OTHER INFORMATION: CARBAMIDOMETHYLATION

<400> SEQUENCE: 247

Thr Val Cys Gly Thr Pro Gly Tyr Cys Ala Pro Glu Ile Leu Arg
1               5                   10                  15

<210> SEQ ID NO 248
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION

<400> SEQUENCE: 248

Thr Tyr Val Gly Thr Asn Ala Tyr Met Ala Pro Glu Arg
1               5                   10

<210> SEQ ID NO 249
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (9)..(9)
<223> OTHER INFORMATION: OXIDATION

<400> SEQUENCE: 249

Thr Tyr Val Gly Thr Asn Ala Tyr Met Ala Pro Glu Arg
1               5                   10

<210> SEQ ID NO 250
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: CARBAMIDOMETHYLATION
<220> FEATURE:
<221> NAME/KEY: MOD_RES
<222> LOCATION: (9)..(9)
<223> OTHER INFORMATION: PHOSPHORYLATION

<400> SEQUENCE: 250

Thr Ala Cys Thr Asn Phe Met Met Thr Pro Tyr Val Val Thr Arg
1               5                   10                  15
```

```
<210> SEQ ID NO 251
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: CARBAMIDOMETHYLATION
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 251

Thr Ala Cys Thr Asn Phe Met Met Thr Pro Tyr Val Val Thr Arg
1               5                   10                  15

<210> SEQ ID NO 252
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: CARBAMIDOMETHYLATION
<220> FEATURE:
<221> NAME/KEY: MOD_RES
<222> LOCATION: (7)..(7)
<223> OTHER INFORMATION: OXIDATION
<220> FEATURE:
<221> NAME/KEY: MOD_RES
<222> LOCATION: (8)..(8)
<223> OTHER INFORMATION: OXIDATION
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 252

Thr Ala Cys Thr Asn Phe Met Met Thr Pro Tyr Val Val Thr Arg
1               5                   10                  15

<210> SEQ ID NO 253
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: CARBAMIDOMETHYLATION
<220> FEATURE:
<221> NAME/KEY: MOD_RES
<222> LOCATION: (11)..(11)
<223> OTHER INFORMATION: PHOSPHORYLATION

<400> SEQUENCE: 253

Thr Ala Cys Thr Asn Phe Met Met Thr Pro Tyr Val Val Thr Arg
1               5                   10                  15

<210> SEQ ID NO 254
<211> LENGTH: 15
<212> TYPE: PRT
<213> ORGANISM: Homo sapiens
```

```
<220> FEATURE:
<221> NAME/KEY: MOD_RES
<222> LOCATION: (3)..(3)
<223> OTHER INFORMATION: CARBAMIDOMETHYLATION
<220> FEATURE:
<221> NAME/KEY: MOD_RES
<222> LOCATION: (7)..(7)
<223> OTHER INFORMATION: OXIDATION
<220> FEATURE:
<221> NAME/KEY: MOD_RES
<222> LOCATION: (8)..(8)
<223> OTHER INFORMATION: OXIDATION
<220> FEATURE:
<221> NAME/KEY: MOD_RES
<222> LOCATION: (11)..(11)
<223> OTHER INFORMATION: PHOSPHORYLATION

<400> SEQUENCE: 254

Thr Ala Cys Thr Asn Phe Met Met Thr Pro Tyr Val Val Thr Arg
1               5                   10                  15

<210> SEQ ID NO 255
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 255

Ile Leu Asn His Asp Thr Ser Phe Ala Lys
1               5                   10

<210> SEQ ID NO 256
<211> LENGTH: 10
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 256

Ile Leu Asn His Asp Thr Ser Phe Ala Lys
1               5                   10

<210> SEQ ID NO 257
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 257

Ile Leu Asn His Asp Thr Ser Phe Ala Lys
1               5                   10

<210> SEQ ID NO 258
<211> LENGTH: 16
<212> TYPE: PRT
<213> ORGANISM: Homo sapiens
```

```
<220> FEATURE:
<221> NAME/KEY: MOD_RES
<222> LOCATION: (1)..(1)
<223> OTHER INFORMATION: PHOSPHORYLATION

<400> SEQUENCE: 258

Thr Phe Val Gly Thr Pro Tyr Tyr Met Ser Pro Glu Gln Met Asn Arg
1               5                   10                  15

<210> SEQ ID NO 259
<211> LENGTH: 16
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION

<400> SEQUENCE: 259

Thr Phe Val Gly Thr Pro Tyr Tyr Met Ser Pro Glu Gln Met Asn Arg
1               5                   10                  15

<210> SEQ ID NO 260
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (3)..(3)
<223> OTHER INFORMATION: CARBAMIDOMETHYLATION

<400> SEQUENCE: 260

Thr Leu Cys Gly Thr Pro Asn Tyr Ile Ala Pro Glu Val Leu Ser Lys
1               5                   10                  15

<210> SEQ ID NO 261
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (3)..(3)
<223> OTHER INFORMATION: CARBAMIDOMETHYLATION
<220> FEATURE:
<221> NAME/KEY: MOD_RES
<222> LOCATION: (5)..(5)
<223> OTHER INFORMATION: PHOSPHORYLATION

<400> SEQUENCE: 261

Thr Leu Cys Gly Thr Pro Asn Tyr Ile Ala Pro Glu Val Leu Ser Lys
1               5                   10                  15

<210> SEQ ID NO 262
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: CARBAMIDOMETHYLATION
```

```
<220> FEATURE:
<221> NAME/KEY: MOD_RES
<222> LOCATION: (5)..(5)
<223> OTHER INFORMATION: PHOSPHORYLATION

<400> SEQUENCE: 262

Thr Leu Cys Gly Thr Pro Asn Tyr Ile Ala Pro Glu Val Leu Ser Lys
1               5                   10                  15

<210> SEQ ID NO 263
<211> LENGTH: 20
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: CARBAMIDOMETHYLATION

<400> SEQUENCE: 263

Thr Asn Thr Phe Cys Gly Thr Pro Asp Tyr Ile Ala Pro Glu Ile Leu
1               5                   10                  15

Leu Gly Gln Lys
            20

<210> SEQ ID NO 264
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 264

Thr Gln Thr Ser Met Ser Leu Gly Thr Thr Arg
1               5                   10

<210> SEQ ID NO 265
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (5)..(5)
<223> OTHER INFORMATION: OXIDATION

<400> SEQUENCE: 265

Thr Gln Thr Ser Met Ser Leu Gly Thr Thr Arg
1               5                   10

<210> SEQ ID NO 266
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
```

```
<400> SEQUENCE: 266

Thr Gln Thr Ser Met Ser Leu Gly Thr Thr Arg
1               5                   10

<210> SEQ ID NO 267
<211> LENGTH: 11
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: OXIDATION
<220> FEATURE:
<221> NAME/KEY: MOD_RES
<222> LOCATION: (6)..(6)
<223> OTHER INFORMATION: PHOSPHORYLATION

<400> SEQUENCE: 267

Thr Gln Thr Ser Met Ser Leu Gly Thr Thr Arg
1               5                   10

<210> SEQ ID NO 268
<211> LENGTH: 23
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: CARBAMIDOMETHYLATION

<400> SEQUENCE: 268

Thr Ser Thr Phe Cys Gly Thr Pro Glu Phe Leu Ala Pro Glu Val Leu
1               5                   10                  15

Thr Glu Thr Ser Tyr Thr Arg
            20

<210> SEQ ID NO 269
<211> LENGTH: 23
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: CARBAMIDOMETHYLATION
<220> FEATURE:
<221> NAME/KEY: MOD_RES
<222> LOCATION: (7)..(7)
<223> OTHER INFORMATION: PHOSPHORYLATION

<400> SEQUENCE: 269

Thr Ser Thr Phe Cys Gly Thr Pro Glu Phe Leu Ala Pro Glu Val Leu
1               5                   10                  15

Thr Glu Thr Ser Tyr Thr Arg
            20

<210> SEQ ID NO 270
<211> LENGTH: 23
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
```

```
<220> FEATURE:
<221> NAME/KEY: MOD_RES
<222> LOCATION: (5)..(5)
<223> OTHER INFORMATION: CARBAMIDOMETHYLATION

<400> SEQUENCE: 270

Thr Ser Thr Phe Cys Gly Thr Pro Glu Phe Leu Ala Pro Glu Val Leu
1               5                   10                  15

Thr Gln Glu Ala Tyr Thr Arg
            20

<210> SEQ ID NO 271
<211> LENGTH: 23
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: CARBAMIDOMETHYLATION
<220> FEATURE:
<221> NAME/KEY: MOD_RES
<222> LOCATION: (7)..(7)
<223> OTHER INFORMATION: PHOSPHORYLATION

<400> SEQUENCE: 271

Thr Ser Thr Phe Cys Gly Thr Pro Glu Phe Leu Ala Pro Glu Val Leu
1               5                   10                  15

Thr Gln Glu Ala Tyr Thr Arg
            20

<210> SEQ ID NO 272
<211> LENGTH: 19
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION

<400> SEQUENCE: 272

Thr Thr Gln Met Ser Ala Ala Gly Thr Tyr Ala Trp Met Ala Pro Glu
1               5                   10                  15

Val Ile Lys

<210> SEQ ID NO 273
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: CARBAMIDOMETHYLATION
<220> FEATURE:
<221> NAME/KEY: MOD_RES
<222> LOCATION: (6)..(6)
<223> OTHER INFORMATION: PHOSPHORYLATION

<400> SEQUENCE: 273

Thr Val Cys Ser Thr Tyr Leu Gln Ser Arg
1               5                   10

<210> SEQ ID NO 274
<211> LENGTH: 19
<212> TYPE: PRT
<213> ORGANISM: Homo sapiens
```

```
<220> FEATURE:
<221> NAME/KEY: MOD_RES
<222> LOCATION: (13)..(13)
<223> OTHER INFORMATION: PHOSPHORYLATION

<400> SEQUENCE: 274

Val Ala Asp Pro Asp His Asp His Thr Gly Phe Leu Thr Glu Tyr Val
1               5                   10                  15

Ala Thr Arg

<210> SEQ ID NO 275
<211> LENGTH: 19
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION

<400> SEQUENCE: 275

Val Ala Asp Pro Asp His Asp His Thr Gly Phe Leu Thr Glu Tyr Val
1               5                   10                  15

Ala Thr Arg

<210> SEQ ID NO 276
<211> LENGTH: 19
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: PHOSPHORYLATION

<400> SEQUENCE: 276

Val Ala Asp Pro Asp His Asp His Thr Gly Phe Leu Thr Glu Tyr Val
1               5                   10                  15

Ala Thr Arg

<210> SEQ ID NO 277
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 277

Val Asp Asn Glu Asp Ile Tyr Glu Ser Arg
1               5                   10

<210> SEQ ID NO 278
<211> LENGTH: 16
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION

<400> SEQUENCE: 278

Val Ile Glu Asp Asp Pro Glu Ala Val Tyr Thr Thr Thr Gly Gly Lys
1               5                   10                  15
```

```
<210> SEQ ID NO 279
<211> LENGTH: 16
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION

<400> SEQUENCE: 279

Val Leu Glu Asp Asp Pro Glu Ala Ala Tyr Thr Thr Thr Gly Gly Lys
1               5                   10                  15

<210> SEQ ID NO 280
<211> LENGTH: 13
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 280

His Pro Gly His Tyr Ala Val Tyr Asn Leu Ser Pro Arg
1               5                   10

<210> SEQ ID NO 281
<211> LENGTH: 21
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 281

Asp Glu Ser Glu Val Ser Asp Glu Gly Gly Ser Pro Ile Ser Ser Glu
1               5                   10                  15

Gly Gln Glu Pro Arg
            20

<210> SEQ ID NO 282
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 282

Asp Glu Ser Glu Val Ser Asp Glu Gly Gly Ser Pro Ile Ser Ser Glu
1               5                   10                  15

Gly Gln Glu Pro Arg
            20

<210> SEQ ID NO 283
<211> LENGTH: 18
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
```

```
<400> SEQUENCE: 283

Val Ser Glu Asn Asp Phe Glu Asp Leu Leu Ser Asn Gln Gly Phe Ser
1               5                   10                  15

Ser Arg

<210> SEQ ID NO 284
<211> LENGTH: 18
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 284

Val Ser Glu Asn Asp Phe Glu Asp Leu Leu Ser Asn Gln Gly Phe Ser
1               5                   10                  15

Ser Arg

<210> SEQ ID NO 285
<211> LENGTH: 21
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: PHOSPHORYLATION

<400> SEQUENCE: 285

Val Val Asp Phe Gly Ser Ala Thr Phe Asp His Glu His His Ser Thr
1               5                   10                  15

Ile Val Ser Thr Arg
            20

<210> SEQ ID NO 286
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION

<400> SEQUENCE: 286

Val Tyr Thr His Glu Val Val Thr Leu Trp Tyr Arg
1               5                   10

<210> SEQ ID NO 287
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 287

Ser Pro Glu Val Leu Leu Gly Ser Ala Arg
1               5                   10
```

```
<210> SEQ ID NO 288
<211> LENGTH: 16
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 288

Val Leu Glu Asp Asp Pro Glu Ala Thr Tyr Thr Thr Ser Gly Gly Lys
1               5                   10                  15

<210> SEQ ID NO 289
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 289

Trp Thr Ala Pro Glu Ala Ile Ser Tyr Arg
1               5                   10

<210> SEQ ID NO 290
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 290

Trp Thr Ala Pro Glu Ala Ile Ser Tyr Arg
1               5                   10

<210> SEQ ID NO 291
<211> LENGTH: 10
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION

<400> SEQUENCE: 291

Trp Thr Ala Pro Glu Ala Ile Ser Tyr Arg
1               5                   10

<210> SEQ ID NO 292
<211> LENGTH: 7
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: PHOSPHORYLATION
```

```
<400> SEQUENCE: 292

Ala Asp Glu Asn Tyr Tyr Lys
1               5

<210> SEQ ID NO 293
<211> LENGTH: 7
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 293

Ala Asp Glu Asn Tyr Tyr Lys
1               5

<210> SEQ ID NO 294
<211> LENGTH: 11
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: CARBAMIDOMETHYLATION
<220> FEATURE:
<221> NAME/KEY: MOD_RES
<222> LOCATION: (9)..(9)
<223> OTHER INFORMATION: PHOSPHORYLATION

<400> SEQUENCE: 294

Trp Tyr Ala Pro Glu Cys Ile Asn Tyr Tyr Lys
1               5                   10

<210> SEQ ID NO 295
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 295

Val Ala Gly Ser Gln Pro Ile Thr Val Ala Trp Tyr Lys
1               5                   10

<210> SEQ ID NO 296
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 296

Val Ala Gly Ser Gln Pro Ile Thr Val Ala Trp Tyr Lys
1               5                   10

<210> SEQ ID NO 297
<211> LENGTH: 13
<212> TYPE: PRT
<213> ORGANISM: Homo sapiens
```

```
<220> FEATURE:
<221> NAME/KEY: MOD_RES
<222> LOCATION: (8)..(8)
<223> OTHER INFORMATION: PHOSPHORYLATION

<400> SEQUENCE: 297

Val Ala Gly Ser Gln Pro Ile Thr Val Ala Trp Tyr Lys
1               5                   10

<210> SEQ ID NO 298
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION

<400> SEQUENCE: 298

Tyr Met Glu Asp Ser Thr Tyr Tyr Lys
1               5

<210> SEQ ID NO 299
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (2)..(2)
<223> OTHER INFORMATION: OXIDATION

<400> SEQUENCE: 299

Tyr Met Glu Asp Ser Thr Tyr Tyr Lys
1               5

<210> SEQ ID NO 300
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 300

Tyr Met Glu Asp Ser Thr Tyr Tyr Lys
1               5

<210> SEQ ID NO 301
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: OXIDATION
<220> FEATURE:
<221> NAME/KEY: MOD_RES
<222> LOCATION: (7)..(7)
<223> OTHER INFORMATION: PHOSPHORYLATION

<400> SEQUENCE: 301

Tyr Met Glu Asp Ser Thr Tyr Tyr Lys
1               5
```

```
<210> SEQ ID NO 302
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 302

Tyr Met Glu Asp Ser Thr Tyr Tyr Lys
1               5

<210> SEQ ID NO 303
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: OXIDATION
<220> FEATURE:
<221> NAME/KEY: MOD_RES
<222> LOCATION: (8)..(8)
<223> OTHER INFORMATION: PHOSPHORYLATION

<400> SEQUENCE: 303

Tyr Met Glu Asp Ser Thr Tyr Tyr Lys
1               5

<210> SEQ ID NO 304
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 304

Tyr Ile Glu Asp Glu Asp Tyr Tyr Lys
1               5

<210> SEQ ID NO 305
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 305

Tyr Ile Glu Asp Glu Asp Tyr Tyr Lys
1               5

<210> SEQ ID NO 306
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION
```

```
<400> SEQUENCE: 306

Tyr Ile Glu Asp Glu Asp Tyr Tyr Lys
1               5

<210> SEQ ID NO 307
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 307

Tyr Val Leu Asp Asp Glu Tyr Thr Ser Ser Val Gly Ser Lys
1               5                   10

<210> SEQ ID NO 308
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 308

Tyr Val Leu Asp Asp Glu Tyr Val Ser Ser Phe Gly Ala Lys
1               5                   10

<210> SEQ ID NO 309
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 309

Tyr Val Leu Asp Asp Gln Tyr Thr Ser Ser Ser Gly Ala Lys
1               5                   10

<210> SEQ ID NO 310
<211> LENGTH: 14
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 310

Tyr Val Leu Asp Asp Gln Tyr Val Ser Ser Val Gly Thr Lys
1               5                   10
```